United States Patent
Aebi et al.

(10) Patent No.: US 6,706,751 B2
(45) Date of Patent: Mar. 16, 2004

(54) DIHYDROINDOLE AND TETRAHYDROQUINOLINE DERIVATIVES

(75) Inventors: Johannes Aebi, Basle (CH); Jean Ackermann, Riehen (CH); Alexander Chucholowski, San Diego, CA (US); Henrietta Dehmlow, Grenzach-Wyhlen (DE); Olivier Morand, Hegenheim (FR); Sabine Wallbaum, Ostfildern (DE); Thomas Weller, Binningen (CH); Narendra Panday, Basle (CH)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 10/014,959

(22) Filed: Dec. 11, 2001

(65) Prior Publication Data

US 2003/0004156 A1 Jan. 2, 2003

(30) Foreign Application Priority Data

Dec. 21, 2000 (EP) .............................. 00128063

(51) Int. Cl.[7] ..................... A61P 43/00; C07D 207/02; A61K 31/40
(52) U.S. Cl. .................. 514/415; 514/418; 548/503
(58) Field of Search ................ 514/415, 418; 548/503

(56) References Cited

FOREIGN PATENT DOCUMENTS

| EP | 0 318 860 | 6/1989 |
|----|-----------|--------|
| EP | 636 367 | 2/1995 |
| WO | WO 93 12754 | 7/1993 |
| WO | WO 97 28128 | 8/1997 |
| WO | WO 99 00371 | 1/1999 |
| WO | WO 01 87834 | 11/2001 |

OTHER PUBLICATIONS

Gotto et al., Circulation 81, pp. 1721–1733 (1990).
Stein et al., Nutr. Metab. Cardiovasc. Dis. 2, pp. 113–156 (1992).
Illingworth, Med. Clin. North Am. 84, pp. 23–42 (2000).
Ross et al., Arch. Intern. Med. 159, pp. 1793–1802 (1999).
Ellen et al., J. Cardiol. 81, pp. 60B–65B (1998).
Shepherd, Eur. Heart J. 16, pp. 5–13 (1995).
Davignon et al., Can. J. Cardiol 8, pp. 843–864 (1992).
Pedersen et al., Drug Safety 14, pp. 11–24 (1996).
Morand et al., J. Lipid Research 38, pp. 373–390 (1997).
Mark et al., J. Lipid Research 37, pp. 148–158 (1996).
Peffley et al., Biochem. Pharmacol 56, pp. 439–449 (1998).
Nelson et al., J. Biol. Chem. 256, pp. 1067–1068 (1981).
Spencer et al., J. Biol. Chem. 260, pp. 13391–13394 (1985).
Panini et al., J. Lipid Research 27, pp. 1190–1204 (1986).
Ness et al., Arch. Biochem. Biophys. 308, pp. 420–425 (1994).
Janowski et al., Proc. Natl. Acad. Sci. USA 96, pp. 266–271 (1999).
Venkateswaran et al., J. Biol. Chem. 275, pp. 14700–14707 (2000).
Costet et al., J. Biol. Chem. 275, pp. 28240–28245 (2000).
Ordovas et al., Nutr. Rev. 58, pp. 76–79 (2000).
Schmitz et al., Front. Biosci 6, D505–D514 (2001).
Tobin et al., Mol. Endocrinol. 14, pp. 741–752 (2000).
Marshall et al., J. Org. Chem. 61(17), pp. 5729–5735 (1996).
Baker et al., J. Chem. Soc. Perkin Trans. 1, pp. 1415–1421 (1990).
Belostotskii et al., Tetrahedron Letters 35(28), pp. 5075–5076 (1994).
Bartlett et al., J. Am. Chem. soc. 106(25), pp. 7854–7860 (1984).
Cooper et al., Synthesis (4), pp. 621–625 (2001).
Stara et al., Collect. Czech. Chem. Commun. 64(4), pp. 649–672 (1999).

*Primary Examiner*—Joseph K. McKane
(74) *Attorney, Agent, or Firm*—George W. Johnston; John P. Parise

(57) ABSTRACT

The present invention relates to novel dihydroindole and tetrahydroquinoline derivatives and pharmaceutically acceptable salts and/or pharmaceutically acceptable esters thereof. The compounds are useful for the treatment and/or prophylaxis of diseases which are associated with 2,3-oxidosqualene-lanosterol cyclase such as hypercholesterolemia, hyperlipemia, arteriosclerosis, vascular diseases, mycoses, gallstones, tumors and/or hyperproliferative disorders, and treatment and/or prophylaxis of impaired glucose tolerance and diabetes.

53 Claims, No Drawings

DIHYDROINDOLE AND TETRAHYDROQUINOLINE DERIVATIVES

FIELD OF THE INVENTION

The present invention is concerned with novel dihydroindole and tetrahydroquinoline derivatives, their manufacture and their use as medicaments.

BACKGROUND OF THE INVENTION 2,3-oxidosqualene-lanosterol cyclase (EC 5.4.99.) is required for the biosynthesis of cholesterol, ergosterol and other sterols. Causal risk factors that directly promote the development of coronary and peripheral atherosclerosis include elevated low-density lipoprotein cholesterol (LDL-C), low high-density lipoprotein cholesterol (HDL-C), hypertension, cigarette smoking and diabetes mellitus. Other synergistic risk factors include elevated concentrations of triglyceride (TG)-rich lipoproteins, small, dense low-density lipoprotein particles, lipoprotein (a) (Lp(a)), and homocysteine. Predisposing risk factors modify the causal or conditional risk factors and thus affect atherogenesis indirectly. The predisposing risk factors are obesity, physical inactivity, family history of premature CVD, and male sex. The strong connection between coronary heart disease (CHD) and high LDL-C levels in plasma, and the therapeutic advantage of lowering elevated LDL-C levels are now well established (Gotto et al., Circulation 81, 1990, 1721–1733; Stein et al., Nutr. Metab. Cardiovasc. Dis. 2, 1992, 113–156; Illingworth, Med. Clin. North. Am. 84, 2000, 23–42). Cholesterol-rich, sometimes unstable, atherosclerotic plaques lead to the occlusion of blood vessels resulting in an ischemia or an infarct. Studies with respect to primary prophylaxis have shown that a lowering of plasma LDL-C levels in plasma reduces the frequency of non-fatal incidences of CHD, while the overall morbidity remains unchanged. The lowering of plasma LDL-C levels in patients with pre-established CHD (secondary intervention) reduces CHD mortality and morbidity; meta-analysis of different studies shows that this decrease is proportional to the reduction of the LDL-C (Ross et al., Arch. Intern. Med. 159, 1999, 1793–1802).

The clinical advantage of cholesterol lowering is greater for patients with pre-established CHD than for asymptomatic persons with hypercholesterolemia. According to current guidelines, cholesterol lowering treatment is recommended for patients who had survived a myocardial infarct or patients suffering from angina pectoris or another atherosclerotic disease, with a target LDL-C level of 100 mg/dl.

Preparations such as bile acid sequestrants, fibrates, nicotinic acid, probucol as well as statins, i.e. HMG-Co-A reductase inhibitors such as simvastatin and atorvastatin, are used for usual standard therapies. The best statins reduce plasma LDL-C effectively by at least 40%, and also plasma triglycerides, a synergistic risk factor, but less effectively. In contrast, fibrates reduce plasma triglycerides effectively, but not LDL-C. Combination of a statin and a fibrate proved to be very efficacious in lowering LDL-C and triglycerides (Ellen and McPherson, J. Cardiol. 81, 1998, 60B–65B), but safety of such a combination remains an issue (Shepherd, Eur. Heart J. 16, 1995, 5–13). A single drug with a mixed profile combining effective lowering of both LDL-C and triglycerides would provide additional clinical benefit to asymptomatic and symptomatic patients.

In humans, statins are well tolerated at standard dosage, but reductions in non-sterol intermediates in the cholesterol synthesis pathway, such as isoprenoids and coenzyme Q, may be associated with adverse clinical events at high doses (Davignon et al., Can. J. Cardiol. 8, 1992, 843–864; Pederson and Tobert, Drug Safety 14, 1996, 11–24).

This has stimulated the search for, and development of compounds that inhibit cholesterol biosynthesis, yet act distal to the synthesis of these important, non-sterol intermediates. 2,3-oxidosqualene:lanosterol cyclase (OSC), a microsomal enzyme, represents a unique target for a cholesterol-lowering drug (Morand et al., J. Lipid Res., 38, 1997, 373–390; Mark et al., J. Lipid Res. 37, 1996, 148–158). OSC is downstream of farnesyl-pyrophosphate, beyond the synthesis of isoprenoids and coenzyme Q. In hamsters, pharmacologically active doses of an OSC inhibitor showed no adverse side-effects, in contrast to a statin which reduced food-intake and body weight, and increased plasma bilirubin, liver weight and liver triglyceride content (Morand et al., J. Lipid Res., 38, 1997, 373–390). The compounds described in European Patent Application No. 636 367, which inhibit OSC and which lower the total cholesterol in plasma, belong to these substances.

OSC inhibition does not trigger the overexpression of HMGR because of an indirect, negative feed-back regulatory mechanism involving the production of 24(S),25-epoxycholesterol (Peffley et al., Biochem. Pharmacol. 56, 1998, 439–449; Nelson et al., J. Biol. Chem. 256, 1981, 1067–1068; Spencer et al., J. Biol. Chem. 260, 1985, 13391–13394; Panini et al., J. Lipid Res. 27, 1986, 1190–1204; Ness et al., Arch. Biochem. Biophys. 308, 1994, 420–425). This negative feed-back regulatory mechanism is fundamental to the concept of OSC inhibition because (i) it potentiates synergistically the primary inhibitory effect with an indirect down-regulation of HMGR, and (ii) it prevents the massive accumulation of the precursor monooxidosqualene in the liver. In addition, 24(S),25-epoxycholesterol was found to be one of the most potent agonists of the nuclear receptor LXR (Janowski et al., Proc. Natl. Acad. Sci. USA, 96, 1999, 266–271). Considering that 24(S),25-epoxycholesterol is a by-product of inhibition of OSC it is hypothesized that the OSC inhibitors of the present invention could also indirectly activate LXR-dependent pathways such as (i) cholesterol-7alpha-hydroxylase to increase the consumption of cholesterol via the bile acid route, (ii) expression of ABC proteins with the potential to stimulate reverse cholesterol transport and increase plasma HDL-C levels (Venkateswaran et al., J. Biol. Chem. 275, 2000, 14700–14707; Costet et al., J. Biol. Chem. June 2000, in press; Ordovas, Nutr Rev 58, 2000, 76–79, Schmitz and Kaminsky, Front Biosci 6, 2001, D505–D514), and/or inhibit intestinal cholesterol absorption (Mangelsdorf, XIIth International Symposium on Atherosclerosis, Stockholm, June 2000). In addition, possible cross talks between fatty acid and cholesterol metabolism mediated by liver LXR have been hypothesized (Tobin et al., Mol. Endocrinol. 14, 2000, 741–752).

SUMMARY OF THE INVENTION

The invention relates to compounds of the formula (I)

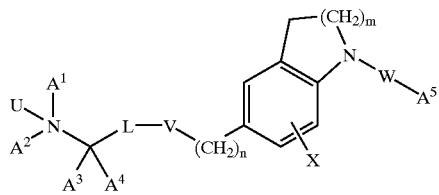

wherein
U is O or a lone pair,
V is a) O, S, $NR^1$, or $CH_2$, and L is lower-alkylene or lower-alkenylene,
b) —CH═CH— or —C≡C—, and L is lower-alkylene or a single bond,
W is CO, COO, $CONR^2$, CSO, $CSNR^2$, $SO_2$, or $SO_2NR^2$,
X is hydrogen or one or more optional halogen and/or lower-alkyl substituents,
m is 1 or 2,
n is 0 to 7,
$A^1$ is hydrogen, lower-alkenyl, or lower-alkyl optionally substituted by hydroxy, lower-alkoxy, or thio-lower-alkoxy,
$A^2$ is cycloalkyl, cycloalkyl-lower-alkyl, lower-alkenyl, lower-alkinyl, or lower-alkyl optionally substituted by hydroxy, lower-alkoxy or thio-lower-alkoxy,
$A^3$ and $A^4$ independently from each other are hydrogen or lower-alkyl, or
$A^1$ and $A^2$ or $A^1$ and $A^3$ are bonded to each other to form a ring and —$A^1$—$A^2$— or —$A^1$—$A^3$— are lower-alkylene or lower-alkenylene, optionally substituted by $R^3$, in which one —$CH_2$— group of —$A^1$-$A^2$— or —$A^1$—$A^3$— can optionally be replaced by $NR^4$, S, or O,
$A^5$ is cycloalkyl, cycloalkyl-lower-alkyl, heterocycloalkyl-lower-alkyl, aryl, aryl-lower-alkyl, heteroaryl, heteroaryl-lower-alkyl, lower-alkyl optionally substituted with hydroxy or lower-alkoxy, alkenyl optionally substituted with hydroxy, or alkadienyl optionally substituted with hydroxy,
$R^3$ is hydroxy, lower-alkoxy, thio-lower-alkoxy, $N(R^5, R^6)$, or lower-alkyl optionally substituted by hydroxy,
$R^1$, $R^2$, $R^4$, $R^5$, and $R^6$ independently from each other are hydrogen or lower-alkyl, and pharmaceutically acceptable salts and/or pharmaceutically acceptable esters thereof.

The compounds of formula I inhibit OSC and therefore also inhibit the biosynthesis of cholesterol, ergosterol and other sterols, and reduce the plasma cholesterol levels. They can therefore be used in the therapy and prophylaxis of hypercholesterolemia, hyperlipemia, arteriosclerosis and vascular diseases in general. Furthermore, they can be used in the therapy and/or prevention of mycoses, parasite infections, gallstones, cholestatic liver disorders, tumors and hyperproliferative disorders, e.g. hyperproliferative skin and vascular disorders. In addition, it has unexpectedly been found that the compounds of the present invention can also be of therapeutical use to improve glucose tolerance in order to treat and/or prevent related diseases such as diabetes. The compounds of the present invention further exhibit improved pharmacological properties compared to known compounds.

DETAILED DESCRIPTION OF THE INVENTION

Unless otherwise indicated the following definitions are set forth to illustrate and define the meaning and scope of the various terms used to describe the invention herein.

In this specification the term "lower" is used to mean a group consisting of one to seven, preferably of one to four carbon atom(s).

The term "lone pair" refers to an unbound electron pair, in particular to the unbound electron pair of a nitrogen atom in e.g. an amine.

The term "halogen" refers to fluorine, chlorine, bromine and iodine, with fluorine, chlorine and bromine being preferred.

The term "protecting group" refers to groups such as acyl, azoyl, alkoxycarbonyl, aryloxycarbonyl, or silyl. Examples are e.g. t-butyloxycarbonyl, benzyloxycarbonyl or fluorenylmethyloxycarbonyl which can be used for the protection of amino groups or trimethylsilyl, dimethyl-tert-butyl-silyl or tert.-butyl-diphenyl-silyl, which can be used for the protection of hydroxy groups, trityl or p-methoxybenzyl for sulfur, methyl or benzyl for the protection of phenole derivatives, methyl, ethyl or tert.-butyl for the protection of thiophenole derivatives.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups. Alkyl groups can be substituted e.g. with halogen, hydroxy, lower-alkoxy, thio-lower-alkoxy, lower-alkoxy-carbonyl, $NH_2$, and/or $N(lower-alkyl)_2$.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like. A lower-alkyl group may have a substitution pattern as described earlier in connection with the term "alkyl".

The term "cycloalkyl" refers to a monovalent carbocyclic radical of 3 to 10 carbon atom(s), preferably 3 to 6 carbon atoms, such as cyclopropyl, cyclobutyl, cyclopentyl, or cyclohexyl. Cycloalkyl in which one or more —$CH_2$— group is replaced by O, S, NH and/or N(lower-alkyl) are referred to as "heterocycloalkyl". Examples of heterocycloalkyl groups are e.g. tetrahydrofuryl, pyrrolidinyl, piperidyl, and morpholinyl.

The term "alkoxy" refers to the group R'—O—, wherein R' is an alkyl. The term "lower-alkoxy" refers to the group R'—O—, wherein R' is a lower-alkyl. The term "thio-alkoxy" refers to the group R'—S—, wherein R' is an alkyl. The term "thio-lower-alkoxy" refers to the group R'—S—, wherein R' is a lower-alkyl.

The term "alkenyl", alone or in combination with other groups, stands for a straight-chain or branched hydrocarbon residue comprising an olefinic bond and up to 20, preferably up to 16 carbon atoms, more preferrably up to 10 carbon atoms. Lower-alkenyl groups as described below also are preferred alkenyl groups. The term "lower-alkenyl" refers to a straight-chain or branched hydrocarbon residue comprising an olefinic bond and up to 7, preferably up to 4 carbon atoms, such as e.g. 2-propenyl. An alkenyl or lower-alkenyl group may have a substitution pattern as described earlier in connection with the term "alkyl".

The term "alkadienyl", alone or in combination with other groups, stands for a straight-chain or branched hydrocarbon residue comprising 2 olefinic bonds and up to 20, preferably up to 16 carbon atoms, more preferably up to 10 carbon atoms. Lower-alkadienyl groups as described below also are preferred alkadienyl groups. The term "lower-alkadienyl" refers to a straight-chain or branched hydrocarbon residue comprising 2 olefinic bonds and up to 7 carbon atoms. An alkadienyl or lower-alkadienyl group may have a substitution pattern as described earlier in connection with the term "alkyl".

The term "alkinyl", alone or in combination with other groups, stands for a straight-chain or branched hydrocarbon residue comprising a triple bond and up to 20, preferably up to 16 carbon atoms. The term "lower-alkinyl" refers to a straight-chain or branched hydrocarbon residue comprising a triple bond and up to 7, preferably up to 4 carbon atoms, such as e.g. 2-propinyl. An alkinyl or lower-alkinyl group may have a substitution pattern as described earlier in connection with the term "alkyl".

The term "alkylene" refers to a straight chain or branched divalent saturated aliphatic hydrocarbon group of 1 to 20 carbon atoms, preferably 1 to 16 carbon atoms. The term "lower-alkylene" refers to a straight chain or branched divalent saturated aliphatic hydrocarbon group of 1 to 7, preferably 1 to 6 or 3 to 6 carbon atoms. Straight chain alkylene or lower-alkylene groups are preferred. An alkylene or lower-alkylene group may have a substitution pattern as described earlier in connection with the term "alkyl".

The term "alkenylene" refers to a straight chain or branched divalent hydrocarbon group comprising an olefinic bond and up to 20 carbon atoms, preferably up to 16 carbon atoms. The term "lower-alkenylene" refers to a straight chain or branched divalent hydrocarbon group comprising an olefinic bond and up to 7, preferably up to 5, C-atoms. Straight chain alkenylene or lower-alkenylene groups are preferred. An alkenylene or lower-alkenylene group may have a substitution pattern as described earlier in connection with the term "alkyl".

The term "aryl" relates to the phenyl or naphthyl group, preferably the phenyl group, which can optionally be mono- or multiply-substituted by lower-alkyl, lower-alkinyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylcarbonyl, lower-alkylcarbonyloxy, lower-alkoxycarbonyl, aryl, and/or aryloxy. Preferred substituents are halogen, $CF_3$, $NO_2$, CN, lower-alkyl, lower-alkoxy, thio-lower-alkoxy, lower-alkoxycarbonyl, and/or lower-alkylcarbonyl. More preferred substituents are fluorine and chlorine.

The term "heteroaryl" refers to an aromatic 5- or 6-membered ring which can comprise 1, 2 or 3 atoms selected from nitrogen, oxygen and/or sulphur such as furyl, pyridyl, 1,2-, 1,3- and 1,4-diazinyl, thienyl, isoxazolyl, oxazolyl, imidazolyl, or pyrrolyl. The term "heteroaryl" further refers to bicyclic aromatic groups comprising two 5- or 6-membered rings, in which one or both rings can contain 1, 2 or 3 atoms selected from nitrogen, oxygen or sulphur such as e.g. indol or chinolin, or partially hydrogenated bicyclic aromatic groups such as e.g. indolinyl. A heteroaryl group may have a substitution pattern as described earlier in connection with the term "aryl". Preferred heteroaryl groups are thienyl and pyridyl which can optionally be substituted as described above, preferably with bromine.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, p-toluenesulphonic acid and the like, which are non toxic to living organisms. Preferred salts are formates, hydrochlorides, hydrobromides and methanesulfonic acid salts.

The term "pharmaceutically acceptable esters" embraces esters of the compounds of formula (I), in which hydroxy groups have been converted to the corresponding esters with inorganic or organic acids such as nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

In detail, the present invention relates to compounds of formula (I)

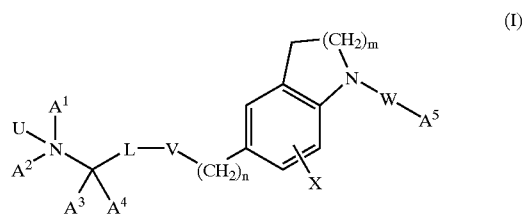

wherein
U is O or a lone pair,
V is a) O, S, $NR^1$, or $CH_2$, and L is lower-alkylene or lower-alkenylene,
b) —CH=CH— or —C≡C—, and L is lower-alkylene or a single bond,
W is CO, COO, $CONR^2$, CSO, $CSNR^2$, $SO_2$, or $SO_2NR^2$,
X is hydrogen or one or more optional halogen and/or lower-alkyl substituents,
m is 1 or 2,
n is 0 to 7,
$A^1$ is hydrogen, lower-alkenyl, or lower-alkyl optionally substituted by hydroxy, lower-alkoxy, or thio-lower-alkoxy,
$A^2$ is cycloalkyl, cycloalkyl-lower-alkyl, lower-alkenyl, lower-alkinyl, or lower-alkyl optionally substituted by hydroxy, lower-alkoxy or thio-lower-alkoxy,
$A^3$ and $A^4$ independently from each other are hydrogen or lower-alkyl, or
$A^1$ and $A^2$ or $A^1$ and $A^3$ are bonded to each other to form a ring and —$A^1$—$A^2$— or
—$A^1$—$A^3$— are lower-alkylene or lower-alkenylene, optionally substituted by $R^3$, in which one —$CH_2$— group of —$A^1$—$A^2$— or —$A^1$—$A^3$— can optionally be replaced by $NR^4$, S, or O,
$A^5$ is cycloalkyl, cycloalkyl-lower-alkyl, heterocycloalkyl-lower-alkyl, aryl, aryl-lower-alkyl, heteroaryl, heteroaryl-lower-alkyl, lower-alkyl optionally substituted with hydroxy or lower-alkoxy, alkenyl optionally substituted with hydroxy, or alkadienyl optionally substituted with hydroxy,
$R^3$ is hydroxy, lower-alkoxy, thio-lower-alkoxy, N($R^5$, $R^6$), or lower-alkyl optionally substituted by hydroxy,
$R^1$, $R^2$, $R^4$, $R^5$, and $R^6$ independently from each other are hydrogen or lower-alkyl, and pharmaceutically acceptable salts and/or pharmaceutically acceptable esters thereof.

Preferred are compounds of formula (I) and/or pharmaceutically acceptable salts thereof. Other preferred embodiments relate to compounds of formula (I) wherein U is a lone pair or to compounds of formula (I) wherein U is O.

Each of the definitions of V given above, a) and b), individually constitutes a preferred embodiment of the present invention. Further, each of the definitions of L, lower-alkylene, lower-alkenylene and a single bond, individually constitutes a preferred embodiment of the present invention. Compounds as described above in which V is O or $CH_2$ and L is lower-alkylene or lower-alkenylene relate to a further preferred embodiment of the present invention. Other preferred compounds are those, wherein V is —C≡C— and L is lower-alkylene or a single bond. Compounds as described above, wherein n is 0 also relate to a preferred embodiment of the present invention. Compounds as decsribed above, in which the number of carbon atoms of L and $(CH_2)_o$ together is 10 or less, more preferably 7 or less, are also preferred. The groups of compounds as described above, in which m is 1 or m is 2 individually relate to a preferred embodiment of the present invention.

Other preferred compounds of the present invention are those in which $A^1$ represents lower-alkyl, preferrably those in which $A^1$ is methyl or ethyl. Another group of preferred compounds of the present invention are those in which $A^2$ represents lower-alkenyl, or lower-alkyl optionally substituted by hydroxy or lower-alkoxy, with those compounds wherein $A^2$ represents 2-propenyl or 2-hydroxy-ethyl being especially preferred.

Compounds of formula (I), wherein $A^1$ and $A^2$ are bonded to each other to form a ring and —$A^1$—$A^2$— is lower-alkylene or lower-alkenylene, optionally substituted by $R^3$, in which one —$CH_2$— group of —$A^1$—$A^2$— can optionally be replaced by $NR^4$, S, or O, wherein $R^3$ and $R^4$ are as defined above are also preferred. In compounds wherein $A^1$ and $A^2$ are bonded to each other to form a ring, said ring is preferrably a 4-, 5-, or 6-membered ring such as e.g. piperidinyl or pyrrolidinyl.

A further preferred embodiment of the present invention relates to compounds of formula (I), wherein $A^3$ and/or $A^4$ represent hydrogen.

Compounds of formula (I), wherein $A^5$ cycloalkyl, cycloalkyl-lower-alkyl, heterocycloalkyl-lower-alkyl, aryl, aryl-lower-alkyl, heteroaryl, heteroaryl-lower-alkyl, or lower-alkyl optionally substituted with hydroxy or lower-alkoxy represent a preferred embodiment of the present invention. Other preferred compounds are those in which $A^5$ is phenyl or benzyl, optionally substituted by 1 to 3 substituents independently selected from the group consisting of fluorine and chlorine, or wherein $A^5$ is lower-alkyl, with those compounds wherein $A^5$ is phenyl, 4-fluoro-phenyl, 4-chloro-phenyl, butyl, or pentyl being particularly preferred. Another preferred group relates to compounds wherein X is hydrogen. Another preferred group relates to compounds wherein X is fluorine.

Compounds in which $R^2$ is hydrogen are also preferred. A further preferred embodiment of the present invention relates to those compounds as defined above, wherein W is COO, $CONR^2$, CSO, or $CSNR^2$ and $R^2$ is hydrogen.

Preferred compounds of general formula (I) are those selected from the group consisting of:

5-[5-(Allyl-methyl-amino)-pentyl]-2,3-dihydro-indole-1-carboxylic acid tert-butyl ester,
5-[5-(Allyl-methyl-amino)-pentyl]-2,3-dihydro-indole-1-carboxylic acid 4-chloro-phenyl ester,
5-[5-(Allyl-methyl-amino)-pentyl]-2,3-dihydro-indole-1-carboxylic acid (2,4-difluoro-phenyl)-amide,
5-[5-(Allyl-methyl-amino)-pentyl]-2,3-dihydro-indole-1-carboxylic acid (4-fluoro-phenyl)-amide,
5-[5-(Allyl-methyl-amino)-pentyl]-2,3-dihydro-indole-1-carboxylic acid p-tolylamide,
5-[5-(Allyl-methyl-amino)-pentyl]-2,3-dihydro-indole-1-carboxylic acid (4-bromo-phenyl)-amide,
5-[5-(Allyl-methyl-amino)-pentyl]-2,3-dihydro-indole-1-carboxylic acid (2,4-dimethoxy-phenyl)-amide,
5-[5-(Allyl-methyl-amino)-pentyl]-2,3-dihydro-indole-1-carboxylic acid (4-methoxy-phenyl)-amide,
5-[5-(Allyl-methyl-amino)-pentyl]-2,3-dihydro-indole-1-carboxylic acid naphthalen-2-ylamide,
5-[5-(Allyl-methyl-amino)-pentyl]-2,3-dihydro-indole-1-carboxylic acid (4-acetyl-phenyl)-amide,
{5-[5-(Allyl-methyl-amino)-pentyl]-2,3-dihydro-indol-1-yl}-(4-bromo-phenyl)-methanone,
3-{5-[5-(Allyl-methyl-amino)-pentyl]-2,3-dihydro-indole-1-carbonyl}-benzonitrile,
{5-[5-(Allyl-methyl-amino)-pentyl]-2,3-dihydro-indol-1-yl}-(4-fluoro-phenyl)-methanone,
{5-[5-(Allyl-methyl-amino)-pentyl]-2,3-dihydro-indol-1-yl}-(5-bromo-thiophen-2-yl)-methanone,
{5-[5-(Allyl-methyl-amino)-pentyl]-2,3-dihydro-indol-1-yl}-(4-chloro-phenyl)-methanone,
{5-[5-(Allyl-methyl-amino)-pentyl]-2,3-dihydro-indol-1-yl}-phenyl-methanone,
5-[5-(Allyl-methyl-amino)-pentyl]-2,3-dihydro-indole-1-carbothioic acid (4-chloro-phenyl)-amide,
5-[5-(Allyl-methyl-amino)-pentyl]-2,3-dihydro-indole-1-carbothioic acid cycloheptylamide,
5-[5-(Allyl-methyl-amino)-pentyl]-2,3-dihydro-indole-1-carbothioic acid cyclohexylmethyl-amide,
5-[5-(Allyl-methyl-amino)-pentyl]-2,3-dihydro-indole-1-carbothioic acid 4-chloro-benzylamide,
5-[5-(Allyl-methyl-amino)-pentyl]-2,3-dihydro-indole-1-carbothioic acid (4-trifluoromethyl-phenyl)-amide,
5-[5-(Allyl-methyl-amino)-pentyl]-2,3-dihydro-indole-1-carbothioic acid 4-fluoro-benzylamide,
5-[5-(Allyl-methyl-amino)-pentyl]-2,3-dihydro-indole-1-carbothioic acid O-(4-fluoro-phenyl)ester,
5-[5-(Allyl-methyl-amino)-pentyl]-2,3-dihydro-indole-1-carbothioic acid O-(4-chloro-phenyl)ester,
5-[5-(Allyl-methyl-amino)-pentyl]-2,3-dihydro-indole-1-carbothioic acid O-p-tolyl ester,
5-[5-(Allyl-methyl-amino)-pentyl]-2,3-dihydro-indole-1-carbothioic acid O-phenyl ester,
5-[5-(Allyl-methyl-amino)-pentyl]-2,3-dihydro-indole-1-sulfonic acid phenylamide,
5-[5-(Allyl-methyl-amino)-pentyl]-2,3-dihydro-indole-1-sulfonic acid (4-chloro-phenyl)-amide,
5-[5-(Allyl-methyl-amino)-pentyl]-2,3-dihydro-indole-1-sulfonic acid (2,4-difluoro-phenyl)-amide,
5-[5-(Allyl-methyl-amino)-pentyl]-2,3-dihydro-indole-1-sulfonic acid (4-fluoro-phenyl)-amide,
5-[4-(Allyl-methyl-amino)-butoxy]-2,3-dihydro-indole-1-carboxylic acid 4-chloro-phenyl ester,
5-[4-(Allyl-methyl-amino)-butoxy]-2,3-dihydro-indole-1-carboxylic acid (2,4-difluoro-phenyl)-amide,
5-[4-(Allyl-methyl-amino)-butoxy]-2,3-dihydro-indole-1-carboxylic acid (4-fluoro-phenyl)-amide,
5-[4-(Allyl-methyl-amino)-butoxy]-2,3-dihydro-indole-1-carboxylic acid p-tolylamide,
5-[4-(Allyl-methyl-amino)-butoxy]-2,3-dihydro-indole-1-carboxylic acid (4-bromo-phenyl)-amide,
5-[4-(Allyl-methyl-amino)-butoxy]-2,3-dihydro-indole-1-carboxylic acid (2,4-dimethoxy-phenyl)-amide,
5-[4-(Allyl-methyl-amino)-butoxy]-2,3-dihydro-indole-1-carboxylic acid (4-methoxy-phenyl)-amide, 5-[4-(Allyl-methyl-amino)-butoxy]-2,3-dihydro-indole-1-carboxylic acid naphthalen-2-ylamide,
5-[4-(Allyl-methyl-amino)-butoxy]-2,3-dihydro-indole-1-carboxylic acid (4-acetyl-phenyl)-amide,
{5-[4-(Allyl-methyl-amino)-butoxy]-2,3-dihydro-indol-1-yl}-(4-bromo-phenyl)-methanone,
3-{5-[4-(Allyl-methyl-amino)-butoxy]-2,3-dihydro-indole-1-carbonyl}-benzonitrile,
{5-[4-(Allyl-methyl-amino)-butoxy]-2,3-dihydro-indol-1-yl}-(4-fluoro-phenyl)-methanone,
{5-[4-(Allyl-methyl-amino)-butoxy]-2,3-dihydro-indol-1-yl}-(5-bromo-thiophen-2-yl)-methanone,
{5-[4-(Allyl-methyl-amino)-butoxy]-2,3-dihydro-indol-1-yl}-(4-chloro-phenyl)-methanone,
{5-[4-(Allyl-methyl-amino)-butoxy]-2,3-dihydro-indol-1-yl}-phenyl-methanone,
{5-[4-(Allyl-methyl-amino)-butoxy]-2,3-dihydro-indol-1-yl}-(4-trifluoromethyl-phenyl)-methanone,
5-[4-(Allyl-methyl-amino)-butoxy]-2,3-dihydro-indole-1-carbothioic acid (4-chloro-phenyl)-amide,
5-[4-(Allyl-methyl-amino)-butoxy]-2,3-dihydro-indole-1-carbothioic acid cycloheptylamide,
5-[4-(Allyl-methyl-amino)-butoxy]-2,3-dihydro-indole-1-carbothioic acid cyclohexylmethyl-amide,
5-[4-(Allyl-methyl-amino)-butoxy]-2,3-dihydro-indole-1-carbothioic acid 4-chloro-benzylamide,
5-[4-(Allyl-methyl-amino)-butoxy]-2,3-dihydro-indole-1-carbothioic acid (4-trifluoromethyl-phenyl)-amide,
5-[4-(Allyl-methyl-amino)-butoxy]-2,3-dihydro-indole-1-carbothioic acid 4-fluoro-benzylamide,
5-[4-(Allyl-methyl-amino)-butoxy]-2,3-dihydro-indole-1-carbothioic acid benzylamide,
5-[4-(Allyl-methyl-amino)-butoxy]-2,3-dihydro-indole-1-carbothioic acid cyclohexylamide,
5-[4-(Allyl-methyl-amino)-butoxy]-2,3-dihydro-indole-1-carbothioic acid O-(4-chloro-phenyl)ester,
5-{4-[(2-Methoxy-ethyl)-methyl-amino]-butoxy}-2,3-dihydro-indole-1-carbothioic acid O-(4-chloro-phenyl) ester,
5-{4-[Ethyl-(2-hydroxy-ethyl)-amino]-butoxy}-2,3-dihydro-indole-1-carbothioic acid O-(4-chloro-phenyl) ester,
5-[4-(Allyl-methyl-amino)-butoxy]-2,3-dihydro-indole-1-carbothioic acid O-(4-fluoro-phenyl)ester,
Allyl-{5-[1-(4-chloro-benzenesulfonyl)-1,2,3,4-tetrahydro-quinolin-6-yl]-pentyl}methyl-amine,
Allyl-{5-[1-(4-bromo-benzenesulfonyl)-1,2,3,4-tetrahydro-quinolin-6-yl]-pentyl}-methyl-amine,
6-[4-(Allyl-methyl-amino)-but-2-enyloxy]-3,4-dihydro-2H-quinoline-1-carboxylic acid 4-chloro-phenyl ester,
6-[4-(Allyl-methyl-amino)-but-2-enyloxy]-3,4-dihydro-2H-quinoline-1-carboxylic acid tert-butyl ester,
6-[4-(Allyl-methyl-amino)-but-2-enyloxy]-3,4-dihydro-2H-quinoline-1-carboxylic acid ethyl ester,
Allyl-{4-[1-(4-chloro-benzenesulfonyl)-1,2,3,4-tetrahydro-quinolin-6-yloxy]-but-2-enyl}-methyl-amine,
6-[5-(Allyl-methyl-amino)-pentyloxy]-3,4-dihydro-2H-quinoline-1-carboxylic acid tert-butyl ester,
Allyl-{5-[1-(4-chloro-benzenesulfonyl)-1,2,3,4-tetrahydro-quinolin-6-yloxy]-pentyl}-methyl-amine,
6-[3-(Allyl-methyl-amino)-propoxy]-3,4-dihydro-2H-quinoline-1-carboxylic acid 4-chloro-phenyl ester,
6-[5-(Allyl-methyl-amino)-pentyloxy]-3,4-dihydro-2H-quinoline-1-carboxylic acid 4-chloro-phenyl ester,
6-[4-(Allyl-methyl-amino)-but-2-enyloxy]-3,4-dihydro-2H-quinoline-1-carboxylic acid (4-methoxy-phenyl)-amide,
6-[4-(Allyl-methyl-amino)-but-2-enyloxy]-3,4-dihydro-2H-quinoline-1-carboxylic acid p-tolylamide,
6-[4-(Allyl-methyl-amino)-but-2-enyloxy]-3,4-dihydro-2H-quinoline-1-carboxylic acid naphthalen-1-ylamide,
6-[4-(Allyl-methyl-amino)-but-2-enyloxy]-3,4-dihydro-2H-quinoline-1-carboxylic acid (2,4-difluoro-phenyl)-amide,
6-[4-(Allyl-methyl-amino)-but-2-enyloxy]-3,4-dihydro-2H-quinoline-1-carboxylic acid (4-fluoro-3-trifluoromethyl-phenyl)-amide,
6-[4-(Allyl-methyl-amino)-but-2-enyloxy]-3,4-dihydro-2H-quinoline-1-carboxylic acid (4-fluoro-phenyl)-amide,
6-[4-(Allyl-methyl-amino)-but-2-enyloxy]-3,4-dihydro-2H-quinoline-1-carboxylic acid (2,4-dimethoxy-phenyl)-amide,
6-[4-(Allyl-methyl-amino)-but-2-enyloxy]-3,4-dihydro-2H-quinoline-1-carboxylic acid (4-methylsulfanyl-phenyl)-amide,
6-[4-(Allyl-methyl-amino)-but-2-enyloxy]-3,4-dihydro-2H-quinoline-1-carboxylic acid (4-bromo-phenyl)-amide,
6-[4-(Allyl-methyl-amino)-but-2-enyloxy]-3,4-dihydro-2H-quinoline-1-carboxylic acid benzylamide,
6-[4-(Allyl-methyl-amino)-but-2-enyloxy]-3,4-dihydro-2H-quinoline-1-carboxylic acid (4-butyl-phenyl)-amide,
6-[4-(Allyl-methyl-amino)-but-2-enyloxy]-3,4-dihydro-2H-quinoline-1-carboxylic acid (4-acetyl-phenyl)-amide,
6-[6-(Allyl-methyl-amino)-hexyloxy]-3,4-dihydro-2H-quinoline-1-carboxylic acid 4-chloro-phenyl ester.
6-[4-(Allyl-methyl-amino)-butoxy]-3,4-dihydro-2H-quinoline-1-carboxylic acid 4-chloro-phenyl ester,
6-[6-(Allyl-methyl-amino)-hexyloxy]-3,4-dihydro-2H-quinoline-1-carboxylic acid p-tolylamide,
6-[6-(Allyl-methyl-amino)-hexyloxy]-3,4-dihydro-2H-quinoline-1-carboxylic acid (4-fluoro-phenyl)-amide,
6-[6-(Allyl-methyl-amino)-hexyloxy]-3,4-dihydro-2H-quinoline-1-carboxylic acid (4-bromo-phenyl)-amide,
6-[6-(Allyl-methyl-amino)-hexyloxy]-3,4-dihydro-2H-quinoline-1-carboxylic acid (4-butyl-phenyl)-amide,
6-[6-(Allyl-methyl-amino)-hexyloxy]-3,4-dihydro-2H-quinoline-1-carboxylic acid 4-bromo-phenyl ester,
6-[6-(Allyl-methyl-amino)-hexyloxy]-3,4-dihydro-2H-quinoline-1-carboxylic acid 4-fluoro-phenyl ester,
6-[6-(Allyl-methyl-amino)-hexyloxy]-3,4-dihydro-2H-quinoline-1-carboxylic acid p-tolyl ester,
6-[6-(Allyl-methyl-amino)-hexyloxy]-3,4-dihydro-2H-quinoline-1-carboxylic acid hexyl ester,
3-{6-[6-(Allyl-methyl-amino)-hexyloxy]-3,4-dihydro-2H-quinoline-1-carbonyl}-benzonitrile,
{6-[6-(Allyl-methyl-amino)-hexyloxy]-3,4-dihydro-2H-quinolin-1-yl}-(4-bromo-phenyl)-methanone,
{6-[6-(Allyl-methyl-amino)-hexyloxy]-3,4-dihydro-2H-quinolin-1-yl}-(5-bromo-thiophen-2-yl)-methanone,
{6-[6-(Allyl-methyl-amino)-hexyloxy]-3,4-dihydro-2H-quinolin-1-yl}-(4-fluoro-phenyl)-methanone,
6-[6-(Allyl-methyl-amino)-hexyloxy]-3,4-dihydro-2H-quinoline-1-carboxylic acid 4-methoxy-phenyl ester,
3-{6-[4-(Allyl-methyl-amino)-but-2-enyloxy]-3,4-dihydro-2H-quinoline-1-carbonyl}-benzonitrile,
{6-[4-(Allyl-methyl-amino)-but-2-enyloxy]-3,4-dihydro-2H-quinolin-1-yl}-(4-bromo-phenyl)-methanone,
1-{6-[4-(Allyl-methyl-amino)-but-2-enyloxy]-3,4-dihydro-2H-quinolin-1-yl}-2-(2,4-difluoro-phenyl)-ethanone,
1-(4-{6-[4-(Allyl-methyl-amino)-but-2-enyloxy]-3,4-dihydro-2H-quinoline-1-carbonyl}-phenyl)-ethanone,
{6-[4-(Allyl-methyl-amino)-but-2-enyloxy]-3,4-dihydro-2H-quinolin-1-yl}-(5-bromo-thiophen-2-yl)-methanone,
{6-[4-(Allyl-methyl-amino)-but-2-enyloxy]-3,4-dihydro-2H-quinolin-1-yl}-(3-chloro-phenyl)-methanone,
1-{6-[4-(Allyl-methyl-amino)-but-2-enyloxy]-3,4-dihydro-2H-quinolin-1-yl}-2-(4-fluoro-phenyl)-ethanone, {6-[4-(Allyl-methyl-amino)-but-2-enyloxy]-3,4-dihydro-2H-quinolin-1-yl}-(4-fluoro-phenyl)-methanone,
{6-[4-(Allyl-methyl-amino)-but-2-enyloxy]-3,4-dihydro-2H-quinolin-1-yl}-(4-chloro-phenyl)-methanone,
{6-[4-(Allyl-methyl-amino)-but-2-enyloxy]-3,4-dihydro-2H-quinolin-1-yl}-(4-trifluoromethyl-phenyl)-methanone,
{6-[4-(Allyl-methyl-amino)-but-2-enyloxy]-3,4-dihydro-2H-quinolin-1-yl}-pyridin-3-yl-methanone,
{6-[4-(Allyl-methyl-amino)-but-2-enyloxy]-3,4-dihydro-2H-quinolin-1-yl}-(4-fluoro-3-methyl-phenyl)-methanone,
6-[4-(allyl-methyl-amino)-but-2-enyloxy]-3,4-dihydro-2H-quinoline-1-carboxylic acid 4-nitro-phenyl ester,
6-[4-(Allyl-methyl-amino)-but-2-enyloxy]-3,4-dihydro-2H-quinoline-1-carboxylic acid hexyl ester,
6-[4-(Allyl-methyl-amino)-but-2-enyloxy]-3,4-dihydro-2H-quinoline-1-carboxylic acid 4-bromo-phenyl ester,
6-[4-(Allyl-methyl-amino)-but-2-enyloxy]-3,4-dihydro-2H-quinoline-1-carboxylic acid isobutyl ester,
6-[4-(Allyl-methyl-amino)-but-2-enyloxy]-3,4-dihydro-2H-quinoline-1-carboxylic acid phenyl ester,
6-[4-(Allyl-methyl-amino)-but-2-enyloxy]-3,4-dihydro-2H-quinoline-1-carboxylic acid 4-methoxy-phenyl ester,
6-[4-(Allyl-methyl-amino)-but-2-enyloxy]-3,4-dihydro-2H-quinoline-1-carboxylic acid p-tolyl ester,
6-[4-(Allyl-methyl-amino)-but-2-enyloxy]-3,4-dihydro-2H-quinoline-1-carboxylic acid 4-methoxycarbonyl-phenyl ester,
6-[4-(Allyl-methyl-amino)-but-2-enyloxy]-3,4-dihydro-2H-quinoline-1-carboxylic acid butyl ester,
6-[4-(Allyl-methyl-amino)-but-2-enyloxy]-3,4-dihydro-2H-quinoline-1-carboxylic acid 4-fluoro-phenyl ester,
6-[4-(Allyl-methyl-amino)-but-2-enyloxy]-3,4-dihydro-2H-quinoline-1-carboxylic acid phenethyl-amide,
6-(4-Diethylamino-butoxy)-3,4-dihydro-2H-quinoline-1-carboxylic acid 4-chloro-phenyl ester,
6-(4-Diethylamino-butoxy)-3,4-dihydro-2H-quinoline-1-carboxylic acid benzyl ester,
6-(4-Diethylamino-butoxy)-3,4-dihydro-2H-quinoline-1-carboxylic acid 4-bromo-phenyl ester,
6-(4-Diethylamino-butoxy)-3,4-dihydro-2H-quinoline-1-carboxylic acid hexyl ester,
6-(4-Diethylamino-butoxy)-3,4-dihydro-2H-quinoline-1-carboxylic acid (4-fluoro-phenyl)-amide,
6-(4-Diethylamino-butoxy)-3,4-dihydro-2H-quinoline-1-carboxylic acid p-tolylamide,
6-(4-Diethylamino-butoxy)-3,4-dihydro-2H-quinoline-1-carboxylic acid (4-bromo-phenyl)-amide,
6-[4-(Allyl-methyl-amino)-butoxy]-3,4-dihydro-2H-quinoline-1-carboxylic acid (2,4-difluoro-phenyl)-amide,
6-[4-(Allyl-methyl-amino)-butoxy]-3,4-dihydro-2H-quinoline-1-carboxylic acid (4-fluoro-phenyl)-amide,
6-[4-(Allyl-methyl-amino)-butoxy]-3,4-dihydro-2H-quinoline-1-carboxylic acid p-tolylamide,
6-[4-(Allyl-methyl-amino)-butoxy]-3,4-dihydro-2H-quinoline-1-carboxylic acid (4-bromo-phenyl)-amide,
6-[4-(Allyl-methyl-amino)-butoxy]-3,4-dihydro-2H-quinoline-1-carboxylic acid (2,4-dimethoxy-phenyl)-amide,
6-[4-(Allyl-methyl-amino)-butoxy]-3,4-dihydro-2H-quinoline-1-carboxylic acid (4-methoxy-phenyl)-amide,
6-[4-(Allyl-methyl-amino)-butoxy]-3,4-dihydro-2H-quinoline-1-carboxylic acid naphthalen-2-ylamide,
6-[4-(Allyl-methyl-amino)-butoxy]-3,4-dihydro-2H-quinoline-1-carboxylic acid (4-acetyl-phenyl)-amide,
6-(4-Diethylamino-butoxy)-3,4-dihydro-2H-quinoline-1-carboxylic acid 4-fluoro-phenyl ester,
{6-[4-(Allyl-methyl-amino)-butoxy]-3,4-dihydro-2H-quinolin-1-yl}-(4-bromo-phenyl)-methanone,
3-{6-[4-(Allyl-methyl-amino)-butoxy]-3,4-dihydro-2H-quinoline-1-carbonyl}-benzonitrile,
{6-[4-(Allyl-methyl-amino)-butoxy]-3,4-dihydro-2H-quinolin-1-yl}-(4-fluoro-phenyl)-methanone,
{6-[4-(Allyl-methyl-amino)-butoxy]-3,4-dihydro-2H-quinolin-1-yl}-(5-bromo-thiophen-2-yl)-methanone,
{6-[4-(Allyl-methyl-amino)-butoxy]-3,4-dihydro-2H-quinolin-1-yl}-(4-chloro-phenyl)-methanone,
{6-[4-(Allyl-methyl-amino)-butoxy]-3,4-dihydro-2H-quinolin-1-yl}-phenyl-methanone,
{6-[4-(Allyl-methyl-amino)-butoxy]-3,4-dihydro-2H-quinolin-1-yl}-(4-trifluoromethyl-phenyl)-methanone,
(4-Bromo-phenyl)-[6-(4-diethylamino-butoxy)-3,4-dihydro-2H-quinolin-1-yl]-methanone,
3-[6-(4-Diethylamino-butoxy)-3,4-dihydro-2H-quinoline-1-carbonyl]-benzonitrile,
[6-(4-Diethylamino-butoxy)-3,4-dihydro-2H-quinolin-1-yl]-(4-fluoro-phenyl)-methanone,
(5-Bromo-thiophen-2-yl)-[6-(4-diethylamino-butoxy)-3,4-dihydro-2H-quinolin-1-yl]-methanone,
6-[4-(Allyl-methyl-amino)-butoxy]-3,4-dihydro-2H-quinoline-1-carbothioic acid (4-chloro-phenyl)-amide,
6-[4-(Allyl-methyl-amino)-butoxy]-3,4-dihydro-2H-quinoline-1-carbothioic acid cycloheptylamide,
6-[4-(Allyl-methyl-amino)-butoxy]-3,4-dihydro-2H-quinoline-1-carbothioic acid cyclohexylmethyl-amide,
6-[4-(Allyl-methyl-amino)-butoxy]-3)4-dihydro-2H-quinoline-1-carbothioic acid 4-chloro-benzylamide,
6-[4-(Allyl-methyl-amino)-butoxy]-3,4-dihydro-2H-quinoline-1-carbothioic acid (4-trifluoromethyl-phenyl)-amide,
6-[4-(Allyl-methyl-amino)-butoxy]-3,4-dihydro-2H-quinoline-1-carbothioic acid 4-fluoro-benzylamide,
6-[4-(Allyl-methyl-amino)-butoxy]-3,4-dihydro-2H-quinoline-1-carbothioic acid benzylamide,
6-[4-(Allyl-methyl-amino)-butoxy]-3,4-dihydro-2H-quinoline-1-carbothioic acid cyclohexylamide,
6-(4-Diethylamino-butoxy)-3,4-dihydro-2H-quinoline-1-carbothioic acid O-(4-fluoro-phenyl) ester,
6-(4-Diethylamino-butoxy)-3,4-dihydro-2H-quinoline-1-carbothioic acid O-(4-chloro-phenyl) ester,
6-[4-(Allyl-methyl-amino)-butoxy]-3,4-dihydro-2H-quinoline-1-carbothioic acid O-(4-fluoro-phenyl) ester,
6-[4-(Allyl-methyl-amino)-butoxy]-3,4-dihydro-2H-quinoline-1-carbothioic acid O-(4-chloro-phenyl)ester,
6-[4-(Allyl-methyl-amino)-butoxy]-3,4-dihydro-2H-quinoline-1-carbothioic acid O-phenyl ester,
6-[4-(Allyl-methyl-amino)-butoxy]-3,4-dihydro-2H-quinoline-1-sulfonic acid phenylamide,
6-[4-(Allyl-methyl-amino)-butoxy]-3,4-dihydro-2H-quinoline-1-sulfonic acid (4-chloro-phenyl)-amide,
6-[4-(Allyl-methyl-amino)-butoxy]-3,4-dihydro-2H-quinoline-1-sulfonic acid (2,4-difluoro-phenyl)-amide,
6-[4-(Allyl-methyl-amino)-butoxy]-3,4-dihydro-2H-quinoline-1-sulfonic acid (4-fluoro-phenyl)-amide,
5-[4-(Allyl-methyl-amino)-butoxy]-2,3-dihydro-indole-1-sulfonic acid (4-chloro-phenyl)-amide,
5-[4-(Allyl-methyl-amino)-butoxy]-2,3-dihydro-indole-1-sulfonic acid p-tolylamide,
5-[4-(Allyl-methyl-amino)-butoxy]-2,3-dihydro-indole-1-sulfonic acid (4-cyano-phenyl)-amide,
5-[4-(Allyl-methyl-amino)-butoxy]-2,3-dihydro-indole-1-sulfonic acid (4-methoxy-phenyl)-amide,
5-[4-(Allyl-methyl-amino)-butoxy]-2,3-dihydro-indole-1-sulfonic acid (3,4-difluoro-phenyl)-amide, 5-[4-(Allyl-methyl-amino)-butoxy]-2,3-dihydro-indole-1-sulfonic acid (3-fluoro-phenyl)-amide,
5-[4-(Allyl-methyl-amino)-butoxy]-2,3-dihydro-indole-1-sulfonic acid (2,4-difluoro-phenyl)-amide,
5-[4-(Allyl-methyl-amino)-butoxy]-2,3-dihydro-indole-1-sulfonic acid (2,5-difluoro-phenyl)-amide,
5-[4-(Allyl-methyl-amino)-butoxy]-2,3-dihydro-indole-1-sulfonic acid (4-bromo-phenyl)-amide,
5-[4-(Allyl-methyl-amino)-butoxy]-2,3-dihydro-indole-1-sulfonic acid phenylamide,
5-[4-(Allyl-methyl-amino)-butoxy]-2,3-dihydro-indole-1-carbothioic acid (3-methyl-butyl)-amide,
5-[4-(Allyl-methyl-amino)-butoxy]-2,3-dihydro-indole-1-carbothioic acid (furan-2-ylmethyl)-amide,
5-[4-(Allyl-methyl-amino)-butoxy]-2,3-dihydro-indole-1-carbothioic acid ethylamide,
5-[4-(Allyl-methyl-amino)-butoxy]-2,3-dihydro-indole-1-carbothioic acid butylamide,
5-[4-(Allyl-methyl-amino)-butoxy]-2,3-dihydro-indole-1-carbothioic acid (2-methyl-butyl)-amide,
5-[4-(Allyl-methyl-amino)-butoxy]-2,3-dihydro-indole-1-carbothioic acid (2-methoxy-ethyl)-amide,
5-[4-(Allyl-methyl-amino)-butoxy]-2,3-dihydro-indole-1-carbothioic acid (4-butyl-phenyl)-amide,
5-[4-(Allyl-methyl-amino)-butoxy]-2,3-dihydro-indole-1-carbothioic acid (tetrahydro-furan-2-ylmethyl)-amide,
6-[4-(Allyl-methyl-amino)-but-2-enyloxy]-3,4-dihydro-2H-quinoline-1-sulfonic acid (4-chloro-phenyl)-amide,
6-[4-(Allyl-methyl-amino)-but-2-enyloxy]-3,4-dihydro-2H-quinoline-1-sulfonic acid (4-fluoro-phenyl)-amide,
6-[4-(Allyl-methyl-amino)-but-2-enyloxy]-3,4-dihydro-2H-quinoline-1-sulfonic acid (4-bromo-phenyl)-amide,
6-[4-(Allyl-methyl-amino)-but-2-enyloxy]-3,4-dihydro-2H-quinoline-1-sulfonic acid (p-tolyl)-amide,
6-[4-(Allyl-methyl-amino)-but-2-enyloxy]-3,4-dihydro-2H-quinoline-1-sulfonic acid (3,4-difluoro-phenyl)-amide,
6-[4-(Allyl-methyl-amino)-but-2-enyloxy]-3,4-dihydro-2H-quinoline-1-sulfonic acid (4-trifluoromethyl-phenyl)-amide,
6-[4-(Allyl-methyl-amino)-but-2-enyloxy]-3,4-dihydro-2H-quinoline-1-sulfonic acid (3-fluoro-phenyl)-amide,
6-[4-(Allyl-methyl-amino)-but-2-enyloxy]-3,4-dihydro-2H-quinoline-1-sulfonic acid (4-cyano-phenyl)-amide,
6-[4-(Allyl-methyl-amino)-but-2-enyloxy]-3,4-dihydro-2H-quinoline-1-sulfonic acid (2,4-difluoro-phenyl)-amide,
6-[4-(Allyl-methyl-amino)-but-2-enyloxy]-3,4-dihydro-2H-quinoline-1-sulfonic acid (4-methoxy-phenyl)-amide,
6-[4-(Allyl-methyl-amino)-but-2-enyloxy]-3,4-dihydro-2H-quinoline-1-sulfonic acid (2,5-difluoro-phenyl)-amide,
6-[4-(Allyl-methyl-amino)-but-2-enyloxy]-3,4-dihydro-2H-quinoline-1-sulfonic acid (phenyl)-amide,
6-[5-(Allyl-methyl-amino)-pentyloxy]-3,4-dihydro-2H-quinoline-1-sulfonic acid (4-chloro-phenyl)-amide,
6-[5-(Allyl-methyl-amino)-pentyloxy]-3,4-dihydro-2H-quinoline-1-sulfonic acid (4-cyano-phenyl)-amide,
6-[5-(Allyl-methyl-amino)-pentyloxy]-3,4-dihydro-2H-quinoline-1-sulfonic acid (3-fluoro-phenyl)-amide,
6-[5-(Allyl-methyl-amino)-pentyloxy]-3,4-dihydro-2H-quinoline-1-sulfonic acid (4-bromo-phenyl)-amide,
6-[5-(Allyl-methyl-amino)-pentyloxy]-3,4-dihydro-2H-quinoline-1-sulfonic acid (4-methoxy-phenyl)-amide,
6-[5-(Allyl-methyl-amino)-pentyloxy]-3,4-dihydro-2H-quinoline-1-sulfonic acid (2,4-difluoro-phenyl)-amide,
6-[5-(Allyl-methyl-amino)-pentyloxy]-3,4-dihydro-2H-quinoline-1-sulfonic acid p-tolylamide,
6-[5-(Allyl-methyl-amino)-pentyloxy]-3,4-dihydro-2H-quinoline-1-sulfonic acid (4-fluoro-phenyl)-amide,
6-[5-(Allyl-methyl-amino)-pentyloxy]-3,4-dihydro-2H-quinoline-1-sulfonic acid (2,5-difluoro-phenyl)-amide,
6-[5-(Allyl-methyl-amino)-pentyloxy]-3,4-dihydro-2H-quinoline-1-sulfonic acid (4-trifluoromethyl-phenyl)-amide,
6-[5-(Allyl-methyl-amino)-pentyloxy]-3,4-dihydro-2H-quinoline-1-sulfonic acid (3,4-difluoro-phenyl)-amide,
6-[6-(Allyl-methyl-amino)-hexyloxy]-3,4-dihydro-2H-quinoline-1-carbothioic acid (4-chloro-phenyl)-amide,
6-[6-(Allyl-methyl-amino)-hexyloxy]-3,4-dihydro-2H-quinoline-1-sulfonic acid (4-cyano-phenyl)-amide,
6-[6-(Allyl-methyl-amino)-hexyloxy]-3,4-dihydro-2H-quinoline-1-carbothioic acid cycloheptylamide,
6-[6-(Allyl-methyl-amino)-hexyloxy]-3,4-dihydro-2H-quinoline-1-sulfonic acid (4-methoxy-phenyl)-amide,
6-[6-(Allyl-methyl-amino)-hexyloxy]-3,4-dihydro-2H-quinoline-1-sulfonic acid (4-chloro-phenyl)-amide,
6-[6-(Allyl-methyl-amino)-hexyloxy]-3,4-dihydro-2H-quinoline-1-sulfonic acid (2,5-difluoro-phenyl)-amide,
6-[6-(Allyl-methyl-amino)-hexyloxy]-3,4-dihydro-2H-quinoline-1-sulfonic acid (4-bromo-phenyl)-amide,
6-[6-(Allyl-methyl-amino)-hexyloxy]-3,4-dihydro-2H-quinoline-1-sulfonic acid (2,4-difluoro-phenyl)-amide,
6-[6-(Allyl-methyl-amino)-hexyloxy]-3,4-dihydro-2H-quinoline-1-sulfonic acid p-tolylamide,
6-[6-(Allyl-methyl-amino)-hexyloxy]-3,4-dihydro-2H-quinoline-1-sulfonic acid butylamide,
6-[6-(Allyl-methyl-amino)-hexyloxy]-3,4-dihydro-2H-quinoline-1-sulfonic acid (3-fluoro-phenyl)-amide,
6-[6-(Allyl-methyl-amino)-hexyloxy]-3,4-dihydro-2H-quinoline-1-sulfonic acid phenylamide,
5-[4-(Allyl-methyl-amino)-but-2-enyloxy]-2,3-dihydro-indole-1-carboxylic acid tert-butyl ester,
5-[4-(Allyl-methyl-amino)-butoxy]-2,3-dihydro-indole-1-carboxylic acid tert-butyl ester,
5-{4-[(2-Methoxy-ethyl)-methyl-amino]-butoxy}-2,3-dihydro-indole-1-carboxylic acid tert-butyl ester,
5-{4-[Ethyl-(2-hydroxy-ethyl)-amino]-butoxy}-2,3-dihydro-indole-1-carboxylic acid tert-butyl ester,
6-[6-(Allyl-methyl-amino)-hexyloxy]-3,4-dihydro-2H-quinoline-1-carboxylic acid tert-butyl ester,
6-[4-(Allyl-methyl-amino)-butoxy]-3,4-dihydro-2H-quinoline-1-carboxylic acid tert-butyl ester,
6-(4-Diethylamino-butoxy)-3,4-dihydro-2H-quinoline-1-carboxylic acid tert-butyl ester, and
6-[5-(Allyl-methyl-amino)-pentyl]-3,4-dihydro-2H-quinoline-1-carboxylic acid tert-butyl ester
and pharmaceutically acceptable salts and/or pharmaceutically acceptable esters thereof.

Further preferred compounds of general formula (I) are those selected from the group consisting of 5-[5-(Allyl-methyl-amino)-pent-1-ynyl]-6-fluoro-2,3-dihydro-indole-1-carboxylic acid 4-chloro-phenyl ester,
6-Fluoro-5-{5-[(2-hydroxy-ethyl)-methyl-amino]-pent-1-ynyl}-2,3-dihydro-indole-1-carboxylic acid 4-chloro-phenyl ester,
5-{5-[Ethyl-(2-hydroxy-ethyl)-amino]-pent-1-ynyl}-6-fluoro-2,3-dihydro-indole-1-carboxylic acid 4-chloro-phenyl ester,
2-({5-[6-Fluoro-1-(toluene-4-sulfonyl)-2,3-dihydro-1H-indol-5-yl]-pent-4-ynyl}-methyl-amino)-ethanol,
2-(Ethyl-{5-[6-fluoro-1-(toluene-4-sulfonyl)-2,3-dihydro-1H-indol-5-yl]-pent-4-ynyl}-amino)-ethanol,
6-Fluoro-5-[5-(methyl-propyl-amino)-pentyl]-2,3-dihydro-indole-1-carboxylic acid phenyl ester, 2-({5-[6-Fluoro-1-(toluene-4-sulfonyl)-2,3-dihydro-1H-indol-5-yl]-pentyl}-methyl-amino)-ethanol,
and pharmaceutically acceptable salts and/or pharmaceutically acceptable esters thereof.

Further particularly preferred compounds of general formula (I) are those selected from the group consisting of 5-[5-(Allyl-methyl-amino)-pent-1-ynyl]-6-fluoro-2,3-dihydro-indole-1-carboxylic acid 4-chloro-phenyl ester,
5-{5-[Ethyl-(2-hydroxy-ethyl)-amino]-pent-1-ynyl}-6-fluoro-2,3-dihydro-indole-1-carboxylic acid 4-chloro-phenyl ester,
6-Fluoro-5-[5-(methyl-propyl-amino)-pentyl]-2,3-dihydro-indole-1-carboxylic acid phenyl ester,
and pharmaceutically acceptable salts and/or pharmaceutically acceptable esters thereof.

Still more preferred embodiments of the invention are those of general formula (VII)

(VII)

wherein
V is O or Ch$_2$;
L is lower-alkylene or lower-alkenylene;
W is COO, CONH, CSNH or CSO;
A$^1$ is hydrogen or lower-alkyl;
A$^2$ is lower alkyl or lower alkenyl;
m is 1 or 2; and
A$^5$ is lower alkyl, phenyl or lower alkyl phenyl, wherein the phenyl group is optionally substituted with halogen;
and pharmaceutically acceptable salts and esters thereof.
Preferred compounds of general formula (VII) are those selected from the group consisting of 5-[5-(Allyl-methyl-amino)-pentyl]-2,3-dihydro-indole-1-carbothioic acid O-(4-chloro-phenyl)ester,
5-[4-(Allyl-methyl-amino)-butoxy]-2,3-dihydro-indole-1-carbothioic acid O-(4-chloro-phenyl)ester,
5-[5-(Allyl-methyl-amino)-pentyl]-2,3-dihydro-indole-1-carboxylic acid 4-chloro-phenyl ester,
6-[4-(Allyl-methyl-amino)-but-2-enyloxy]-3,4-dihydro-2H-quinoline-1-carboxylic acid (4-fluoro-phenyl)-amide,
5-[4-(Allyl-methyl-amino)-butoxy]-2,3-dihydro-indole-1-carbothioic acid 4-fluoro-benzylamide,
5-[5-(Allyl-methyl-amino)-pentyl]-2,3-dihydro-indole-1-carbothioic acid 4-chloro-benzylamide,
5-[5-(Allyl-methyl-amino)-pentyl]-2,3-dihydro-indole-1-carboxylic acid (4-fluoro-phenyl)-amide,
5-[5-(Allyl-methyl-amino)-pentyl]-2,3-dihydro-indole-1-carbothioic acid O-(4-fluoro-phenyl)ester,
5-[5-(Allyl-methyl-amino)-pentyl]-2,3-dihydro-indole-1-carbothioic acid (4-chloro-phenyl)-amide,
5-[4-(Allyl-methyl-amino)-butoxy]-2,3-dihydro-indole-1-carbothioic acid (2-methyl-butyl)-amide, and
5-[4-(Allyl-methyl-amino)-butoxy]-2,3-dihydro-indole-1-carbothioic acid butylamide,
and pharmaceutically acceptable salts and/or pharmaceutically acceptable esters thereof.

Compounds of formulas (I) and (VII) can have one or more asymmetric carbon atoms and can exist in the form of optically pure enantiomers or as racemats. The invention embraces all of these forms.

It will be appreciated, that the compounds of general formula (I) in this invention may be derivatised at functional groups to provide derivatives which are capable of conversion back to the parent compound in vivo.

The present invention also relates to a process for the manufacture of compounds as described above, which process comprises reacting a compound of formula (II)

(II)

with a compound (A$^1$, A$^2$, U)N—C(A$^3$, A$^4$)—L—M, wherein V is O, S or NR$^1$, M is mesylate, tosylate, triflate, Cl, Br or I, and U, A$^1$, A$^2$, A$^3$, A$^4$, A$^5$, L, W, X, m, n and R$^1$ are as defined above, or wherein HV is mesylate, tosylate, triflate, Cl, Br or I, and M is OH, SH or NHR$^1$, and R$^1$ is as defined above, or b) reacting a compound of formula (III)

(III)

with a compound NHA$^1$, A$^2$, wherein M is mesylate, tosylate, triflate, Cl, Br or I, and A$^1$, A$^2$, A$^3$, A$^4$, A$^5$, L, V, W, X, m and n are as defined above, or c) reacting a compound of formula (IV)

(IV)

with a compound (A$^1$, A$^2$, U)N—C(A$^3$, A$^4$)—L—C≡CH, wherein M is Br or F$_3$CO$_2$SO, and U, A$^1$, A$^2$, A$^3$, A$^4$, A$^5$, L, W, X and m are as defined above, or d) reacting a compound of formula (V)

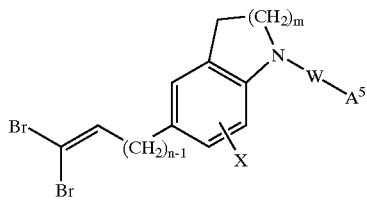

with a compound $(A^1, A^2, U)N-C(A^3, A^4)-L-M$, wherein M is mesylate, tosylate, triflate, Cl, Br or I, and $A^1, A^2, A^3, A^4, A^5$, W, U, L, X, m and n are as defined above, or e) hydrogenating a compound of formula (VI)

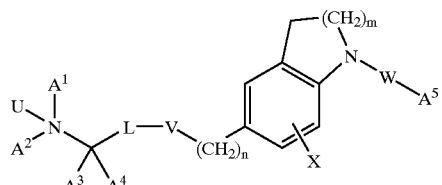

wherein V is $-C\equiv C-$, and $A^1, A^2, A^3, A^4, A^5$, U, W, L, X, m and n are as defined above, and optionally converting a compound according to any of claims 1 to 21 to a pharmaceutically acceptable salt, and optionally converting a compound according to any of claims 1 to 21, wherein U is a lone pair, to a corresponding compound wherein U is O.

The invention further relates to compounds of formula (I) as defined above, when manufactured according to a process as defined above.

As described above, the compounds of formula (I) of the present invention can be used for the treatment and/or prophylaxis of diseases which are associated with OSC such as hypercholesterolemia, hyperlipemia, arteriosclerosis, vascular diseases, mycoses, parasite infections and gallstones, and/or treatment and/or prophylaxis of impaired glucose tolerance, diabetes, tumors and/or hyperproliferative disorders, preferably for the treatment and/or prophylaxis of hypercholesterolemia and/or hyperlipemia. Hyperproliferative skin and vascular disorders particularly come into consideration as hyperproliferative disorders.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prophylaxis of of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia.

In another embodiment, the invention relates to a method for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia, which method comprises administering a compound as defined above to a human being or animal.

The invention further relates to the use of compounds as defined above for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia.

In addition, the invention relates to the use of compounds as defined above for the preparation of medicaments for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia. Such medicaments comprise a compound as defined above.

The compounds of formula (I) can be manufactured by the methods given below, by the methods given in the examples or by analogous methods. Appropriate reaction conditions for the individual reaction steps are known to the person skilled in the art. Starting materials are either commercially available or can be prepared by methods analogous to the methods given below or in the examples or by methods known in the art, e.g. by methods described in: Richard J. Sundberg Indoles (Best Synthetic Methods), Series Editor A. R. Katritzky, O. Meth-Cohn, C. W. Rees, Academic Press, San Diego 1996, or inHouben-Weyl Methoden der Organischen Chemie, R. P. Kreker, Ed., Georg Thieme Verlag, Stuttgart, 1994, or The Chemistry of Heterocyclic Compounds. A Series of Monographs, Vol. 32, Quinolines. Part 1–3, Weissenberger, E. C. Taylor, G. Jones, Eds, Wiley, London.

Scheme 1

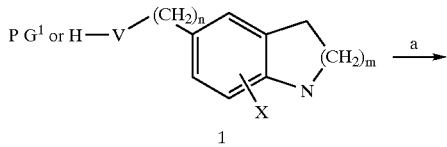

1

PG 1 = protecting groups such as Me, Bn (V = O, n = 0).
Me, Et, tBu (V = S, n = 0)
sily groups for O, BOC or Z for N,
trityl, p-methoxybenzyl for S -continued
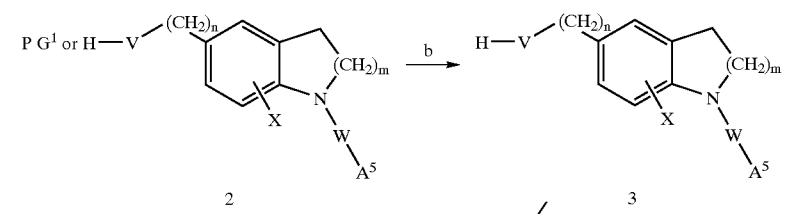
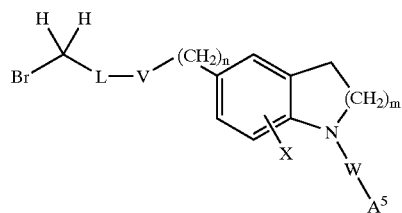
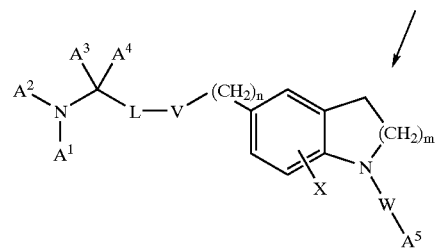
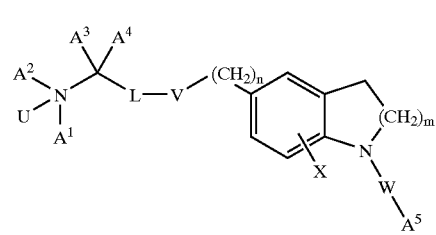

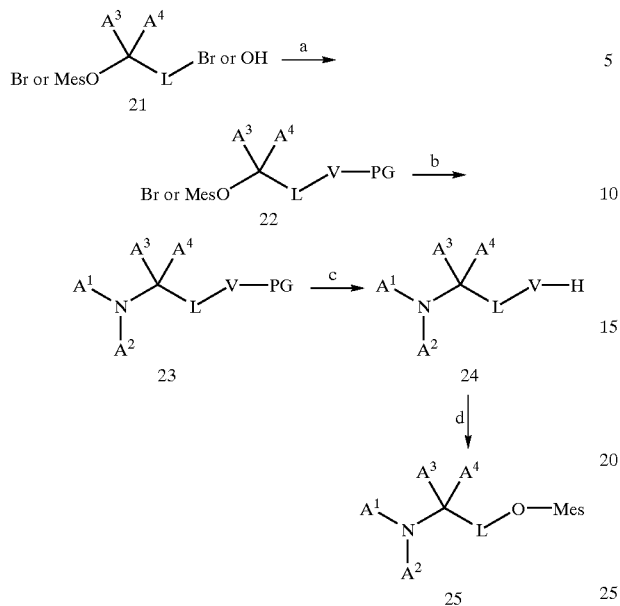
PG = protecting group, such as trityl for V = sulfur or BOC for V = NR¹

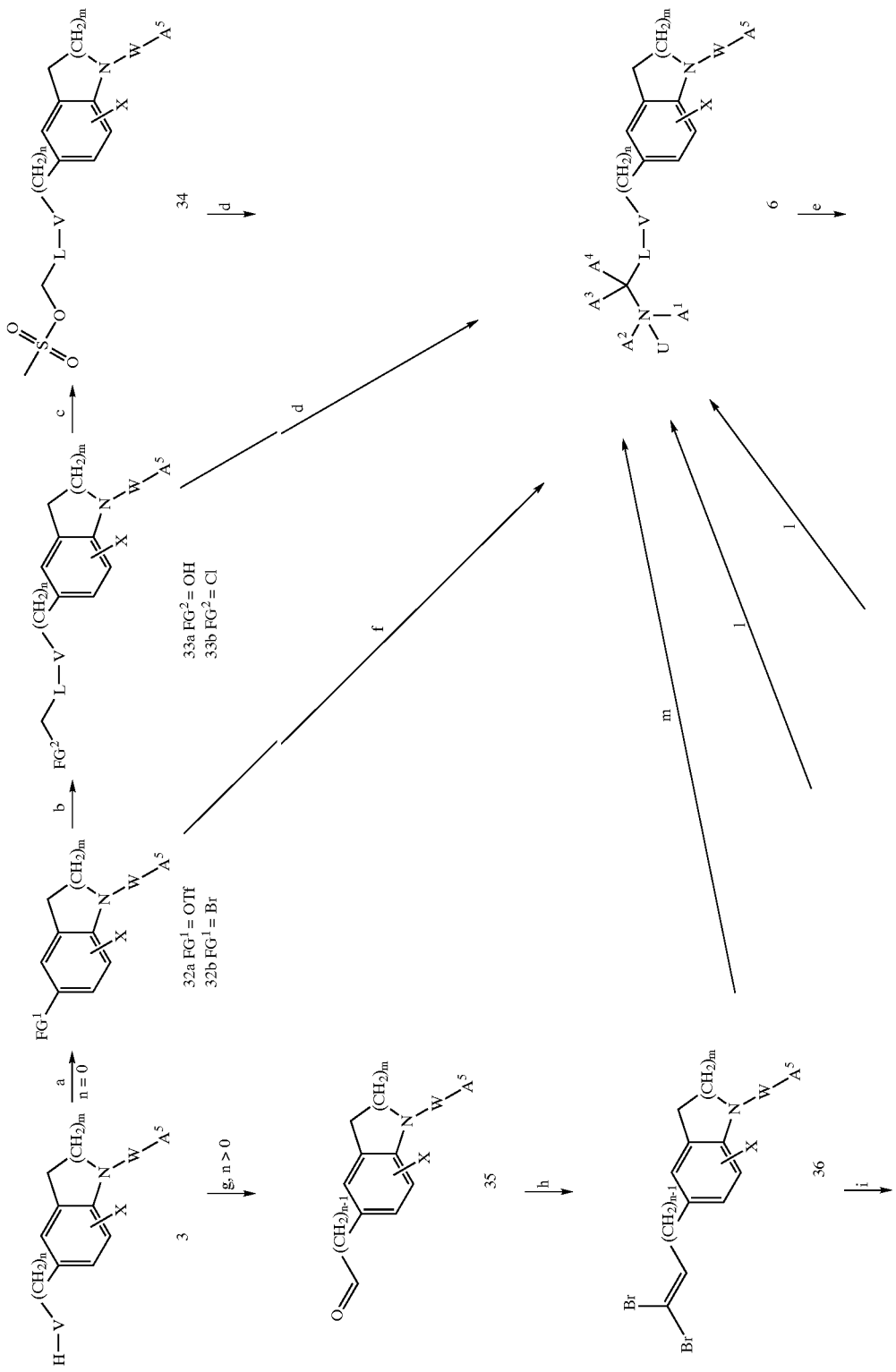

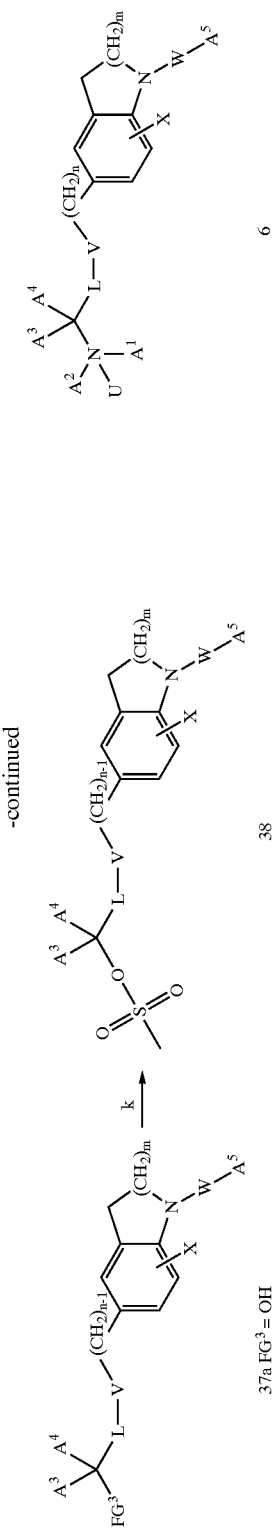

Scheme 1

If starting material 1 is a tetrahydroquinoline derivative (m=2), it may be derived from the corresponding quinoline derivative by hydrogenation with $PtO_2$ in a suitable solvent such as methanol, ethanol. If starting material 1 is an indoline derivative (m=1), it maybe derived from the corresponding indole derivative for example by treatment with $NaCNBH_3$ in acetic acid or trifluoro acetic acid or by employing other methods known in the art.

Derivative 1 is either N-protected (e.g. $(BOC)_2O$, $CH_2Cl_2$) to yield compound 2 or is directly converted to the desired $A^5W$-substituted derivative 2 using one of the methods described later for compound 5.

Deprotection of the V-group can be achieved, if 2 is a 5-benzyloxyindoline derivative, by hydrogenation with e.g. Pd/C in solvents like methanol, ethanol or ethyl acetate, if 2 is a 5-methoxy-indoline derivative, by treatment for example with lithium-tri-sec-butylborohydride in THF. For V=S, $NR^1$ or V=O and n>0, deprotection using procedures known in the art (step c) yields the building block 3.

Alkylation of the phenol/thiophenol 3 (V=O, S, n=0) is accomplished in acetone or DMF with $K_2CO_3$ and a suitable dihaloalkane or dihaloalkene (halogene is here represented by bromine, but can also be chlorine or iodine. It is also possible to use mesylates, tosylates or triflates instead of halogenides) at reflux to yield halogenide 4 (step c). For the preparation of derivatives 4 (V=O, n>0), the alcohol 3 can be treated with α,ω-dihaloalkanes or α,ω-dihaloalkenes under phase transfer conditions e.g. α,ω-dihaloalkanes/dihaloalkenes, NaOH, $nBu_4NHSO_4$. For V=S, O or $NR^1$, the derivative 3 may be treated with α,ω-dihaloalkane in the presence of NaH in DMF 0° C. to RT to yield bromide 4. For shorter alkanes (methyl, ethyl), the method of choice is the in situ generation of the haloalkane-triflate (from the corresponding haloalkanol with trifluoromethansulfonic anhydride/2,6-di-tert-butylpyridine in $CH_2Cl_2$ at 0° C.). This haloalkane-triflate may then be reacted with 3 in the presence of a base such as 2,6-di-tert-butylpyridine in nitromethane at 60° C. to yield bromide 4 [analogously to a procedure of Belostotskii, Anatoly M.; Hassner, Alfred. Synthetic methods. 41. Etherification of hydroxysteroids via triflates. Tetrahedron Lett. (1994), 35(28), 5075].

Compound 4 can be converted to the amine 5 with an excess of the corresponding amine $NHA^1A^2$ in a suitable solvent such as DMA, DMF, MeOH at RT or at 50–65° C. or by treatment with $NHA^1A^2$, NaH in solvents such as DMF or THF (step d).

Compound 5 can be N-deprotected using TFA in $CH_2Cl_2$ for BOC-groups or by hydrogenation in methanol, ethanol or ethyl acetate with Pd/C for Z-groups.

The resulting amine (not shown in scheme 1) may be treated according to one of the following procedures to yield the appropriate $A^5W$-substituted derivative 5 (separation by HPLC was necessary in some cases).

Sulfonamides: Sulfonylation of the amines is done in dioxane or $CH_2Cl_2$ with Huenig's base and a sulfonyl chloride over night at RT to yield the sulfonamide 5.

Carbamates: The amines may be reacted with $A^5OCOCl$/Huenig's base or pyridine in dioxane, THF, DMF or $CH_2Cl_2$. Alternatively, the chloroformates may be prepared in situ by treatment of $A^5OH$ with $Cl_3COCl$ in the presence of quinoline followed by reaction with the amines in the presence of Huenig's base.

Thiocarbamates: The amines may be reacted with $A^5OCSCl$ in dioxane.

Ureas: The amines may be reacted with isocyanate in dioxane at room temperature.

Thioureas: The amines maybe reacted with isothiocyanate in dioxane at room temperature.

Amides: The amines may be reacted with $A^5COOH$/EDCI/DMAP (with anhydride formation, and subsequent addition of the starting amine at −10° C. to room temperature) or alternatively with $A^5COOH$/EDCI/DMAP or $A^5COOH$/Huenig's base/EDCI/HOBT in DMF, dioxane or $CH_2Cl_2$ at room temperature.

Sulfamides: The amines may be reacted with sulfamoyl chlorides in dioxane in the presence of an excess of triethylamine to yield sulfamide 5. The sulfamoyl chlorides can be prepared from $A^5NH_2$ and chlorosulfonic acid in $CH_2Cl_2$ at 0° C. to room temperature followed by reaction with $PCl_5$ in toluene at 75° C. Alternatively, the sulfamoyl chlorides can be synthesized in acetonitrile with $A^5NH_2$ and sulfuryl chloride at 0° C. to 65° C.

Alternatively, the compound 3 may be converted to the amine 5 by attaching the pre-assembled fragment $A^1A^2NC(A^3A^4)LV$—OMes/halogenide/triflates, which can be synthesised by known methods (shown e.g. in Scheme 2), using alkylating conditions (step f). Compounds 3 (V=O, n>0) can also be mesylated (V=OMes) and then reacted with $A^1A^2NC(A^3A^4)L$—VH (synthesis as described in Scheme 2) in e.g. DMF with NaH as base to yield 5 (with V=O, S, $NR^1$).

Amine 5 may be converted to a salt or to the N-oxide 6 (step e). For N-oxide 6 (V=O) a mixture of hydrogen peroxide urea adduct and phthalic anhydride in $CH_2Cl_2$ at RT may be used. For the preparation of the N-oxides 6 (V=S or $NR^1$) an alternative route has to be employed (step g): Oxidation of the pre-assembled fragment $A^1A^2NC(A^3A^4)L$—OMes/halogenide to the corresponding N-oxide derivative, followed by alkylation of the compound 3 to give compound 6 directly.

If $WA^5$ is a protective group, this may be cleaved as described for derivative 5 and the final moieties $WA^5$ may be introduced as described above.

Scheme 2

Scheme 2 shows the synthesis of amino-VH sidechain 24 that may be used for the synthesis of compounds with the corresponding V-spacers (V=$NR^4$, S, or O). α,ω-dihaloalkane, mesyl-alkanyl-halogenide, α,ω-dihaloalkene, mesyl-alkenyl-halogenide 21 may be treated with a suitable protected amine (HNR$^1$-PG, PG=protecting group, e.g. BOC) in DMA or a thiol (HS-PG e.g., triphenylmethanethiol) in the presence of NaH in DMA to yield the compound 22(step a). Treatment with the amine $A^1A^2NH$ yields the S- or N-protected amine 23 (step b) or in the case of α,ω-haloalkanol or α,ω-haloalkenol 21 directly amino-alcohol 24. N-deprotection with procedures known in the art e.g. TFA in $CH_2Cl_2$ yields the amine side chain 24 (step c). The deprotection of the thiol moiety in 23 may be achieved with TFA/triisopropylsilane in $CH_2Cl_2$ at 0° C. to RT to yield the aminothiol 24 (step c). Aminoalkanol 24 can be transformed further to mesylate 25 (step d).

Scheme 3

In Scheme 3, the preparation of compounds of formula 6, in which V represents —$CH_2$—, —CH=CH— or —C≡C— is outlined. The starting material is derivative 3, which may be converted to the triflate 32a in pyridine with trifluoromethanesulfonic anhydride at 0° C. to RT (step a). Sonogashira-coupling (step b) of the triflate 32a and a suitable alkynol or alkynechloride in piperidine with $Pd(PPh_3)_4$/CuI at 45° C. to 80° C. in analogy to a literature procedure yields alcohol 33a or chloride 33b [Stara, Irena G.; Stary, Ivo; Kollarovic, Adrian; Teply, Filip; Saman, David; Fiedler, Pavel. Coupling reactions of halobenzenes with alkynes. The synthesis of phenylacetylenes and symmetrical or unsymmetrical 1,2-diphenylacetylenes. Collect. Czech. Chem. Commun. (1999), 64(4), 649–672.].

Alternatively, the alkynes 33a or 33b can be prepared by Sonogashira reaction of the bromo-derivatives 32b with the corresponding alkynols or alkynechlorides.

Mesylation of alcohol 33a with methanesulfonylchloride e.g. in solvents such as pyridine or $CH_2Cl_2$ with bases like triethylamine or Huenig's base optionally in the presence of DMAP (reaction step c) and subsequent amination (reaction step d) of the resulting mesylate 34 with a suitable amine $NHA^1A^2$ in a solvent like DMA, DMF or MeOH at RT or at 50–65° yields the amine 6. Alcohol 33a can also be treated with trifluoromethane sulfonic acid anhydride and Huenig's base at −15° C. in $CH_2Cl_2$ (in situ generation of the corresponding triflate) followed by treatment with the corresponding amine $NHA^1A^2$ at −15° C. to RT. This is especially the method of choice for but-3-yn-1-ol-derivatives 33a. Chloride 33b can be transformed directly or via iodide (Finkelstein reaction) to the amine 6, as described above (step d). Compounds 6 in which V is —$CH_2$— or —CH=CH— can be obtained by hydrogenation of compound 6 in solvents like MeOH or EtOH with $Pt_2O.H_2O$ or Pd/C (yields the saturated analogue 6) or by selective hydrogenation with other known methods (e.g. Lindlar or DIBAH, REDAL) (yields the double bond analogue 6). Optionally, the hydrogenation described above can be performed at an earlier stage e.g. the alcohol 33a or mesylate 34.

Alternatively, the group $A^1A^2NC(A^3A^4C)$-L-acetylene can be synthesised by known methods and attached to compound 32a or 32b (Sonogashira-coupling), to yield the compounds of the present invention 6 (reaction step f).

Compounds of the formula 5 (n>0) may be synthesised by Swern oxidation of the alcohol 3 (V=O and n>0) to yield the corresponding aldehyde 35 (step g) as an intermediate. The aldehyde 35 may be treated with triphenylphosphine, tetra-bromo-methane and triethylamine in $CH_2Cl_2$ at 0° C. to RT to yield 2,2-Dibromo-vinyl derivative 36 (step h). Rearrangement with n-BuLi (ca 1.6 M in hexane) in THF at −78° C., followed by reaction with formaldehyde (−78° C. to RT) leads to the propargyl alcohol 37a (step i, side chain extension through application of the Corey-Fuchs method), following conditions described in: Marshall, James A.; Bartley, Gary S.; Wallace, Eli M. Total Synthesis of the Pseudopterane (−)-Kallolide B, the Enantiomer of Natural (+)-Kallolide B. J. Org. Chem. (1996), 61(17), 5729–5735; and Baker, Raymond; Boyes, Alastair L.; Swain, Christopher J. Synthesis of talaromycins A, B, C, and E. J. Chem. Soc., Perkin Trans. 1 (1990), (5), 1415–21.

For longer side chains, the rearrangement is performed with n-BuLi (ca 1.6 M in hexane) in THF at −78° C. as above, followed by addition of a co-solvens such as DMPU and reaction with O-protected 1-bromo-alcohols (e.g. 1-bromo-n-tetrahydro-pyaranyloxyalkane) to yield the O-protected compounds 37b (step i). O-protected compounds 37b can be deprotected to the corresponding alkynol 37a (in MeOH at 50–60° C., in the presence of catalytic amount of pyridinium toluene-4-sulfonate). Alcohol 37a can be reacted with Huenig's base/trifluoromethane sulfonic acid anhydride at −15° C. in $CH_2Cl_2$ (in situ generation of the corresponding triflate) followed by treatment with Huenig's base and the corresponding amine $NHA^1A^2$ at −15° C. to RT to yield amine 6. Alternatively, mesylation of alcohol 37a with methanesulfonylchloride, pyridine and DMAP in $CH_2Cl_2$ at 0° C. to RT yields mesylate 38. Conversion of the mesylate 38 to the amine 6 can be accomplished with an excess of the corresponding amine $NHA^1A^2$ in DMA at RT or as described above (step 1).

Compounds 6 in which V is —$CH_2$— or —CH=CH— can be obtained by hydrogenation of compound 5 itself or the intermediates 37a, 37b or 38. The hydrogenation may be performed in EtOH or MeOH with $Pt_2O.H_2O$ or Pd/C (yields the saturated analogues 6, 37a, 37b, or 38) or by selective hydrogenation to obtain the double bond by other known methods (e.g. Lindlar or DIBAH, REDAL) and transforming the intermediates afterwards to 6.

Alternatively, for the introduction of the group $A^1A^2N(A^3A^4C)L$ in which $A^3$ and/or $A^4$ are not H, the following steps have to be performed starting from compound 36 (step m or steps i and l): for L=lower alkanes, the building block $A^1A^2N(A^3A^4C)L$-halogenide/mesylate is synthesised by known methods (or in analogy to the methods described in Scheme 2) and introduced (step m) under the same condition as described above for step i. For L=single bond, the introduction of the group $A^1A^2N(A^3A^4C)$ with $A^3$ and/or $A^4$ not H, a two step procedure has to be followed: first the rearrangement of 36 with n-BuLi (ca 1.6 M in hexane) in THF at −78° C., followed by reaction with the corresponding aldehyde ($A^3$ or $A^4$—COH) or ketone ($A^3COA^4$, at −78° C. to RT) leads to the $A^3A^4$ substituted propargyl alcohol 37a (step i) which is e.g. mesylated or transformed to a phosphorester or a chloride (not shown) and reacted with the desired $A^1A^2$-substituted-amine in the presence of Tetrakis (triphenylphosphine)palladium (for the phosphorester) or Cu(I)Cl/Cu bronze and Huenig's base (for the chloride) to yield the desired $A^3$, $A^4$-substituted compound 5 (step l ). (see: Bartlett, Paul A.; McQuaid, Loretta A. Total synthesis of (±)-methyl shikimate and (±)-3-phosphoshikimic acid. J. Am. Chem. Soc. (1984), 106(25), 7854–60 and Cooper, Matthew A.; Lucas, Mathew A.; Taylor, Joanne M.; Ward, A. David; Williamson, Natalie M. A convenient method for the aromatic amino-Claisen rearrangement of N-(1,1-disubstituted-allyl)anilines. Synthesis (2001), (4), 621–625.)

Amine 6 may be converted to a salt or to the N-oxide 6 using a mixture of hydrogen peroxide urea adduct and phthalic anhydride in $CH_2Cl_2$ at RT (step e).

If $WA^5$ is a protecting group, this may be cleaved and the final moieties $WA^5$ may be introduced as described for derivative 5 in scheme 1.

The following tests were carried out in order to determine the activity of the compounds of formula I and their salts.
Inhibition of Human Liver Microsomal 2,3-oxidosqualene-lanosterol Cyclase (OSC)

Liver microsomes from a healthy volunteer were prepared in sodium phosphate buffer (pH 7.4). The OSC activity was measured in the same buffer, which also contained 1 mM EDTA and 1 mM dithiothreitol. The microsomes were diluted to 0.8 mg/ml protein in cold phosphate buffer. Dry [$^{14}$C]R,S-monooxidosqualene (MOS, 12.8 mCi/mmol) was diluted to 20 nCi/µl with ethanol and mixed with phosphate buffer-1% BSA (bovine serum albumin). A stock solution of 1 mM test substance in DMSO was diluted to the desired concentration with phosphate buffer-1% BSA. 40 µl of microsomes were mixed with 20 µl of the solution of the test substance and the reaction was subsequently started with 20 µl of the [$^{14}$C]R,S-MOS solution. The final conditions were: 0.4 mg/ml of microsomal proteins and 30 µl of [$^{14}$C]R,S-MOS in phosphate buffer, pH 7.4, containing 0.5% albumin, DMSO<0.1% and ethanol<2%, in a total volume of 80 µl.

After 1 hour at 37° C. the reaction was stopped by the addition of 0.6 ml of 10% KOH-methanol, 0.7 ml of water and 0.1 ml of hexane:ether (1:1, v/v) which contained 25 µg of non-radioactive MOS and 25 µg of lanosterol as carriers.

After shaking, 1 ml of hexane:ether (1:1, v/v) was added to each test tube, these were again shaken and then centrifuged. The upper phase was transferred into a glass test tube, the lower phase was again extracted with hexane:ether and combined with the first extract. The entire extract was evaporated to dryness with nitrogen, the residue was suspended in 50 µl of hexane:ether and applied to a silica gel plate. Chromatographic separation was effected in hexane:ether (1:1, v/v) as the eluent. The Rf values for the MOS substrate and the lanosterol product were 0.91 and, respectively, 0.54. After drying, radioactive MOS and lanosterol were observed on the silica gel plate. The ratio of MOS to lanosterol was determined from the radioactive bands in order to determine the yield of the reaction and OSC inhibition.

The test was carried out on the one hand with a constant test substance concentration of 100 nM and the percentage OSC inhibition against controls was calculated. The more preferred compounds of the present invention exhibit inhibitions larger than 50%. In addition, the test was carried out with different test substance concentrations and subsequently the $IC_{50}$ value was calculated, i.e. the concentration required to reduce the conversion of MOS into lanosterol to 50% of the control value. The preferred compounds of the present invention exhibit $IC_{50}$ values of 1 nM to 10 µM, preferably of 1–100 nM.

The compounds of formula I and their pharmaceutically acceptable acid addition salts can be used as medicaments, e.g. in the form of pharmaceutical preparations for enteral, parenteral or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable acid addition salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 50 mg to about 500 mg, comes into consideration for the prevention and control of topical and systemic infections by pathogenic fungi. For cholesterol lowering and treatment of impaired glucose tolerance and diabetes the daily dosage conveniently amounts to between 1 and 1000 mg, preferably 5 to 200 mg, for adult patients. Depending on the dosage it is convenient to administer the daily dosage in several dosage units.

The pharmaceutical preparations conveniently contain about 1–500 mg, preferably 5–200 mg, of a compound of formula I.

The following Examples serve to illustrate the present invention in more detail. They are, however, not intended to limit its scope in any manner.

EXAMPLES

Abbreviations

AcOH=acetic acid, n-BuLi=n-Butyl lithium, CuI=copper iodide, DMF=N,N-dimethylformamide, $Et_2O$=ether=diethyl ether, EtOAc=ethyl acetate, eq.=equivalents, Huenig's base=N,N-diisopropylethylamine, KOtBu=potassium tert. butylate, MeOH=methanol, NaOtBu=sodium tert. butylate, $NEt_3$=triethylamine, Pd/C=palladium on carbon, $PdCl_2(PPh_3)_2$=bis(triphenylphosphine)palladium(II) chloride, $Pd(Ph_3P)_4$=tetrakis(triphenylphosphine)palladium, RT=room temperature, THF=tetrahydrofuran, TFA=trifluoroacetic acid.

General Remarks

All reactions were performed under argon.

The purification of the final amines by preparative HPLC [e.g. RP-18, acetonitrile (0.1% HCOOH)/water (0.1% HCOOH), 10% to 95% acetonitrile] yielded mixtures of the corresponding amino formate and the corresponding halogenide or methanesulfonic acid salt which was used in the reaction. The ratio was not always determined, the purity of the final amino salts was >80% after LC-MS.

Example 1

1.1

1,2,3,4-Tetrahydro-quinolin-6-ol can be prepared from quinolin-6-ol according to Moore; Capaldi; J.Org.Chem., 29, 1964, 2860 or Hoenel, Michael; Vierhapper, Friedrich W.; J.Chem.Soc.Perkin Trans. 1, 1980, 1933–1939.

1.2

To 750 mg (5 mmol) 1,2,3,4-Tetrahydro-quinolin-6-ol in 10 ml THF 950 mg (5 mmol) 4-chlorophenylchloroformate were added. The solution was stirred at RT for 30 min, 0.5 ml (6 mmol) pyridine were added and the solution was stirred for additional 30 min. The mixture was concentrated in vacuo and dissolved in EtOAc, water and 2M HCl was added. The inorganic phase was extracted with EtOAc, the combined organic phases were washed with water and dried over $Na_2SO_4$. Column chromatography on silica gel with $CH_2Cl_2$/MeOH 49:1 yielded 600 mg (40%) 6-Hydroxy-3,4-dihydro-2H-quinoline-1-carboxylic acid 4-chloro-phenyl ester as colorless gum, MS: 303 (M, 1Cl).

1.3

To 304 mg (1 mmol) 6-Hydroxy-3,4-dihydro-2H-quinoline-1-carboxylic acid 4-chloro-phenyl ester in 4 ml DMF 420 mg (3 mmol) K$_2$CO$_3$ (powdered) and 416 mg (2 mmol) 1,4-dibromobutene were added. The mixture was stirred at 50° C. for 1 h, diluted with EtOAc and water. 2M HCl was added and the inorganic phase was extracted with EtOAc. The combined organic phases were washed with water and dried over Na$_2$SO$_4$. The crude product was purified by column chromatography on silica gel with hexane/EtOAc 9:1 to 4:1 to yield 250 mg (46%) 6-(4-Bromo-but-2-enyloxy)-3,4-dihydro-2H-quinoline-1-carboxylic acid 4-chloro-phenyl ester as colorless gum, MS: 436 (MH$^+$, 1Br, 1Cl).

1.4

To 245 mg (0.8 mmol) 6-Hydroxy-3,4-dihydro-2H-quinoline-1-carboxylic acid 4-chloro-phenyl ester in 5 ml acetone 323 mg (2.3 mmol) K$_2$CO$_3$ (powdered) and 0.21 ml (2.1 mmol) 1,3-dibromopropane were added. The mixture was stirred at reflux for 4 h, filtered and concentrated. The residue was dissolved in EtOAc and water, and the inorganic phase was extracted with EtOAc. The combined organic phases were washed with water and dried over Na$_2$SO$_4$. The crude product was purified by column chromatography on silica gel with CH$_2$Cl$_2$ yielding 210 mg (61%) 6-(3-Bromo-propoxy)-3,4-dihydro-2H-quinoline-1-carboxylic acid 4-chloro-phenyl ester as colorless oil, MS: 424 (MH$^+$, 1Br, 1Cl).

1.5

In analogy to example 1.4, 6-Hydroxy-3,4-dihydro-2H-quinoline-1-carboxylic acid 4-chloro-phenyl ester and 1,4-dibromobutane were converted to yield 6-(4-Bromo-butoxy)-3,4-dihydro-2H-quinoline-1-carboxylic acid 4-chloro-phenyl ester as colorless oil, MS: 438 (MH$^+$, 1Br, 1Cl);

1.6

In analogy to example 1.4, 6-Hydroxy-3,4-dihydro-2H-quinoline-1-carboxylic acid 4-chloro-phenyl ester and 1,5-dibromopentane (80%) were converted to yield 6-(5-Bromo-pentyloxy)-3,4-dihydro-2H-quinoline-1-carboxylic acid 4-chloro-phenyl ester as colorless oil, MS: 451 (M, 1Br, 1Cl).

1.7

To 153 mg (0.35 mmol) 6-(4-Bromo-but-2-enyloxy)-3,4-dihydro-2H-quinoline-1-carboxylic acid 4-chloro-phenyl ester in 3 ml DMF 71 mg (1 mmol) N-allylmethylamine and 140 mg (1 mmol) K$_2$CO$_3$ (powdered) were added and the mixture was stirred at 60° C. for 1 h. The mixture was concentrated in vacuo, 8 ml acetone were added, the suspension was filtered and the filtrate was concentrated. Column chromatography on silica gel with CH$_2$Cl$_2$/MeOH 9:1 yielded 95 mg (64%) 6-[4-(Allyl-methyl-amino)-but-2-enyloxy]-3,4-dihydro-2H-quinoline-1-carboxylic acid 4-chloro-phenyl ester as colorless oil, MS: 426 (M, 1Cl).

1.8

To 210 mg (0.49 mmol) 6-(3-Bromo-propoxy)-3,4-dihydro-2H-quinoline-1-carboxylic acid 4-chloro-phenyl ester in 5 ml DMF 191 µl (2 mmol) N-allylmethylamine and 106 mg (4.2 mmol, 50% in hexane) NaH were added. The mixture was stirred at RT for 4 h and extracted with ether and water. The organic phase was washed with water and dried over Na$_2$SO$_4$. Column chromatography on silica gel with CH$_2$Cl$_2$/MeOH 9:1 yielded 70 mg (34%) 6-[3-(Allyl-methyl-amino)-propoxy]-3,4-dihydro-2H-quinoline-1-carboxylic acid 4-chloro-phenyl ester as colorless oil, MS: 415 (MH$^+$, 1Cl).

1.9

In analogy to example 1.8, 6-(5-Bromo-pentyloxy)-3,4-dihydro-2H-quinoline-1-carboxylic acid 4-chloro-phenyl ester and N-allylmethylamine were converted to yield 6-[5-(Allyl-methyl-amino)-pentyloxy]-3,4-dihydro-2H-quinoline-1-carboxylic acid 4-chloro-phenyl ester as colorless oil, MS: 443 (MH$^+$, 1Cl).

1.10

240 mg (0.55 mmol) 6-(4-Bromo-butoxy)-3,4-dihydro-2H-quinoline-1-carboxylic acid 4-chloro-phenyl ester and 260 µl (2.7 mmol) N-allylmethylamine were stirred in 5 ml DMF at RT for 3 h. The mixture was extracted with ether and water, the organic phase was washed with water and dried over Na$_2$SO$_4$. Purification by column chromatography on silica gel with CH$_2$Cl$_2$/MeOH 9:1 yielded 154 mg (66%) 6-[4-(Allyl-methyl-amino)-butoxy]-3,4-dihydro-2H-quinoline-1-carboxylic acid 4-chloro-phenyl ester as colorless oil, MS: 429 (MH$^+$, 1Cl).

Example 2

2.1

To 9.7 g (65 mmol) 1,2,3,4-Tetrahydro-quinolin-6-ol in 90 ml CH$_2$Cl$_2$ 13.7 g (62.8 mmol) di-tert.-butyl-dicarbonate were added. The solution was stirred at 50° C. for 5 h and at RT over night. The mixture was concentrated and dissolved in Et$_2$O. A diluted aqueous solution of KHSO$_4$ was added and the inorganic phase was extracted with Et$_2$O, the combined organic phases were washed with brine and dried over Na$_2$SO$_4$. Column chromatography on silica gel with CH$_2$Cl$_2$/MeOH 9:1 yielded 16.2 g (99%) 6-Hydroxy-3,4-dihydro-2H-quinoline-1-carboxylic acid tert-butyl ester as light yellow crystals, MS: 249 (M).

2.2

To 11.6 g (46.5 mmol) 6-Hydroxy-3,4-dihydro-2H-quinoline-1-carboxylic acid tert-butyl ester in 200 ml acetone 18.6 g (134.8 mmol) K$_2$CO$_3$ (powdered) and 13.7 g (115.7 mmol) 1,4-dibromobutane were added. The mixture was stirred at reflux for 4 h and at RT over night. The reaction mixture was filtered, and the filtrate was concentrated in vacuo. EtOAc and water were added, the inorganic phase was extracted with EtOAc and the combined organic phases were washed with water and dried over Na$_2$SO$_4$. The crude product was purified by column chromatography on silica gel with hexane/EtOAc 9:1 to yield 11.1 g (63%) 6-(4-Bromo-butoxy)-3,4-dihydro-2H-quinoline-1-carboxylic acid tert-butyl ester as colorless oil, MS: 383 (M, 1Br).

2.3

In analogy to example 2.2, 6-Hydroxy-3,4-dihydro-2H-quinoline-1-carboxylic acid tert-butyl ester and 1,4-dibromobutene were converted to yield 6-(4-Bromo-but-2-enyloxy)-3,4-dihydro-2H-quinoline-1-carboxylic acid tert-butyl ester as colorless oil, MS: 381 (M, 1Br);

2.4

In analogy to example 2.2, 6-Hydroxy-3,4-dihydro-2H-quinoline-1-carboxylic acid tert-butyl ester and 1,5-dibromopentane were converted to yield 6-(5-Bromo-pentyloxy)-3,4-dihydro-2H-quinoline-1-carboxylic acid tert-butyl ester (63%) as colorless oil, MS: 397 (M, 1Br);

2.5

In analogy to example 2.2, 6-Hydroxy-3,4-dihydro-2H-quinoline-1-carboxylic acid tert-butyl ester and 1,6-dibromohexane were converted to yield 6-(6-Bromo-hexyloxy)-3,4-dihydro-2H-quinoline-1-carboxylic acid tert-butyl ester (40%) as light green oil, MS: 412 (MH$^+$, 1Br);

2.6

1.5 g (3.75 mmol) 6-(5-Bromo-pentyloxy)-3,4-dihydro-2H-quinoline-1-carboxylic acid tert-butyl ester were treated with 355 mg (5 mmol) N-allyl-methylamine and 830 mg (6 mmol) K$_2$CO$_3$ (powdered) in 8 ml DMF at 60° C. for 3 h. The mixture was concentrated in vacuo, dissolved in acetone and filtered. The filtrate was concentrated and purified by column chromatography on silica gel with $CH_2Cl_2$/MeOH 19:1 to yield 1.05 g (72%) 6-[5-(Allyl-methyl-amino)-pentyloxy]-3,4-dihydro-2H-quinoline-1-carboxylic acid tert-butyl ester as colorless oil, MS: 389 ($MH^+$).

2.7

In analogy to example 2.6, 6-(6-Bromo-hexyloxy)-3,4-dihydro-2H-quinoline-1-carboxylic acid tert-butyl ester and N-allyl-methylamine were converted to yield 6-[6-(Allyl-methyl-amino)-hexyloxy]-3,4-dihydro-2H-quinoline-1-carboxylic acid tert-butyl ester as colorless gum, MS: 403 ($MH^+$).

2.8

In analogy to example 2.6, 6-(4-Bromo-but-2-enyloxy)-3,4-dihydro-2H-quinoline-1-carboxylic acid tert-butyl ester and N-allyl-methylamine were converted to yield 6-[4-(Allyl-methyl-amino)-but-2-enyloxy]-3,4-dihydro-2H-quinoline-1-carboxylic acid tert-butyl ester as colorless oil, MS: 373 ($MH^+$).

2.9

5.0 g (13.0 mmol) 6-(4-Bromo-butoxy)-3,4-dihydro-2H-quinoline-1-carboxylic acid tert-butyl ester were treated with 3.66 g (51.5 mmol) N-allyl-methylamine in 100 ml DMF at 50° C. for 30 min. The mixture was concentrated in vacuo, dissolved in $Et_2O$ and water. The inorganic layer was extracted with $Et_2O$, and the combined organic phases were washed with water and dried over $Na_2SO_4$. Purification by column chromatography on silica gel with $CH_2Cl_2$/MeOH 10:1 yielded 3.6 g (74%) 6-[4-(Allyl-methyl-amino)-butoxy]-3,4-dihydro-2H-quinoline-1-carboxylic acid tert-butyl ester as light yellow oil, MS: 375 ($MH^+$).

2.10

In analogy to example 2.9, 6-(4-Bromo-butoxy)-3,4-dihydro-2H-quinoline-1-carboxylic acid tert-butyl ester and diethylamine were converted to yield 6-(4-Diethylamino-butoxy)-3,4-dihydro-2H-quinoline-1-carboxylic acid tert-butyl ester as colorless oil.

Example 3

3.1

3.64 g (9.7 mmol) 6-[4-(Allyl-methyl-amino)-butoxy]-3,4-dihydro-2H-quinoline-1-carboxylic acid tert-butyl ester in 5 ml $CH_2Cl_2$ were treated with 3.5 ml TFA at 0° C., and the solution was stirred at 40° C. for 1 h. The solution was concentrated and the residue dissolved in a mixture of a saturated aqueous solution of $NaHCO_3$ and ether. The inorganic phase was extracted with ether and the combined organic phases were washed with water and dried over $Na_2SO_4$ to yield 1.85 g (69%) Allyl-methyl-[4-(1,2,3,4-tetrahydro-quinolin-6-yloxy)-butyl]-amine, MS: 275 ($MH^+$).

3.2

In analogy to example 3.1, 6-[4-(Allyl-methyl-amino)-but-2-enyloxy]-3,4-dihydro-2H-quinoline-1-carboxylic acid tert-butyl ester was converted to yield Allyl-methyl-[4-(1,2,3,4-tetrahydro-quinolin-6-yloxy)-but-2-enyl]-amine (crude) as orange oil, MS: 273 ($MH^+$).

3.3

In analogy to example 3.1, 6-[5-(Allyl-methyl-amino)-pentyloxy]-3,4-dihydro-2H-quinoline-1-carboxylic acid tert-butyl ester was converted to yield Allyl-methyl-[5-(1,2,3,4-tetrahydro-quinolin-6-yloxy)-pentyl]-amine (82%) as light yellow oil, MS: 289 ($MH^+$);

3.4

In analogy to example 3.1, 6-[6-(Allyl-methyl-amino)-hexyloxy]-3,4-dihydro-2H-quinoline-1-carboxylic acid tert-butyl ester was converted to yield Allyl-methyl-[6-(1,2,3,4-tetrahydro-quinolin-6-yloxy)-hexyl]-amine (93%) as colorless gum, MS: 303 ($MH^+$);

3.5

In analogy to example 3.1, 6-(4-Diethylamino-butoxy)-3,4-dihydro-2H-quinoline-1-carboxylic acid tert-butyl ester was converted to yield Diethyl-[4-(1,2,3,4-tetrahydro-quinolin-6-yloxy)-butyl]-amine as light brown oil, MS: 277 ($MH^+$).

3.6

To 54 mg (0.2 mmol) Allyl-methyl-[4-(1,2,3,4-tetrahydro-quinolin-6-yloxy)-but-2-enyl]-amine in 2 ml $CH_2Cl_2$ 3 drops of Huenig's base and 527 mg (0.25 mmol) 4-chlorobenzene sulfonylchloride were added. The solution was stirred at RT for 2 h, concentrated and purified by column chromatography on silica gel with $CH_2Cl_2$/MeOH 19:1 to yield 70 mg (78%) Allyl-{4-[1-(4-chloro-benzenesulfonyl)-1,2,3,4-tetrahydro-quinolin-6-yloxy]-but-2-enyl}-methyl-amine as yellow oil, MS: 447 ($MH^+$, 1Cl).

3.7

In analogy to example 3.6, Allyl-methyl-[6-(1,2,3,4-tetrahydro-quinolin-6-yloxy)-hexyl]-amine and 4-chlorobenzene sulfonylchloride were converted to yield Allyl-{5-[1-(4-chloro-benzenesulfonyl)-1,2,3,4-tetrahydro-quinolin-6-yloxy]-pentyl}-methyl-amine (70%) as light yellow oil, MS: 462 (M, 1Cl).

3.8

To 60.4 mg (0.2 mmol) Allyl-methyl-[6-(1,2,3,4-tetrahydro-quinolin-6-yloxy)-hexyl]-amine in 2 ml $CH_2Cl_2$ 1 drop of Huenig's base and 57 mg (0.3 mmol) 4-chlorophenyl chloroformate in 1 ml $CH_2Cl_2$ were added. The solution was stirred at RT for 30 min, was concentrated and the residue was dissolved in ether and a saturated aqueous solution of $NaHCO_3$. The inorganic phase was extracted with ether and the combined organic phases were washed with water and dried over $Na_2SO_4$. Column chromatography on silica gel with $CH_2Cl_2$/MeOH 19:1 yielded 46 mg (50%) 6-[6-(Allyl-methyl-amino)-hexyloxy]-3,4-dihydro-2H-quinoline-1-carboxylic acid 4-chloro-phenyl ester as colorless oil, MS: 457 ($MH^+$, 1Cl).

3.9

To 70 mg (0.25 mmol) Diethyl-[4-(1,2,3,4-tetrahydro-quinolin-6-yloxy)-butyl]-amine in 1.4 ml DMF 87 μl (0.5 mmol) Huenig's base and 54 μl (0.38 mmol) benzyl chloroformate were added. The solution was stirred at RT over night, was concentrated and the residue was dissolved in ether and 0.1M NaOH. The inorganic phase was extracted with ether and the combined organic phases were washed with water and dried over $Na_2SO_4$. Column chromatography on silica gel with $CH_2Cl_2$MeOH 5:1 yielded 40 mg (38%) 6-(4-Diethylamino-butoxy)-3,4-dihydro-2H-quinoline-1-carboxylic acid benzyl ester as light yellow oil, MS: 411 ($MH^+$).

3.10

In analogy to example 3.9, Diethyl-[4-(1,2,3,4-tetrahydro-quinolin-6-yloxy)-butyl]-amine and 4-chlorophenyl chloroformate were converted to yield 6-(4-Diethylamino-butoxy)-3,4-dihydro-2H-quinoline-1-carboxylic acid 4-chloro-phenyl ester as colorless oil, MS: 431 ($MH^+$, 1Cl).

3.11

In analogy to example 3.9, Diethyl-[4-(1,2,3,4-tetrahydro-quinolin-6-yloxy)-butyl]-amine and hexylchloroformate were converted to yield 6-(4-Diethylamino-butoxy)-3,4-dihydro-2H-quinoline-1-carboxylic acid hexyl ester as colorless oil, MS: 405 ($MH^+$).

3.12

In analogy to example 3.9, Diethyl-[4-(1,2,3,4-tetrahydro-quinolin-6-yloxy)-butyl]-amine and 4-bromophenyl chloroformate were converted to yield 6-(4-

Diethylamino-butoxy)-3,4-dihydro-2H-quinoline-1-carboxylic acid 4-bromo-phenyl ester as colorless oil, MS: 475 (MH$^+$, 1Br).

3.13

In analogy to example 3.9, Diethyl-[4-(1,2,3,4-tetrahydro-quinolin-6-yloxy)-butyl]-amine and 4-fluorophenylchloroformate were converted to yield 6-(4-Diethylamino-butoxy)-3,4-dihydro-2H-quinoline-1-carboxylic acid 4-fluoro-phenyl ester as colorless oil, MS: 415 (MH$^+$).

3.14

In analogy to example 3.9, Allyl-methyl-[4-(1,2,3,4-tetrahydro-quinolin-6-yloxy)-but-2-enyl]-amine and ethylchloroformate were converted to yield 6-[4-(Allyl-methyl-amino)-but-2-enyloxy]-3,4-dihydro-2H-quinoline-1-carboxylic acid ethyl ester as brown oil, MS: 345 (MH$^+$).

Example 4

4.1

To 1.0 g (4 mmol) 6-Hydroxy-3,4-dihydro-2H-quinoline-1-carboxylic acid tert-butyl ester in 2.5 ml pyridine 0.72 ml (43.6 mmol) trifluoromethanesulfonic anhydride was added at 0° C. and the mixture was stirred at RT over night. Water and Et$_2$O were added, and the inorganic phase was extracted with Et$_2$O. The combined organic phases were washed with 2M HCl and water, and dried over Na$_2$SO$_4$. Column chromatography on silica gel with hexane yielded 850 mg (56%) 6-Trifluoromethanesulfonyloxy-3,4-dihydro-2H-quinoline-1-carboxylic acid tert-butyl ester as yellow solid, MS: 381 (M).

4.2

To 850 mg (2.2 mmol) 6-Trifluoromethanesulfonyloxy-3,4-dihydro-2H-quinoline-1-carboxylic acid tert-butyl ester in 5 ml piperidine, 128.0 mg (0.1 mmol) tetrakis(triphenylphosphine)palladium followed by 21.0 mg (0.1 mmol) copper iodide were added. The solution was evaporated and flushed with argon prior to the addition of 210 µl (2.2 mmol) 4-pentynol at 80° C. over a period of 45 min. Further 0.2 ml (2.1 mmol) 4-pentynol were added and the solution was stirred for 2 h. The mixture was added to ice water, acidified with 2M HCl and extracted with ether. The combined organic phases were washed with water and dried over Na$_2$SO$_4$. Purification by column chromatography with CH$_2$Cl$_2$/MeOH 30:1 yielded 650 mg (92%) 6-(5-Hydroxy-pent-1-ynyl)-3,4-dihydro-2H-quinoline-1-carboxylic acid tert-butyl ester as light brown oil, MS: 316 (MH$^+$).

4.3

850 mg (2.7 mmol) 6-(5-Hydroxy-pent-1-ynyl)-3,4-dihydro-2H-quinoline-1-carboxylic acid tert-butyl ester in 30 ml ethanol were hydrogenated in the presence of 10% Pd/C over night. Purification by column chromatography yielded 450 mg (68%) 6-(5-Hydroxy-pentyl)-3,4-dihydro-2H-quinoline-1-carboxylic acid tert-butyl ester as yellow oil, MS: 319 (M).

4.4

To 450 mg (1.43 mmol) 6-(5-Hydroxy-pentyl)-3,4-dihydro-2H-quinoline-1-carboxylic acid tert-butyl ester in 15 ml CH$_2$Cl$_2$ 0.15 ml (1.9 mmol) methanesulfonyl chloride and 0.63 ml (4.5 mmol) triethylamine were added at 0° C. The solution was stirred at RT for 2 h, was diluted with CH$_2$Cl$_2$, and 1M HCl was added. The inorganic layer was extracted with CH$_2$Cl$_2$ and the combined organic phases were washed with water and dried over Na$_2$SO$_4$. Purification by column chromatography with CH$_2$Cl$_2$/MeOH 30:1 yielded 560 mg (98%) 6-(5-Methanesulfonyloxy-pentyl)-3,4-dihydro-2H-quinoline-1-carboxylic acid tert-butyl ester as yellow oil, MS: 397 (M).

4.5

To 560 mg (1.4 mmol) 6-(5-Methanesulfonyloxy-pentyl)-3,4-dihydro-2H-quinoline-1-carboxylic acid tert-butyl ester in 5 ml DMF were added 2.5 ml (26.0 mmol) N-allylmethylamine. The solution was stirred at 70° C. for 2 h, concentrated and dissolved in water and CH$_2$Cl$_2$. 2M NaOH was added and the inorganic phase was extracted with CH$_2$Cl$_2$. The organic phase was washed with water and dried over Na$_2$SO$_4$. Purification by column chromatography with CH$_2$Cl$_2$/MeOH 20:1 yielded 470 mg (89%) 6-[5-(Allyl-methyl-amino)-pentyl]-3,4-dihydro-2H-quinoline-1-carboxylic acid tert-butyl ester as yellow oil, MS: 373 (MH$^+$).

4.6

Treatment of 6-[5-(Allyl-methyl-amino)-pentyl]-3,4-dihydro-2H-quinoline-1-carboxylic acid tert-butyl ester with TFA in analogy to example 3.1 yielded Allyl-methyl-[5-(1,2,3,4-tetrahydro-quinolin-6-yl)-pentyl]-amine as yellow oil, MS: 272 (M).

4.7

Reaction of Allyl-methyl-[5-(1,2,3,4-tetrahydro-quinolin-6-yl)-pentyl]-amine with 4-Chlorobenzene-sulfonylchloride in analogy to example 3.6 yielded Allyl-{5-[1-(4-chloro-benzenesulfonyl)-1,2,3,4-tetrahydro-quinolin-6-yl]-pentyl}-methyl-amine as light yellow oil, MS: 447 (M$^+$, 1Cl);

4.8

Treatment of Allyl-methyl-[5-(1,2,3,4-tetrahydro-quinolin-6-yl)-pentyl]-amine with 4-Bromobenzolsulfonylchloride in analogy to example 3.6 yielded Allyl-{5-[1-(4-bromo-benzenesulfonyl)-1,2,3,4-tetrahydro-quinolin-6-yl]-pentyl}-methyl-amine as light brown oil, MS: 491 (MH$^+$, 1Br).

Example 5

5.1

In analogy to the method described by Gordon W. Gribble, Joseph H. Hoffmann Synthesis 1977, 859–860, the following reaction was performed. To a precooled solution of 22.3 g (0.1 mol) 5-benzyloxyindole in 270 ml acetic acid, 19 g (0.3 mol) NaCNBH$_3$ were added. The solution was stirred at RT for 2 h, the volume was reduced to one third and poured into 300 ml water. KOH was added under cooling and the solution was extracted with ether. The combined organic phases were washed with water, dried over Na$_2$SO$_4$ and evaporated to yield 20.1 g (89%) 5-Benzyloxy-2,3-dihydro-1H-indole as colorless oil, MS: 225 (M).

5.2

20 g (89 mmol) 5-Benzyloxy-2,3-dihydro-1H-indole in 250 ml CH$_2$Cl$_2$ were treated with 20 g (91.6 mmol) di-tert.-butyldicarbonate at 0° C. for 1 h and at RT for 1 h. The mixture was concentrated and extracted with ether and 0.5 M HCl. The organic phase was washed with water and dried over Na$_2$SO$_4$. Trituration of the crude material with hexane yielded 23 g (71%) 5-Benzyloxy-2,3-dihydro-indole-1-carboxylic acid tert-butyl ester as colorless solid, MS: 325 (M).

5.3

23 g (68.6 mmol) 5-Benzyloxy-2,3-dihydro-indole-1-carboxylic acid tert-butyl ester in 250 ml methanol were hydrogenated with 2.5 g 10% Pd/C for 2 h. The suspension was filtered and the filtrate was concentrated and purified by column chromatography on silica gel with MeOH/EtOAc 1:1 yielding 14.4 g (90%) 5-Hydroxy-2,3-dihydro-indole-1-carboxylic acid tert-butyl ester as colorless solid, MS: 235 (M).

5.4

514 mg (2.3 mmol) 5-Hydroxy-2,3-dihydro-indole-1-carboxylic acid tert-butyl ester in 12 ml DMF were treated with 830 mg (6 mmol) powdered K$_2$CO$_3$ and 1070 mg (5 mmol) 1,4-dibromobutene. The suspension was stirred at 50° C. for 3 h, cooled to RT, diluted with ether and water. The aqueous phase was extracted with ether, the organic phases were washed with water and dried over $Na_2SO_4$. Column chromatography on silica gel with hexane/EtOAc 9:1 yielded 270 mg (31%) 5-(4-Bromo-but-2-enyloxy)-2,3-dihydro-indole-1-carboxylic acid tert-butyl ester as colorless solid, MS: 368 ($MH^+$, 1Br).

5.5

214 mg (0.6 mmol) 5-(4-Bromo-but-2-enyloxy)-2,3-dihydro-indole-1-carboxylic acid tert-butyl ester in 3 ml DMF were treated with 213 mg (3 mmol) N-allylmethylamine at 50° C. for 0.5 h. The mixture was extracted with ether and water. The organic phase was washed with water and dried over $Na_2SO_4$ and evaporated to yield 180 mg (83%) 5-[4-(Allyl-methyl-amino)-but-2-enyloxy]-2,3-dihydro-indole-1-carboxylic acid tert-butyl ester as yellow oil, MS: 359 ($MH^+$).

Example 6

6.1

Hydrogenation of 2.23 g (10 mmol) 5-benzyloxyindole in 25 ml acetic acid and 25 ml methanol with 500 mg 10% Pd/C yielded 2 g crude 2,3-Dihydro-1H-indol-5-ol.

6.2

To 0.7 g (5 mmol) 2,3-Dihydro-1H-indol-5-ol in 10 ml THF, 1.7 ml (10 mmol) N,N-diisopropylethylamine and 0.5 ml (3.6 mmol) 4-chlorophenyl-chloroformate were added at 0° C. The solution was stirred at RT for 1 h and concentrated in vacuo. The residue was redissolved in ether/1M HCl, the inorganic phase was extracted with ether and the combined organic phases were washed with water and dried over $Na_2SO_4$. Evaporation yielded 420 mg (29%) 5-Hydroxy-2,3-dihydro-indole-1-carboxylic acid 4-chloro-phenyl ester as colorless solid, MS: 289 (M, 1Cl).

6.3

290 mg (1 mmol) 5-Hydroxy-2,3-dihydro-indole-1-carboxylic acid 4-chloro-phenyl ester in 5 ml acetone were treated with 320 mg (3 mmol) $K_2CO_3$ (powdered) and 0.23 ml (2 mmol) 1,4-dibromobutane. The suspension was stirred at 50° C. for 4 h, cooled to RT, and was diluted with ether and water. The aqueous phase was extracted with ether, the organic phases were washed with water and dried over $Na_2SO_4$. Column chromatography on silica gel with hexane/EtOAc 9:1 yielded 210 mg (49%) 5-(4-Bromo-butoxy)-2,3-dihydro-indole-1-carboxylic acid 4-chloro-phenyl ester as colorless solid, MS: 423 (M, 1Br, 1Cl).

6.4

106 mg (0.25 mmol) 5-(4-Bromo-butoxy)-2,3-dihydro-indole-1-carboxylic acid 4-chloro-phenyl ester in 2 ml DMF were treated with 71 mg (1 mmol) N-allylmethylamine at 50° C. for 2 h. The mixture was concentrated and purified by column chromatography on silica gel with $CH_2Cl_2$/MeOH 19:1 to give 68 mg (66%) 5-[4-(Allyl-methyl-amino)-butoxy]-2,3-dihydro-indole-1-carboxylic acid 4-chloro-phenyl ester as colorless solid, MS: 415 ($M^+$, 1Cl).

Example 7

7.1

9.41 g (40 mmol) 5-Hydroxy-2,3-dihydro-indole-1-carboxylic acid tert-butyl ester in 90 ml acetone were treated with 16.6 g (6 mmol) $K_2CO_3$ (powdered) and 17.3 g (5 mmol) 1,4-dibromobutane. The suspension was stirred at 50° C. for 4 h, cooled to RT, filtered and concentrated. Column chromatography on silica gel with $CH_2Cl_2$ yielded 8.8 g (60%) 5-(4-Bromo-butoxy)-2,3-dihydro-indole-1-carboxylic acid tert-butyl ester as colorless solid, MS: 370 ($MH^+$, 1Br).

7.2

8.8 g (24 mmol) 5-(4-Bromo-butoxy)-2,3-dihydro-indole-1-carboxylic acid tert-butyl ester in 10 ml DMF were treated with 7.11 g (100 mmol) N-allylmethylamine at 50° C. for 4 h. The solution was concentrated in vacuo and the residue was redissolved in ether and water. 2M NaOH was added and the inorganic phase was extracted with ether. The combined organic phases were washed with water, dried over $Na_2SO_4$ and evaporated. Column chromatography with a gradient of $CH_2Cl_2$/MeOH 19:1 to 9:1 yielded 7.4 g (85%) 5-[4-(Allyl-methyl-amino)-butoxy]-2,3-dihydro-indole-1-carboxylic acid tert-butyl ester as colorless oil, MS: 361 ($MH^+$).

7.3

In analogy to example 7.2, 5-(4-Bromo-butoxy)-2,3-dihydro-indole-1-carboxylic acid tert-butyl ester and methoxyethyl-ethylamine were converted to yield 5-{4-[(2-Methoxy-ethyl)-methyl-amino]-butoxy}-2,3-dihydro-indole-1-carboxylic acid tert-butyl ester as colorless oil, MS: 379 ($MH^+$).

7.4

In analogy to example 7.2, 5-(4-Bromo-butoxy)-2,3-dihydro-indole-1-carboxylic acid tert-butyl ester and ethylaminoethanol were converted to yield 5-{4-[Ethyl-(2-hydroxy-ethyl)-amino]-butoxy}-2,3-dihydro-indole-1-carboxylic acid tert-butyl ester as yellow oil, MS: 379 ($MH^+$).

7.5

To 7.3 g (20.2 mmol) 5-[4-(Allyl-methyl-amino)-butoxy]-2,3-dihydro-indole-1-carboxylic acid tert-butyl ester in 15 ml $CH_2Cl_2$ 10 ml trifluoroacetic acid were added at 0° C. The mixture was stirred at reflux for 3 h and was concentrated in vacuo. Water and 2M NaOH were added and the inorganic phase was extracted with ether. The combined organic phases were washed with water and dried over $Na_2SO_4$. Evaporation yielded 5.2 g (98%) Allyl-[4-(2,3-dihydro-1H-indol-5-yloxy)-butyl]-methyl-amine as orange oil, MS: 261 ($MH^+$).

7.6

In analogy to example 7.5, 5-{4-[(2-Methoxy-ethyl)-methyl-amino]-butoxy}-2,3-dihydro-indole-1-carboxylic acid tert-butyl ester was converted to yield [4-(2,3-Dihydro-1H-indol-5-yloxy)-butyl]-(2-methoxy-ethyl)-methyl-amine as light brown oil, MS: 279 ($MH^+$).

7.7

In analogy to example 7.5, 5-{4-[Ethyl-(2-hydroxy-ethyl)-amino]-butoxy}-2,3-dihydro-indole-1-carboxylic acid tert-butyl ester was converted to yield 2-{[4-(2,3-Dihydro-1H-indol-5-yloxy)-butyl]-ethyl-amino}-ethanol as light yellow oil, MS: 279 ($MH^+$).

7.8

220 mg (0.8 mmol) [4-(2,3-Dihydro-1H-indol-5-yloxy)-butyl]-(2-methoxy-ethyl)-methyl-amine in 0.5 ml dioxane were treated with 186 mg (0.9 mmol) chloro-thioformic acid (4-chloro-phenyl)ester in 0.5 ml dioxane at 0° C. The solution was stirred at RT for 3 h, was diluted with water and ether and a saturated aqueous solution of $NaHCO_3$ was added. The inorganic layer was extracted with ether, washed with water and dried over $Na_2SO_4$. Column chromatography with $CH_2Cl_2$/MeOH 19:1 yielded 230 mg (64%) 5-{4-[(2-Methoxy-ethyl)-methyl-amino]-butoxy}-2,3-dihydro-indole-1-carbothioic acid O-(4-chloro-phenyl)ester as yellow viscous oil, MS: 449 ($MH^+$, 1Cl).

7.9

In analogy to example 7.8, 2-{[4-(2,3-Dihydro-1H-indol-5-yloxy)-butyl]-ethyl amino}-ethanol and chloro-thioformic acid (4-chloro-phenyl)ester were converted to yield 5-{4-

[Ethyl-(2-hydroxy-ethyl)-amino]-butoxy}-2,3-dihydro-indole-1-carbothioic acid O-(4-chloro-phenyl)ester as yellow viscous oil, MS: 449 (MH$^+$, 1Cl).

7.10

In analogy to example 7.8, Allyl-[4-(2,3-dihydro-1H-indol-5-yloxy)-butyl]-methyl-amine and chloro-thioformic acid (4-chloro-phenyl)ester were converted to yield 5-[4-(Allyl-methyl-amino)-butoxy]-2,3-dihydro-indole-1-carbothioic acid O-(4-chloro-phenyl)ester as light grey waxy solid, MS: 431 (MH$^+$, 1Cl).

7.11

In analogy to example 7.8, Allyl-[4-(2,3-dihydro-1H-indol-5-yloxy)-butyl]-methyl-amine and chloro-thioformic acid (4-chloro-phenyl)ester were converted to yield 5-[4-(Allyl-methyl-amino)-butoxy]-2,3-dihydro-indole-1-carbothioic acid O-(4-fluoro-phenyl)ester as light yellow viscous oil, MS: 415 (MH$^+$).

Example 8

8.1

4 g (20 mmol) 5-bromo-indoline in 50 ml CH$_2$Cl$_2$ were treated with 4.4 g (20 mmol) di.-tert.-butyldicarbonate at RT over night. The reaction mixture was concentrated in vacuo and triturated with hexane to yield 5.3 g (89%) 5-Bromo-2,3-dihydro-indole-1-carboxylic acid tert-butyl ester as colorless solid, MS: 297 (M, 1Br).

8.2

To 3.73 g (12.5 mmol) 5-Bromo-2,3-dihydro-indole-1-carboxylic acid tert-butyl ester in 25 ml piperidine 722 mg (0.63 mmol) tetrakis-(triphenylphosphine)-palladium and 120 mg (0.625 mmol) CuI were added. The solution was purged with argon and was heated to 80° C. over a period of 45 min, during which 0.9 ml (9.4 mmol) 4-pentynol were added. Additional 0.9 ml (9.4 mmol) 4-pentynol were added and the mixture was stirred for 2 h, poured into ice water and 2M HCl was added. The inorganic phase was extracted with ether, the combined organic phases were washed with water and dried over Na$_2$SO$_4$. Purification on silica gel with hexane/EtOAc 4:1 to 2:1 yielded 3.0 g (79%) 5-(5-Hydroxy-pent-1-ynyl)-2,3-dihydro-indole-1-carboxylic acid tert-butyl ester as light brown solid, MS: 302 (MH$^+$). (See also: Stara, Irena G.; Stary, Ivo; Kollarovic, Adrian; Teply, Filip; Saman, David; Fiedler, Pavel. Coupling reactions of halobenzenes with alkynes. The synthesis of phenylacetylenes and symmetrical or unsymmetrical 1,2-diphenylacetylenes. Collect. Czech. Chem. Commun. (1999), 64(4), 649–672)

8.3

2.8 g (9.3 mmol) 5-(5-Hydroxy-pent-1-ynyl)-2,3-dihydro-indole-1-carboxylic acid tert-butyl ester in 60 ml MeOH were subjected to hydrogenation with 10% Pd/C to yield 2.8 g (quantitative) 5-(5-Hydroxy-pentyl)-2,3-dihydro-indole-1-carboxylic acid tert-butyl ester as colorless viscous oil, MS: 305 (M).

8.4

To 2.75 g (9 mmol) 5-(5-Hydroxy-pentyl)-2,3-dihydro-indole-1-carboxylic acid tert-butyl ester in 100 ml CH$_2$Cl$_2$, 0.87 ml (11 mmol) methanesulfonyl chloride and 3.8 ml (27 mmol) triethylamine were added at 0° C. The solution was concentrated in vacuo to yield crude 5-(5-Methanesulfonyloxy-pentyl)-2,3-dihydro-indole-1-carboxylic acid tert-butyl ester as yellow viscous oil, MS: 384 (MH$^+$). The crude material was dissolved in 5 ml DMF and 5 ml (50 mmol) N-allylmethylamine. The mixture was heated to 80° C. for 3 h, concentrated and the residue was dissolved in water and ether, 2M NaOH was added and the inorganic phase was extracted with ether. The combined organic phases were washed with water and dried over Na$_2$SO$_4$. Column chromatography on silica gel with CH$_2$Cl$_2$: MeOH 9:1 yielded 2.5 g (72%) 5-[5-(Allyl-methyl-amino)-pentyl]-2,3-dihydro-indole-1-carboxylic acid tert-butyl ester as colorless liquid, MS: 359 (MH$^+$).

8.5

2.45 g (6.8 mmol) 5-[5-(Allyl-methyl-amino)-pentyl]-2,3-dihydro-indole-1-carboxylic acid tert-butyl ester in 5 ml CH$_2$Cl$_2$ were treated with 4 ml TFA at 0° C. The solution was stirred at RT for 0.5 h, and at 40° C. for 1 h. The solution was concentrated and the residue was dissolved in ether and water. 2M NaOH was added and the inorganic phase was extracted with ether. The combined organic phases were washed with water and dried over Na$_2$SO$_4$ to yield 1.65 g (94%) Allyl-[5-(2,3-dihydro-1H-indol-5-yl)-pentyl]-methyl-amine as light yellow oil, MS: 259 (MH$^+$).

8.6

To 130 mg (0.5 mmol) Allyl-[5-(2,3-dihydro-1H-indol-5-yl)-pentyl]-methyl-amine in 2 ml CH$_2$Cl$_2$ 0.34 ml (2 mmol) Huenig's base were added, followed by 0.28 ml (2 mmol) 4-chlorophenyl chloroformate. The solution was stirred at RT for 30 min, was concentrated and dissolved in 0.1 M NaOH and ether. The inorganic phase was extracted with ether. The combined organic phases were washed with water and dried over Na$_2$SO$_4$. Column chromatography on silica gel with CH$_2$Cl$_2$/MeOH 9:1 yielded 160 mg (77%) 5-[5-(Allyl-methyl-amino)-pentyl]-2,3-dihydro-indole-1-carboxylic acid 4-chloro-phenyl ester as light yellow oil, MS: 413 (MH$^+$, 1Cl).

8.7

130 mg (0.5 mmol) Allyl-[5-(2,3-dihydro-1H-indol-5-yl)-pentyl]-methyl-amine in 0.5 ml dioxane were treated with 0.072 ml (0.5 mmol) chlorothio-formicacid-O-(4-chlorophenyl)-ester at 15° C. The mixture was stirred for 15 min, concentrated and purified by column chromatography on silica gel with a gradient of CH$_2$Cl$_2$MeOH 99:1 to 97:3 to yield 92 mg 5-[5-(Allyl-methyl-amino)-pentyl]-2,3-dihydro-indole-1-carbothioic acid O-(4-chloro-phenyl)ester as colorless oil. The corresponding acetic acid salt was prepared by treatment with acetic acid in CH$_2$Cl$_2$ to yield 101 mg 5-[5-(Allyl-methyl-amino)-pentyl]-2,3-dihydro-indole-1-carbothioic acid O-(4-chloro-phenyl)esteracetic acid as light brown viscous oil, MS: 429 (MH$^+$, 1Cl).

Example 9

A solution of 0.153 mmol of the corresponding amine in 0.35 ml dry dioxane was treated with 0.23 mmol of the corresponding isocyanate in 0.54 ml dry dioxane. The solution was allowed to stand at room temperature over night. The resulting reaction mixture was treated with 0.15 ml formic acid and purified by preparative HPLC [RP-18, acetonitrile (0.1% HCOOH)/water (0.1% HCOOH), 10% to 95% acetonitrile]. After evaporation the resulting compound was obtained as amino formate.

| No. | Compound | MS MH+ | Amine | Isocyanate |
|---|---|---|---|---|
| 9.1 | 5-[4-(Allyl-methyl-amino)-butoxy]-2,3-dihydro-indole-1-carboxylic acid (2,4-difluoro-phenyl)-amide | 416 | Allyl-[4-(2,3-dihydro-1H-indol-5-yloxy)-butyl]-methyl-amine | 2,4 Difluorophenyl-isocyanate |
| 9.2 | 5-[4-(Allyl-methyl-amino)-butoxy]-2,3-dihydro-indole-1-carboxylic acid (4-fluoro-phenyl)-amide | 398 | Allyl-[4-(2,3-dihydro-1H-indol-5-yloxy)-butyl]-methyl-amine | 4-Fluorophenyl-isocyanate |
| 9.3 | 5-[4-(Allyl-methyl-amino)-butoxy]-2,3-dihydro-indole-1-carboxylic acid p-tolylamide | 394 | Allyl-[4-(2,3-dihydro-1H-indol-5-yloxy)-butyl]-methyl-amine | 4-Methylphenyl-isocyanate |
| 9.4 | 5-[4-(Allyl-methyl-amino)-butoxy]-2,3-dihydro-indole-1-carboxylic acid (4-bromo-phenyl)-amide | 458 (1 Br) | Allyl-[4-(2,3-dihydro-1H-indol-5-yloxy)-butyl]-methyl-amine | 4-Bromophenyl-isocyanate |
| 9.5 | 5-[4-(Allyl-methyl-amino)-butoxy]-2,3-dihydro-indole-1-carboxylic acid (2,4-dimethoxy-phenyl)-amide | 440 | Allyl-[4-(2,3-dihydro-1H-indol-5-yloxy)-butyl]-methyl-amine | 2,4-Dimethoxy-phenyl-isocyanate |
| 9.6 | 5-[4-(Allyl-methyl-amino)-butoxy]-2,3-dihydro-indole-1-carboxylic acid (4-methoxy-phenyl)-amide | 410 | Allyl-[4-(2,3-dihydro-1H-indol-5-yloxy)-butyl]-methyl-amine | 4-Methoxyphenyl-isocyanate |
| 9.7 | 5-[4-(Allyl-methyl-amino)-butoxy]-2,3-dihydro-indole-1-carboxylic acid naphthalen-2-ylamide | 430 | Allyl-[4-(2,3-dihydro-1H-indol-5-yloxy)-butyl]-methyl-amine | 2-Naphthylphenyl-isocyanate |
| 9.8 | 5-[4-(Allyl-methyl-amino)-butoxy]-2,3-dihydro-indole-1-carboxylic acid (4-acetyl-phenyl)-amide | 422 | Allyl-[4-(2,3-dihydro-1H-indol-5-yloxy)-butyl]-methyl-amine | 4-Acetylphenyl-isocyanate |
| 9.9 | 5-[5-(Allyl-methyl-amino)-pentyl]-2,3-dihydro-indole-1-carboxylic acid (2,4-difluoro-phenyl)-amide | 414 | Allyl-[5-(2,3-dihydro-1H-indol-5-yl)-pentyl]-methyl-amine | 2,4-Difluorophenyl-isocyanate |
| 9.10 | 5-[5-(Allyl-methyl-amino)-pentyl]-2,3-dihydro-indole-1-carboxylic acid (4-fluoro-phenyl)-amide | 396 | Allyl-[5-(2,3-dihydro-1H-indol-5-yl)-pentyl]-methyl-amine | 4-Fluorophenyl-isocyanate |
| 9.11 | 5-[5-(Allyl-methyl-amino)-pentyl]-2,3-dihydro-indole-1-carboxylic acid p-tolylamide | 392 | Allyl-[5-(2,3-dihydro-1H-indol-5-yl)-pentyl]-methyl-amine | 4-Methylphenyl-isocyanate |
| 9.12 | 5-[5-(Allyl-methyl-amino)-pentyl]-2,3-dihydro-indole-1-carboxylic acid (4-bromo-phenyl)-amide | 456 (1 Br) | Allyl-[5-(2,3-dihydro-1H-indol-5-yl)-pentyl]-methyl-amine | 4-Bromophenyl-isocyanate |
| 9.13 | 5-[5-(Allyl-methyl-amino)-pentyl]-2,3-dihydro-indole-1-carboxylic acid (2,4-dimethoxy-phenyl)-amide | 438 | Allyl-[5-(2,3-dihydro-1H-indol-5-yl)-pentyl]-methyl-amine | 2,4-Dimethoxy-phenyl-isocyanate |
| 9.14 | 5-[5-(Allyl-methyl-amino)-pentyl]-2,3-dihydro-indole-1-carboxylic acid (4-methoxy-phenyl)-amide | 408 | Allyl-[5-(2,3-dihydro-1H-indol-5-yl)-pentyl]-methyl-amine | 4-Methoxyphenyl-isocyanate |
| 9.15 | 5-[5-(Allyl-methyl-amino)-pentyl]-2,3-dihydro-indole-1-carboxylic acid naphthalen-2-ylamide | 428 | Allyl-[5-(2,3-dihydro-1H-indol-5-yl)-pentyl]-methyl-amine | 2-Naphthylphenyl-isocyanate |
| 9.16 | 5-[5-(Allyl-methyl-amino)-pentyl]-2,3-dihydro-indole-1-carboxylic acid (4-acetyl-phenyl)-amide | 420 | Allyl-[5-(2,3-dihydro-1H-indol-5-yl)-pentyl]-methyl-amine | 4-Acetylphenyl-isocyanate |
| 9.17 | 6-[4-(Allyl-methyl-amino)-but-2-enyloxy]-3,4-dihydro-2H-quinoline-1-carboxylic acid (4-acetyl-phenyl)-amide | 434 | Allyl-methyl-[4-(1,2,3,4-tetrahydro-quinolin-6-yloxy)-but-2-enyl]-amine | 4-Acetylphenyl-isocyanate |
| 9.18 | 6-[4-(Allyl-methyl-amino)-but-2-enyloxy]-3,4-dihydro-2H-quinoline-1-carboxylic acid (4-methoxy-phenyl)-amide | 422.3 | Allyl-methyl-[4-(1,2,3,4-tetrahydro-quinolin-6-yloxy)-but-2-enyl]-amine | 4-Methoxyphenyl-isocyanate |

-continued

| No. | Compound | MS MH+ | Amine | Isocyanate |
|---|---|---|---|---|
| 9.19 | 6-[4-(Allyl-methyl-amino)-but-2-enyloxy]-3,4-dihydro-2H-quinoline-1-carboxylic acid p-tolylamide | 406.3 | Allyl-methyl-[4-(1,2,3,4-tetrahydro-quinolin-6-yloxy)-but-2-enyl]-amine | P-Tolyl-isocyanate |
| 9.20 | 6-[4-(Allyl-methyl-amino)-but-2-enyloxy]-3,4-dihydro-2H-quinoline-1-carboxylic acid naphthalen-1-ylamide | 442.3 | Allyl-methyl-[4-(1,2,3,4-tetrahydro-quinolin-6-yloxy)-but-2-enyl]-amine | 1-Naphthyl-isocyanate |
| 9.21 | 6-[4-(Allyl-methyl-amino)-but-2-enyloxy]-3,4-dihydro-2H-quinoline-1-carboxylic acid (2,4-difluoro-phenyl)-amide | 428.3 | Allyl-methyl-[4-(1,2,3,4-tetrahydro-quinolin-6-yloxy)-but-2-enyl]-amine | 2,4-Difluorophenyl-isocyanate |
| 9.22 | 6-[4-(Allyl-methyl-amino)-but-2-enyloxy]-3,4-dihydro-2H-quinoline-1-carboxylic acid (4-fluoro-3-trifluoromethyl-phenyl)-amide | 478.2 | Allyl-methyl-[4-(1,2,3,4-tetrahydro-quinolin-6-yloxy)-but-2-enyl]-amine | 4-Fluoro-3-Trifluoromethyl-Phenyl-isocyanate |
| 9.23 | 6-[4-(Allyl-methyl-amino)-but-2-enyloxy]-3,4-dihydro-2H-quinoline-1-carboxylic acid (4-fluoro-phenyl)-amide | 410.2 | Allyl-methyl-[4-(1,2,3,4-tetrahydro-quinolin-6-yloxy)-but-2-enyl]-amine | 4-Fluorophenyl-isocyanate |
| 9.24 | 6-[4-(Allyl-methyl-amino)-but-2-enyloxy]-3,4-dihydro-2H-quinoline-1-carboxylic acid (2,4-dimethoxy-phenyl)-amide | 452.3 | Allyl-methyl-[4-(1,2,3,4-tetrahydro-quinolin-6-yloxy)-but-2-enyl]-amine | 2,4-Dimethoxy-phenyl-isocyanate |
| 9.25 | 6-[4-(Allyl-methyl-amino)-but-2-enyloxy]-3,4-dihydro-2H-quinoline-1-carboxylic acid (4-methylsulfanyl-phenyl)-amide | 438.3 | Allyl-methyl-[4-(1,2,3,4-tetrahydro-quinolin-6-yloxy)-but-2-enyl]-amine | 4-(Methylthio)-phenyl-isocyanate |
| 9.26 | 6-[4-(Allyl-methyl-amino)-but-2-enyloxy]-3,4-dihydro-2H-quinoline-1-carboxylic acid (4-bromo-phenyl)-amide | 470.1 (1 Br) | Allyl-methyl-[4-(1,2,3,4-tetrahydro-quinolin-6-yloxy)-but-2-enyl]-amine | 4-Bromophenyl-isocyanate |
| 9.27 | 6-[4-(Allyl-methyl-amino)-but-2-enyloxy]-3,4-dihydro-2H-quinoline-1-carboxylic acid benzylamide | 406.3 | Allyl-methyl-[4-(1,2,3,4-tetrahydro-quinolin-6-yloxy)-but-2-enyl]-amine | Benzyl-isocyanate |
| 9.28 | 6-[4-(Allyl-methyl-amino)-but-2-enyloxy]-3,4-dihydro-2H-quinoline-1-carboxylic acid (4-butyl-phenyl)-amide | 448.2 | Allyl-methyl-[4-(1,2,3,4-tetrahydro-quinolin-6-yloxy)-but-2-enyl]-amine | 4-N-Butylphenyl-isocyanate |
| 9.29 | 6-[4-(Allyl-methyl-amino)-but-2-enyloxy]-3,4-dihydro-2H-quinoline-1-carboxylic acid phenethyl-amide | 420 | Allyl-methyl-[4-(1,2,3,4-tetrahydro-quinolin-6-yloxy)-but-2-enyl]-amine | Phenethyl-isocyanate |
| 9.30 | 6-[6-(Allyl-methyl-amino)-hexyloxy]-3,4-dihydro-2H-quinoline-1-carboxylic acid p-tolylamide | 436 | Allyl-methyl-[6-(1,2,3,4-tetrahydro-quinolin-6-yloxy)-hexyl]-amine | 4-Tolyl-isocyanate |
| 9.31 | 6-[6-(Allyl-methyl-amino)-hexyloxy]-3,4-dihydro-2H-quinoline-1-carboxylic acid (4-fluoro-phenyl)-amide | 440 | Allyl-methyl-[6-(1,2,3,4-tetrahydro-quinolin-6-yloxy)-hexyl]-amine | 4-Fluorophenyl-isocyanate |
| 9.32 | 6-[6-(Allyl-methyl-amino)-hexyloxy]-3,4-dihydro-2H-quinoline-1-carboxylic acid (4-bromo-phenyl)-amide | 500 (1 Br) | Allyl-methyl-[6-(1,2,3,4-tetrahydro-quinolin-6-yloxy)-hexyl]-amine | 4-Bromophenyl-isocyanate |
| 9.33 | 6-[6-(Allyl-methyl-amino)-hexyloxy]-3,4-dihydro-2H-quinoline-1-carboxylic acid (4-butyl-phenyl)-amide | 478 | Allyl-methyl-[6-(1,2,3,4-tetrahydro-quinolin-6-yloxy)-hexyl]-amine | 4-Butylphenyl-isocyanate |
| 9.34 | 6-[4-(Allyl-methyl-amino)-butoxy]-3,4-dihydro-2H-quinoline-1-carboxylic acid (2,4-difluoro-phenyl)-amide | 430 | Allyl-methyl-[4-(1,2,3,4-tetrahydro-quinolin-6-yloxy)-butyl]-amine | 2,4-Difluorophenyl-isocyanate |

-continued

| No. | Compound | MS MH+ | Amine | Isocyanate |
|---|---|---|---|---|
| 9.35 | 6-[4-(Allyl-methyl-amino)-butoxy]-3,4-dihydro-2H-quinoline-1-carboxylic acid (4-fluoro-phenyl)-amide | 412 | Allyl-methyl-[4-(1,2,3,4-tetrahydro-quinolin-6-yloxy)-butyl]-amine | 4-Fluorophenyl-isocyanate |
| 9.36 | 6-[4-(Allyl-methyl-amino)-butoxy]-3,4-dihydro-2H-quinoline-1-carboxylic acid p-tolylamide | 408 | Allyl-methyl-[4-(1,2,3,4-tetrahydro-quinolin-6-yloxy)-butyl]-amine | 4-Methylphenyl-isocyanate |
| 9.37 | 6-[4-(Allyl-methyl-amino)-butoxy]-3,4-dihydro-2H-quinoline-1-carboxylic acid (4-bromo-phenyl)-amide | 472 (1 Br) | Allyl-methyl-[4-(1,2,3,4-tetrahydro-quinolin-6-yloxy)-butyl]-amine | 4-Bromophenyl-isocyanate |
| 9.38 | 6-[4-(Allyl-methyl-amino)-butoxy]-3,4-dihydro-2H-quinoline-1-carboxylic acid (2,4-dimethoxy-phenyl)-amide | 454 | Allyl-methyl-[4-(1,2,3,4-tetrahydro-quinolin-6-yloxy)-butyl]-amine | 2,4-Dimethoxy-phenyl-isocyanate |
| 9.39 | 6-[4-(Allyl-methyl-amino)-butoxy]-3,4-dihydro-2H-quinoline-1-carboxylic acid (4-methoxy-phenyl)-amide | 424 | Allyl-methyl-[4-(1,2,3,4-tetrahydro-quinolin-6-yloxy)-butyl]-amine | 4-Methoxyphenyl-isocyanate |
| 9.40 | 6-[4-(Allyl-methyl-amino)-butoxy]-3,4-dihydro-2H-quinoline-1-carboxylic acid naphthalen-2-ylamide | 444 | Allyl-methyl-[4-(1,2,3,4-tetrahydro-quinolin-6-yloxy)-butyl]-amine | 2-Naphthylphenyl-isocyanate |
| 9.41 | 6-[4-(Allyl-methyl-amino)-butoxy]-3,4-dihydro-2H-quinoline-1-carboxylic acid (4-acetyl-phenyl)-amide | 436 | Allyl-methyl-[4-(1,2,3,4-tetrahydro-quinolin-6-yloxy)-butyl]-amine | 4-Acetylphenyl-isocyanate |
| 9.42 | 6-(4-Diethylamino-butoxy)-3,4-dihydro-2H-quinoline-1-carboxylic acid (4-fluoro-phenyl)-amide | 414 | Diethyl-[4-(1,2,3,4-tetrahydro-quinolin-6-yloxy)-butyl]-amine | 4-Fluorophenyl-isocyanate |
| 9.43 | 6-(4-Diethylamino-butoxy)-3,4-dihydro-2H-quinoline-1-carboxylic acid p-tolylamide | 410 | Diethyl-[4-(1,2,3,4-tetrahydro-quinolin-6-yloxy)-butyl]-amine | 4-Methylphenyl-isocyanate |
| 9.44 | 6-(4-Diethylamino-butoxy)-3,4-dihydro-2H-quinoline-1-carboxylic acid (4-bromo-phenyl)-amide | 474 (1 Br) | Diethyl-[4-(1,2,3,4-tetrahydro-quinolin-6-yloxy)-butyl]-amine | 4-Bromophenyl-isocyanate |

Example 10

A solution of 0.153 mmol of the corresponding amine in 0.35 ml dry dioxane was treated with (0.46 mmol; 3 equivalents) Huenig's base and 0.2 mmol of the corresponding chloroformate in 0.54 ml dry dioxane. The solution was allowed to stand at room temperature over night and the resulting reaction mixture was treated with 0.15 ml formic acid and purified by preparative HPLC [RP-18, acetonitrile (0.1% HCOOH)/water (0.1% HCOOH), 10% to 95% acetonitrile]. After evaporation the resulting compound was obtained as a mixture of amino hydrochloride and formate.

| No. | Compound | MS MH+ | 1. Educt | 2. Educt |
|---|---|---|---|---|
| 10.1 | 6-[4-(allyl-methyl-amino)-but-2-enyloxy]-3,4-dihydro-2H-quinoline-1-carboxylic acid 4-nitro-phenyl ester | 438 | Allyl-methyl-[4-(1,2,3,4-tetrahydro-quinolin-6-yloxy)-but-2-enyl]-amine | 4-Nitrophenyl-chloroformate |
| 10.2 | 6-[4-(Allyl-methyl-amino)-but-2-enyloxy]-3,4-dihydro-2H-quinoline-1-carboxylic acid hexyl ester | 401 | Allyl-methyl-[4-(1,2,3,4-tetrahydro-quinolin-6-yloxy)-but-2-enyl]-amine | Hexyl-chloroformate |
| 10.3 | 6-[4-(Allyl-methyl-amino)-but-2-enyloxy]-3,4-dihydro-2H-quinoline-1-carboxylic acid 4-bromo-phenyl ester | 471 (1 Br) | Allyl-methyl-[4-(1,2,3,4-tetrahydro-quinolin-6-yloxy)-but-2-enyl]-amine | 4-Bromophenyl-chloroformate |
| 10.4 | 6-[4-(Allyl-methyl-amino)-but-2-enyloxy]-3,4- | 373 | Allyl-methyl-[4-(1,2,3,4-tetrahydro- | Isobutyl-chloroformate |

-continued

| No. | Compound | MS MH+ | 1. Educt | 2. Educt |
|---|---|---|---|---|
| | dihydro-2H-quinoline-1-carboxylic acid isobutyl ester | | quinolin-6-yloxy)-but-2-enyl]-amine | |
| 10.5 | 6-[4-(Allyl-methyl-amino)-but-2-enyloxy]-3,4-dihydro-2H-quinoline-1-carboxylic acid phenyl ester | 393 | Allyl-methyl-[4-(1,2,3,4-tetrahydro-quinolin-6-yloxy)-but-2-enyl]-amine | Phenyl-chloroformate |
| 10.6 | 6-[4-(Allyl-methyl-amino)-but-2-enyloxy]-3,4-dihydro-2H-quinoline-1-carboxylic acid 4-methoxy-phenyl ester | 423 | Allyl-methyl-[4-(1,2,3,4-tetrahydro-quinolin-6-yloxy)-but-2-enyl]-amine | 4-Methoxyphenyl-chloroformate |
| 10.7 | 6-[4-(Allyl-methyl-amino)-but-2-enyloxy]-3,4-dihydro-2H-quinoline-1-carboxylic acid p-tolyl ester | 407 | Allyl-methyl-[4-(1,2,3,4-tetrahydro-quinolin-6-yloxy)-but-2-enyl]-amine | P-Tolyl-chloroformate |
| 10.8 | 6-[4-(Allyl-methyl-amino)-but-2-enyloxy]-3,4-dihydro-2H-quinoline-1-carboxylic acid 4-methoxycarbonyl-phenyl ester | 451 | Allyl-methyl-[4-(1,2,3,4-tetrahydro-quinolin-6-yloxy)-but-2-enyl]-amine | 4-Methoxy-carbonyl-phenyl chloroformate |
| 10.9 | 6-[4-(Allyl-methyl-amino)-but-2-enyloxy]-3,4-dihydro-2H-quinoline-1-carboxylic acid butyl ester | 373 | Allyl-methyl-[4-(1,2,3,4-tetrahydro-quinolin-6-yloxy)-but-2-enyl]-amine | Butyl-chloroformate |
| 10.10 | 6-[4-(Allyl-methyl-amino)-but-2-enyloxy]-3,4-dihydro-2H-quinoline-1-carboxylic acid 4-fluoro-phenyl ester | 411 | Allyl-methyl-[4-(1,2,3,4-tetrahydro-quinolin-6-yloxy)-but-2-enyl]-amine | 4-Fluorophenyl-chloroformate |
| 10.11 | 6-[6-(Allyl-methyl-amino)-hexyloxy]-3,4-dihydro-2H-quinoline-1-carboxylic acid 4-bromo-phenyl ester | 501 (1 Br) | Allyl-methyl-[6-(1,2,3,4-tetrahydro-quinolin-6-yloxy)-hexyl]-amine | 4-Bromophenyl-chloroformate |
| 10.12 | 6-[6-(Allyl-methyl-amino)-hexyloxy]-3,4-dihydro-2H-quinoline-1-carboxylic acid 4-fluoro-phenyl ester | 441 | Allyl-methyl-[6-(1,2,3,4-tetrahydro-quinolin-6-yloxy)-hexyl]-amine | 4-Fluorophenyl-chloroformate |
| 10.13 | 6-[6-(Allyl-methyl-amino)-hexyloxy]-3,4-dihydro-2H-quinoline-1-carboxylic acid p-tolyl ester | 437 | Allyl-methyl-[6-(1,2,3,4-tetrahydro-quinolin-6-yloxy)-hexyl]-amine | 4-Toloyl-chloroformate |
| 10.14 | 6-[6-(Allyl-methyl-amino)-hexyloxy]-3,4-dihydro-2H-quinoline-1-carboxylic acid hexyl ester | 431 | Allyl-methyl-[6-(1,2,3,4-tetrahydro-quinolin-6-yloxy)-hexyl]-amine | Hexyl-chloroformate |
| 10.15 | 6-[6-(Allyl-methyl-amino)-hexyloxy]-3,4-dihydro-2H-quinoline-1-carboxylic acid 4-methoxy-phenyl ester | 453 | Allyl-methyl-[6-(1,2,3,4-tetrahydro-quinolin-6-yloxy)-hexyl]-amine | 4-Methoxyphenyl-chloroformate |

Example 11

A solution of 0.133 mmol of the corresponding amine in 0.5 ml dry DMF was treated subsequently with 0.17 mmol (1.3 equivalents) of the corresponding acid, 0.266 mmol (2 equivalents) Huenig's base, 0.266 mmol (2 equivalents) N-(3-Dimethylaminopropyl)-N'-ethylcarbodiimide hydrochloride) (EDCI) as well as catalytic amount of Hydroxybenzotriazole (HOBt) (approximately 0.02 mmol). The solution was allowed to stand at room temperature over night. The resulting reaction mixture was treated with 0.15 ml formic acid and purified by preparative HPLC [RP-18, acetonitrile (0.1% HCOOH)/water (0.1% HCOOH), 10% to 95% acetonitrile]. After evaporation, the resulting compound was obtained as a mixture of amino hydrochloride and formate.

| No. | Compound | MS MH+ | Amine | Acid |
|---|---|---|---|---|
| 11.1 | {5-[4-(Allyl-methyl-amino)-butoxy]-2,3-dihydro-indol-1-yl}-(4-bromo-phenyl)-methanone | 443 (1 Br) | Allyl-[4-(2,3-dihydro-1H-indol-5-yloxy)-butyl]-methyl-amine | 4-Bromobenzoic acid |

-continued

| No. | Compound | MS MH+ | Amine | Acid |
|---|---|---|---|---|
| 11.2 | 3-{5-[4-(Allyl-methyl-amino)-butoxy]-2,3-dihydro-indole-1-carbonyl}-benzonitrile | 390 | Allyl-[4-(2,3-dihydro-1H-indol-5-yloxy)-butyl]-methyl-amine | 3-Cyanobenzoic acid |
| 11.3 | {5-[4-(Allyl-methyl-amino)-butoxy]-2,3-dihydro-indol-1-yl}-(4-fluoro-phenyl)-methanone | 383 | Allyl-[4-(2,3-dihydro-1H-indol-5-yloxy)-butyl]-methyl-amine | 4-Fluorobenzoic acid |
| 11.4 | {5-[4-(Allyl-methyl-amino)-butoxy]-2,3-dihydro-indol-1-yl}-(5-bromo-thiophen-2-yl)-methanone | 449 (1 Br) | Allyl-[4-(2,3-dihydro-1H-indol-5-yloxy)-butyl]-methyl-amine | 5-Bromothiophene-2-carboxylic acid |
| 11.5 | {5-[4-(Allyl-methyl-amino)-butoxy]-2,3-dihydro-indol-1-yl}-(4-chloro-phenyl)-methanone | 399 (1 Cl) | Allyl-[4-(2,3-dihydro-1H-indol-5-yloxy)-butyl]-methyl-amine | 4-Chloro-benzoic acid |
| 11.6 | {5-[4-(Allyl-methyl-amino)-butoxy]-2,3-dihydro-indol-1-yl}-phenyl-methanone | 365 | Allyl-[4-(2,3-dihydro-1H-indol-5-yloxy)-butyl]-methyl-amine | Benzoic acid |
| 11.7 | {5-[4-(Allyl-methyl-amino)-butoxy]-2,3-dihydro-indol-1-yl}-(4-trifluoromethyl-phenyl)-methanone | 433 | Allyl-[4-(2,3-dihydro-1H-indol-5-yloxy)-butyl]-methyl-amine | 4-Trifluoromethyl benzoic acid |
| 11.8 | {5-[5-(Allyl-methyl-amino)-pentyl]-2,3-dihydro-indol-1-yl}-(4-bromo-phenyl)-methanone | 441 (1 Br) | Allyl-[5-(2,3-dihydro-1H-indol-5-yl)-pentyl]-methyl-amine | 4-Bromobenzoic acid |
| 11.9 | 3-{5-[5-(Allyl-methyl-amino)-pentyl]-2,3-dihydro-indole-1-carbonyl}-benzonitrile | 388 | Allyl-[5-(2,3-dihydro-1H-indol-5-yl)-pentyl]-methyl-amine | 3-Cyanobenzoic acid |
| 11.10 | {5-[5-(Allyl-methyl-amino)-pentyl]-2,3-dihydro-indol-1-yl}-(4-fluoro-phenyl)-methanone | 381 | Allyl-[5-(2,3-dihydro-1H-indol-5-yl)-pentyl]-methyl-amine | 4-Fluorobenzoic acid |
| 11.11 | {5-[5-(Allyl-methyl-amino)-pentyl]-2,3-dihydro-indol-1-yl}-(5-bromo-thiophen-2-yl)-methanone | 447 (1 Br) | Allyl-[5-(2,3-dihydro-1H-indol-5-yl)-pentyl]-methyl-amine | 5-Bromothiophene-2-carboxylic acid |
| 11.12 | {5-[5-(Allyl-methyl-amino)-pentyl]-2,3-dihydro-indol-1-yl}-(4-chloro-phenyl)-methanone | 397 (1 Cl) | Allyl-[5-(2,3-dihydro-1H-indol-5-yl)-pentyl]-methyl-amine | 4-Chlorobenzoic acid |
| 11.13 | {5-[5-(Allyl-methyl-amino)-pentyl]-2,3-dihydro-indol-1-yl}-phenyl-methanone | 363 | Allyl-[5-(2,3-dihydro-1H-indol-5-yl)-pentyl]-methyl-amine | Benzoic acid |
| 11.14 | 3-{6-[4-(Allyl-methyl-amino)-but-2-enyloxy]-3,4-dihydro-2H-quinoline-1-carbonyl}-benzonitrile | 402 | Allyl-methyl-[4-(1,2,3,4-tetrahydro-quinolin-6-yloxy)-but-2-enyl]-amine | 3-Cyanobenzoic acid |
| 11.15 | {6-[4-(Allyl-methyl-amino)-but-2-enyloxy]-3,4-dihydro-2H-quinolin-1-yl}-(4-bromo-phenyl)-methanone | 455 (1 Br) | Allyl-methyl-[4-(1,2,3,4-tetrahydro-quinolin-6-yloxy)-but-2-enyl]-amine | 4-Bromobenzoic acid |
| 11.16 | 1-{6-[4-(Allyl-methyl-amino)-but-2-enyloxy]-3,4-dihydro-2H-quinolin-1-yl}-2-(2,4-difluoro-phenyl)-ethanone | 427 | Allyl-methyl-[4-(1,2,3,4-tetrahydro-quinolin-6-yloxy)-but-2-enyl]-amine | 2,4-Difluorophenyl acetic acid |
| 11.17 | 1-(4-{6-[4-(Allyl-methyl-amino)-but-2-enyloxy]-3,4-dihydro-2H-quinoline-1-carbonyl}-phenyl)-ethanone | 419 | Allyl-methyl-[4-(1,2,3,4-tetrahydro-quinolin-6-yloxy)-but-2-enyl]-amine | Acetophenone-4-Carboxylic acid |
| 11.18 | {6-[4-(Allyl-methyl-amino)-but-2-enyloxy]-3,4-dihydro-2H-quinolin-1-yl}-(5-bromo-thiophen-2-yl)-methanone | 461 (1 Br) | Allyl-methyl-[4-(1,2,3,4-tetrahydro-quinolin-6-yloxy)-but-2-enyl]-amine | 5-Bromothiophene-2-Carboxylic acid |
| 11.19 | {6-[4-(Allyl-methyl-amino)-but-2-enyloxy]-3,4-dihydro-2H-quinolin-1-yl}-(3-chloro-phenyl)-methanone | 411 (1 Cl) | Allyl-methyl-[4-(1,2,3,4-tetrahydro-quinolin-6-yloxy)-but-2-enyl]-amine | 3-Chlorobenzoic acid |

-continued

| No. | Compound | MS MH+ | Amine | Acid |
|---|---|---|---|---|
| 11.20 | 1-{6-[4-(Allyl-methyl-amino)-but-2-enyloxy]-3,4-dihydro-2H-quinolin-1-yl}-2-(4-fluoro-phenyl)-ethanone | 409 | Allyl-methyl-[4-(1,2,3,4-tetrahydro-quinolin-6-yloxy)-but-2-enyl]-amine | 4-Fluorophenyl acetic acid |
| 11.21 | {6-[4-(Allyl-methyl-amino)-but-2-enyloxy]-3,4-dihydro-2H-quinolin-1-yl}-(4-fluoro-phenyl)-methanone | 395 | Allyl-methyl-[4-(1,2,3,4-tetrahydro-quinolin-6-yloxy)-but-2-enyl]-amine | 4-Fluorobenzoic acid |
| 11.22 | {6-[4-(Allyl-methyl-amino)-but-2-enyloxy]-3,4-dihydro-2H-quinolin-1-yl}-(4-chloro-phenyl)-methanone | 411 (1 Cl) | Allyl-methyl-[4-(1,2,3,4-tetrahydro-quinolin-6-yloxy)-but-2-enyl]-amine | 4-Chlorobenzoic acid |
| 11.23 | {6-[4-(Allyl-methyl-amino)-but-2-enyloxy]-3,4-dihydro-2H-quinolin-1-yl}-(4-trifluoromethyl-phenyl)-methanone | 445 | Allyl-methyl-[4-(1,2,3,4-tetrahydro-quinolin-6-yloxy)-but-2-enyl]-amine | 4-(Trifluoromethyl) Benzoic acid |
| 11.24 | {6-[4-(Allyl-methyl-amino)-but-2-enyloxy]-3,4-dihydro-2H-quinolin-1-yl}-pyridin-3-yl-methanone | 378 | Allyl-methyl-[4-(1,2,3,4-tetrahydro-quinolin-6-yloxy)-but-2-enyl]-amine | Nicotinic acid |
| 11.25 | {6-[4-(Allyl-methyl-amino)-but-2-enyloxy]-3,4-dihydro-2H-quinolin-1-yl}-(4-fluoro-3-methyl-phenyl)-methanone | 409 | Allyl-methyl-[4-(1,2,3,4-tetrahydro-quinolin-6-yloxy)-but-2-enyl]-amine | 4-Fluoro-3-Methyl benzoic acid |
| 11.26 | 3-{6-[6-(Allyl-methyl-amino)-hexyloxy]-3,4-dihydro-2H-quinoline-1-carbonyl}-benzonitrile | 432 | Allyl-methyl-[6-(1,2,3,4-tetrahydro-quinolin-6-yloxy)-hexyl]-amine | 3-Cyanophenyl benoicacid |
| 11.27 | {6-[6-(Allyl-methyl-amino)-hexyloxy]-3,4-dihydro-2H-quinolin-1-yl}-(4-bromo-phenyl)-methanone | 485 (1 Br) | Allyl-methyl-[6-(1,2,3,4-tetrahydro-quinolin-6-yloxy)-hexyl]-amine | 4-Bromophenyl benzoicacid |
| 11.28 | {6-[6-(Allyl-methyl-amino)-hexyloxy]-3,4-dihydro-2H-quinolin-1-yl}-(5-bromo-thiophen-2-yl)-methanone | 491 (1 Br) | Allyl-methyl-[6-(1,2,3,4-tetrahydro-quinolin-6-yloxy)-hexyl]-amine | 2-Bromothiophene-5-carboxylicacid |
| 11.29 | {6-[6-(Allyl-methyl-amino)-hexyloxy]-3,4-dihydro-2H-quinolin-1-yl}-(4-fluoro-phenyl)-methanone | 425 | Allyl-methyl-[6-(1,2,3,4-tetrahydro-quinolin-6-yloxy)-hexyl]-amine | 4-Fluorophenyl benzoic acid |
| 11.30 | {6-[4-(Allyl-methyl-amino)-butoxy]-3,4-dihydro-2H-quinolin-1-yl}-(4-bromo-phenyl)-methanone | 457 (1 Br) | Allyl-methyl-[4-(1,2,3,4-tetrahydro-quinolin-6-yloxy)-butyl]-amine | 4-Bromobenzoic acid |
| 11.31 | 3-{6-[4-(Allyl-methyl-amino)-butoxy]-3,4-dihydro-2H-quinoline-1-carbonyl}-benzonitrile | 404 | Allyl-methyl-[4-(1,2,3,4-tetrahydro-quinolin-6-yloxy)-butyl]-amine | 3-Cyanobenzoic acid |
| 11.32 | {6-[4-(Allyl-methyl-amino)-butoxy]-3,4-dihydro-2H-quinolin-1-yl}-(4-fluoro-phenyl)-methanone | 397 | Allyl-methyl-[4-(1,2,3,4-tetrahydro-quinolin-6-yloxy)-butyl]-amine | 4-Fluorobenzoic acid |
| 11.33 | {6-[4-(Allyl-methyl-amino)-butoxy]-3,4-dihydro-2H-quinolin-1-yl}-(5-bromo-thiophen-2-yl)-methanone | 463 (1 Br) | Allyl-methyl-[4-(1,2,3,4-tetrahydro-quinolin-6-yloxy)-butyl]-amine | 5-Bromothiophene-2-carboxylicacid |
| 11.34 | {6-[4-(Allyl-methyl-amino)-butoxy]-3,4-dihydro-2H-quinolin-1-yl}-(4-chloro-phenyl)-methanone | 413 (1 Cl) | Allyl-methyl-[4-(1,2,3,4-tetrahydro-quinolin-6-yloxy)-butyl]-amine | 4-Chlorobenzoic acid |
| 11.35 | {6-[4-(Allyl-methyl-amino)-butoxy]-3,4-dihydro-2H-quinolin-1-yl}-phenyl-methanone | 379 | Allyl-methyl-[4-(1,2,3,4-tetrahydro-quinolin-6-yloxy)-butyl]-amine | Benzoic acid |
| 11.36 | {6-[4-(Allyl-methyl-amino)-butoxy]-3,4-dihydro-2H-quinolin-1-yl}-(4-trifluoromethyl-phenyl)-methanone | 447 | Allyl-methyl-[4-(1,2,3,4-tetrahydro-quinolin-6-yloxy)-butyl]-amine | 4-Trifluoromethyl benzoic acid |
| 11.37 | (4-Bromo-phenyl)-[6-(4-diethylamino-butoxy)-3,4- | 459 (1 Br) | Diethyl-[4-(1,2,3,4-tetrahydro- | 4-Bromobenzoic acid |

-continued

| No. | Compound | MS MH+ | Amine | Acid |
|---|---|---|---|---|
| | dihydro-2H-quinolin-1-yl]-methanone | | quinolin-6-yloxy)-butyl]-amine | |
| 11.38 | 3-[6-(4-Diethylamino-butoxy)-3,4-dihydro-2H-quinoline-1-carbonyl]-benzonitrile | 406 | Diethyl-[4-(1,2,3,4-tetrahydro-quinolin-6-yloxy)-butyl]-amine | 3-Cyanobenzoic acid |
| 11.39 | [6-(4-Diethylamino-butoxy)-3,4-dihydro-2H-quinolin-1-yl]-(4-fluoro-phenyl)-methanone | 399 | Diethyl-[4-(1,2,3,4-tetrahydro-quinolin-6-yloxy)-butyl]-amine | 4-Fluorobenzoic acid |
| 11.40 | (5-Bromo-thiophen-2-yl)-[6-(4-diethylamino-butoxy)-3,4-dihydro-2H-quinolin-1-yl]-methanone | 465 (1 Br) | Diethyl-[4-(1,2,3,4-tetrahydro-quinolin-6-yloxy)-butyl]-amine | 5-Bromothiophene-2-carboxylic acid |

Example 12

A solution of 0.133 mmol of the corresponding amine was treated with 0.17 mmol (1.3 equivalents) of the corresponding isothiocyanate in 0.35 ml dry dioxane. The solution was allowed to stand at room temperature over night, was treated with 0.15 ml formic acid and purified by preparative HPLC [RP-18, acetonitrile (0.1% HCOOH)/water (0.1% HCOOH), 10% to 95% acetonitrile]. After evaporation of the corresponding fraction, the compound was obtained as amino formate.

| No. | Compound | MS MH+ | Amine | Isothiocyanate |
|---|---|---|---|---|
| 12.1 | 5-[4-(Allyl-methyl-amino)-butoxy]-2,3-dihydro-indole-1-carbothioic acid (4-chloro-phenyl)-amide | 430 (1 Cl) | Allyl-[4-(2,3-dihydro-1H-indol-5-yloxy)-butyl]-methyl-amine | 4-Chlorophenyl-isothiocyanate |
| 12.2 | 5-[4-(Allyl-methyl-amino)-butoxy]-2,3-dihydro-indole-1-carbothioic acid cycloheptylamide | 416 | Allyl-[4-(2,3-dihydro-1H-indol-5-yloxy)-butyl]-methyl-amine | Cycloheptyl-isothiocyanate |
| 12.3 | 5-[4-(Allyl-methyl-amino)-butoxy]-2,3-dihydro-indole-1-carbothioic acid cyclohexylmethyl-amide | 416 | Allyl-[4-(2,3-dihydro-1H-indol-5-yloxy)-butyl]-methyl-amine | Cyclohexane-methyl-isothiocyanate |
| 12.4 | 5-[4-(Allyl-methyl-amino)-butoxy]-2,3-dihydro-indole-1-carbothioic acid 4-chloro-benzylamide | 444 (1 Cl) | Allyl-[4-(2,3-dihydro-1H-indol-5-yloxy)-butyl]-methyl-amine | 4-Chlorobenzyl-isothiocyanate |
| 12.5 | 5-[4-(Allyl-methyl-amino)-butoxy]-2,3-dihydro-indole-1-carbothioic acid (4-trifluoromethyl-phenyl)-amide | 464 | Allyl-[4-(2,3-dihydro-1H-indol-5-yloxy)-butyl]-methyl-amine | 4-Trifluoromethyl-phenyl-isothiocyanate |
| 12.6 | 5-[4-(Allyl-methyl-amino)-butoxy]-2,3-dihydro-indole-1-carbothioic acid 4-fluoro-benzylamide | 428 | Allyl-[4-(2,3-dihydro-1H-indol-5-yloxy)-butyl]-methyl-amine | 4-Fluorobenzyl-isothiocyanate |
| 12.7 | 5-[4-(Allyl-methyl-amino)-butoxy]-2,3-dihydro-indole-1-carbothioic acid benzylamide | 410 | Allyl-[4-(2,3-dihydro-1H-indol-5-yloxy)-butyl]-methyl-amine | Benzyl-isothiocyanate |
| 12.8 | 5-[4-(Allyl-methyl-amino)-butoxy]-2,3-dihydro-indole-1-carbothioic acid cyclohexylamide | 402 | Allyl-[4-(2,3-dihydro-1H-indol-5-yloxy)-butyl]-methyl-amine | Cyclohexyl-isothiocyanate |
| 12.9 | 5-[5-(Allyl-methyl-amino)-pentyl]-2,3-dihydro-indole-1-carbothioic acid (4-chloro-phenyl)-amide | 428 (1 Cl) | Allyl-[5-(2,3-dihydro-1H-indol-5-yl)-pentyl]-methyl-amine | 4-Chlorophenyl-isothiocyanate |
| 12.10 | 5-[5-(Allyl-methyl-amino)-pentyl]-2,3-dihydro-indole-1-carbothioic acid cycloheptylamide | 414 | Allyl-[5-(2,3-dihydro-1H-indol-5-yl)-pentyl]-methyl-amine | Cycloheptyl-isothiocyanate |
| 12.11 | 5-[5-(Allyl-methyl-amino)-pentyl]-2,3-dihydro-indole-1-carbothioic acid cyclohexylmethyl-amide | 414 | Allyl-[5-(2,3-dihydro-1H-indol-5-yl)-pentyl]-methyl-amine | Cyclohexanemethyl-isothiocyanate |

-continued

| No. | Compound | MS MH+ | Amine | Isothiocyanate |
|---|---|---|---|---|
| 12.12 | 5-[5-(Allyl-methyl-amino)-pentyl]-2,3-dihydro-indole-1-carbothioic acid 4-chloro-benzylamide | 442 (1 Cl) | Allyl-[5-(2,3-dihydro-1H-indol-5-yl)-pentyl]-methyl-amine | 4-Chlorobenzyl-isothiocyasnate |
| 12.13 | 5-[5-(Allyl-methyl-amino)-pentyl]-2,3-dihydro-indole-1-carbothioic acid (4-trifluoromethyl-phenyl)-amide | 462 | Allyl-[5-(2,3-dihydro-1H-indol-5-yl)-pentyl]-methyl-amine | 4-Trifluoromethyl-phenyl-isothiocyanate |
| 12.14 | 5-[5-(Allyl-methyl-amino)-pentyl]-2,3-dihydro-indole-1-carbothioic acid 4-fluoro-benzylamide | 426 | Allyl-[5-(2,3-dihydro-1H-indol-5-yl)-pentyl]-methyl-amine | 4-Fluorobenzyl-isothiocyanate |
| 12.15 | 5-[4-(Allyl-methyl-amino)-butoxy]-2,3-dihydro-indole-1-carbothioic acid (3-methyl-butyl)-amide | 390 | Allyl-[4-(2,3-dihydro-1H-indol-5-yloxy)-butyl]-methyl-amine | 1-Isothiocyanato-3-methyl-butane |
| 12.16 | 5-[4-(Allyl-methyl-amino)-butoxy]-2,3-dihydro-indole-1-carbothioic acid (furan-2-ylmethyl)-amide | 400 | Allyl-[4-(2,3-dihydro-1H-indol-5-yloxy)-butyl]-methyl-amine | 2-Furfuryl-isothiocyanate |
| 12.17 | 5-[4-(Allyl-methyl-amino)-butoxy]-2,3-dihydro-indole-1-carbothioic acid ethylamide | 348 | Allyl-[4-(2,3-dihydro-1H-indol-5-yloxy)-butyl]-methyl-amine | Isothiocyanato-ethane |
| 12.18 | 5-[4-(Allyl-methyl-amino)-butoxy]-2,3-dihydro-indole-1-carbothioic acid butylamide | 376 | Allyl-[4-(2,3-dihydro-1H-indol-5-yloxy)-butyl]-methyl-amine | Isothiocyanato-butane |
| 12.19 | 5-[4-(Allyl-methyl-amino)-butoxy]-2,3-dihydro-indole-1-carbothioic acid (2-methyl-butyl)-amide | 390 | Allyl-[4-(2,3-dihydro-1H-indol-5-yloxy)-butyl]-methyl-amine | 1-Isothiocyanato-2-methyl-butane |
| 12.20 | 5-[4-(Allyl-methyl-amino)-butoxy]-2,3-dihydro-indole-1-carbothioic acid (2-methoxy-ethyl)-amide | 378 | Allyl-[4-(2,3-dihydro-1H-indol-5-yloxy)-butyl]-methyl-amine | 1-Isothiocyanato-2-methoxy-ethane |
| 12.21 | 5-[4-(Allyl-methyl-amino)-butoxy]-2,3-dihydro-indole-1-carbothioic acid (4-butyl-phenyl)-amide | 452 | Allyl-[4-(2,3-dihydro-1H-indol-5-yloxy)-butyl]-methyl-amine | 1-Butyl-4-isothiocyanato-benzene |
| 12.22 | 5-[4-(Allyl-methyl-amino)-butoxy]-2,3-dihydro-indole-1-carbothioic acid (tetrahydro-furan-2-ylmethyl)-amide | 404 | Allyl-[4-(2,3-dihydro-1H-indol-5-yloxy)-butyl]-methyl-amine | 2-Tetrahydro-furfuryl-isothiocyanate |
| 12.23 | 6-[4-(Allyl-methyl-amino)-butoxy]-3,4-dihydro-2H-quinoline-1-carbothioic acid (4-chloro-phenyl)-amide | 444 (1 Cl) | Allyl-methyl-[4-(1,2,3,4-tetrahydro-quinolin-6-yloxy)-butyl]-amine | 4-Chlorophenyl-isothiocyanat |
| 12.24 | 6-[4-(Allyl-methyl-amino)-butoxy]-3,4-dihydro-2H-quinoline-1-carbothioic acid cycloheptylamide | 430 | Allyl-methyl-[4-(1,2,3,4-tetrahydro-quinolin-6-yloxy)-butyl]-amine | Cycloheptyl-isothiocyanat |
| 12.25 | 6-[4-(Allyl-methyl-amino)-butoxy]-3,4-dihydro-2H-quinoline-1-carbothioic acid cyclohexylmethyl-amide | 430 | Allyl-methyl-[4-(1,2,3,4-tetrahydro-quinolin-6-yloxy)-butyl]-amine | Cyclohexane-methyl-isothiocyanate |
| 12.26 | 6-[4-(Allyl-methyl-amino)-butoxy]-3,4-dihydro-2H-quinoline-1-carbothioic acid 4-chloro-benzylamide | 458 (1 Cl) | Allyl-methyl-[4-(1,2,3,4-tetrahydro-quinolin-6-yloxy)-butyl]-amine | 4-Chlorobenzyl-isothiocyasnate |
| 12.27 | 6-[4-(Allyl-methyl-amino)-butoxy]-3,4-dihydro-2H-quinoline-1-carbothioic acid (4-trifluoromethyl-phenyl)-amide | 478 | Allyl-methyl-[4-(1,2,3,4-tetrahydro-quinolin-6-yloxy)-butyl]-amine | 4-Trifluoromethyl-phenyl-isothiocyanat |
| 12.28 | 6-[4-(Allyl-methyl-amino)-butoxy]-3,4-dihydro-2H-quinoline-1-carbothioic acid 4-fluoro-benzylamide | 442 | Allyl-methyl-[4-(1,2,3,4-tetrahydro-quinolin-6-yloxy)-butyl]-amine | 4-Fluorobenzyl-isothiocyanate |
| 12.29 | 6-[4-(Allyl-methyl-amino)-butoxy]-3,4-dihydro-2H- | 424 | Allyl-methyl-[4-(1,2,3,4-tetrahydro- | Benzyl-isothiocyanate |

| No. | Compound | MS MH+ | Amine | Isothiocyanate |
|---|---|---|---|---|
|  | quinoline-1-carbothioic acid benzylamide |  | quinolin-6-yloxy)-butyl]-amine |  |
| 12.30 | 6-[4-(Allyl-methyl-amino)-butoxy]-3,4-dihydro-2H-quinoline-1-carbothioic acid cyclohexylamide | 416 | Allyl-methyl-[4-(1,2,3,4-tetrahydro-quinolin-6-yloxy)-butyl]-amine | Cyclohexyl-isothiocyanate |
| 12.31 | 6-[6-(Allyl-methyl-amino)-hexyloxy]-3,4-dihydro-2H-quinoline-1-carbothioic acid (4-chloro-phenyl)-amide | 472 (1 Cl) | Allyl-methyl-[6-(1,2,3,4-tetrahydro-quinolin-6-yloxy)-hexyl]-amine | p-Chlorophenyl-isothiocyanate |
| 12.32 | 6-[6-(Allyl-methyl-amino)-hexyloxy]-3,4-dihydro-2H-quinoline-1-carbothioic acid cycloheptylamide | 458 | Allyl-methyl-[6-(1,2,3,4-tetrahydro-quinolin-6-yloxy)-hexyl]-amine | Cycloheptyl-isothiocyanate |

Example 13

A solution of 0.14 mmol of the corresponding amine in 0.5 ml dry dioxane was treated with a solution of 0.14 mmol of the corresponding chlorothionoformate in 0.35 ml dry dioxane. The solution was allowed to stand at room temperature over night, treated with 0.15 ml formic acid and purified by preparative HPLC [RP-18, acetonitrile (0.1% HCOOH)/water (0.1% HCOOH), 10% to 95% acetonitrile]. After evaporation of the corresponding fraction, the compound was obtained as a mixture of amino hydrochloride and formate.

Example 14

A solution of 0.135 mmol of the corresponding amine in 0.75 ml dry dioxane was treated with 5 equivalents of triethylamine followed by a solution of 0.175 mmol (1.3 equivalente) of the corresponding sulfamoylchloride in 0.25 ml dry dioxane. The suspension was allowed to stand at room temperature over night, treated with 0.15 ml formic acid and purified by preparative HPLC [RP-18, acetonitrile (0.1% HCOOH)/water (0.1% HCOOH), 10% to 95% acetonitrile]. After evaporation of the corresponding fraction, the resulting compound was obtained as a mixture of amino hydrochloride and formate.

| No. | Compound | MS MH+ | Amine | Chloro-thionoformate |
|---|---|---|---|---|
| 13.1 | 5-[5-(Allyl-methyl-amino)-pentyl]-2,3-dihydro-indole-1-carbothioic acid O-(4-fluoro-phenyl) ester | 413 | Allyl-[5-(2,3-dihydro-1H-indol-5-yl)-pentyl]-methyl-amine | 4-Fluorophenyl-chloro-thionoformate |
| 13.2 | 5-[5-(Allyl-methyl-amino)-pentyl]-2,3-dihydro-indole-1-carbothioic acid O-phenyl ester | 395 | Allyl-[5-(2,3-dihydro-1H-indol-5-yl)-pentyl]-methyl-amine | Phenyl-chloro-thionoformate |
| 13.3 | 5-[5-(Allyl-methyl-amino)-pentyl]-2,3-dihydro-indole-1-carbothioic acid O-p-tolyl ester | 409 | Allyl-[5-(2,3-dihydro-1H-indol-5-yl)-pentyl]-methyl-amine | p-Toloyl-chloro-thionoformate |
| 13.4 | 6-(4-Diethylamino-butoxy)-3,4-dihydro-2H-quinoline-1-carbothioic acid O-(4-fluoro-phenyl) ester | 431 | Diethyl-[4-(1,2,3,4-tetrahydro-quinolin-6-yloxy)-butyl]-amine | 4-Fluoro-phenyl-chloro-thionoformate |
| 13.5 | 6-(4-Diethylamino-butoxy)-3,4-dihydro-2H-quinoline-1-carbothioic acid O-(4-chloro-phenyl) ester | 447 (1 Cl) | Diethyl-[4-(1,2,3,4-tetrahydro-quinolin-6-yloxy)-butyl]-amine | 4-Chloro-phenyl-chloro-thionoformate |
| 13.6 | 6-[4-(Allyl-methyl-amino)-butoxy]-3,4-dihydro-2H-quinoline-1-carbothioic acid O-(4-fluoro-phenyl) ester | 429 | Allyl-methyl-[4-(1,2,3,4-tetrahydro-quinolin-6-yloxy)-butyl]-amine | 4-Fluoro-phenyl-chloro-thionoformate |
| 13.7 | 6-[4-(Allyl-methyl-amino)-butoxy]-3,4-dihydro-2H-quinoline-1-carbothioic acid O-(4-chloro-phenyl) ester | 445 (1 Cl) | Allyl-methyl-[4-(1,2,3,4-tetrahydro-quinolin-6-yloxy)-butyl]-amine | 4-Chloro-phenyl-chloro-thionoformate |
| 13.8 | 6-[4-(Allyl-methyl-amino)-butoxy]-3,4-dihydro-2H-quinoline-1-carbothioic acid O-phenyl ester | 411 | Allyl-methyl-[4-(1,2,3,4-tetrahydro-quinolin-6-yloxy)-butyl]-amine | Phenyl-chloro-thionoformate |

| No. | Compound | MS MH+ | Amine | Sulfamoylchloride |
|---|---|---|---|---|
| 14.1 | 5-[4-(Allyl-methyl-amino)-butoxy]-2,3-dihydro-indole-1-sulfonic acid (4-chloro-phenyl)-amide | 450 (1 Cl) | Allyl-[4-(2,3-dihydro-1H-indol-5-yloxy)-butyl]-methyl-amine | 4-Chlorophenyl-sulfamoylchloride |
| 14.2 | 5-[4-(Allyl-methyl-amino)-butoxy]-2,3-dihydro-indole-1-sulfonic acid p-tolylamide | 430 | Allyl-[4-(2,3-dihydro-1H-indol-5-yloxy)-butyl]-methyl-amine | 4-Methylphenyl-sulfamoylchloride |
| 14.3 | 5-[4-(Allyl-methyl-amino)-butoxy]-2,3-dihydro-indole-1-sulfonic acid (4-cyano-phenyl)-amide | 441 | Allyl-[4-(2,3-dihydro-1H-indol-5-yloxy)-butyl]-methyl-amine | 4-Cyanophenyl-sulfamoylchloride |
| 14.4 | 5-[4-(Allyl-methyl-amino)-butoxy]-2,3-dihydro-indole-1-sulfonic acid (4-methoxy-phenyl)-amide | 446 | Allyl-[4-(2,3-dihydro-1H-indol-5-yloxy)-butyl]-methyl-amine | 4-Methoxyphenyl-sulfamoylchloride |
| 14.5 | 5-[4-(Allyl-methyl-amino)-butoxy]-2,3-dihydro-indole-1-sulfonic acid (3,4-difluoro-phenyl)-amide | 452 | Allyl-[4-(2,3-dihydro-1H-indol-5-yloxy)-butyl]-methyl-amine | 3,4-Difluorophenyl-sulfamoylchloride |
| 14.6 | 5-[4-(Allyl-methyl-amino)-butoxy]-2,3-dihydro-indole-1-sulfonic acid (3-fluoro-phenyl)-amide | 434 | Allyl-[4-(2,3-dihydro-1H-indol-5-yloxy)-butyl]-methyl-amine | 3-Fluorophenyl-sulfamoylchloride |
| 14.7 | 5-[4-(Allyl-methyl-amino)-butoxy]-2,3-dihydro-indole-1-sulfonic acid (2,4-difluoro-phenyl)-amide | 452 | Allyl-[4-(2,3-dihydro-1H-indol-5-yloxy)-butyl]-methyl-amine | 2,4-Difluorophenyl-sulfamoylchloride |
| 14.8 | 5-[4-(Allyl-methyl-amino)-butoxy]-2,3-dihydro-indole-1-sulfonic acid (2,5-difluoro-phenyl)-amide | 452 | Allyl-[4-(2,3-dihydro-1H-indol-5-yloxy)-butyl]-methyl-amine | 2,5-Difluorophenyl-sulfamoylchloride |
| 14.9 | 5-[4-(Allyl-methyl-amino)-butoxy]-2,3-dihydro-indole-1-sulfonic acid (4-bromo-phenyl)-amide | 494 (1 Br) | Allyl-[4-(2,3-dihydro-1H-indol-5-yloxy)-butyl]-methyl-amine | 4-Bromophenyl-sulfamoylchloride |
| 14.10 | 5-[4-(Allyl-methyl-amino)-butoxy]-2,3-dihydro-indole-1-sulfonic acid phenylamide | 416 | Allyl-[4-(2,3-dihydro-1H-indol-5-yloxy)-butyl]-methyl-amine | Phenyl-sulfamoylchloride |
| 14.11 | 5-[5-(Allyl-methyl-amino)-pentyl]-2,3-dihydro-indole-1-sulfonic acid phenylamide | 414 | Allyl-[5-(2,3-dihydro-1H-indol-5-yl)-pentyl]-methyl-amine | Phenyl-sulfamoylchloride |
| 14.12 | 5-[5-(Allyl-methyl-amino)-pentyl]-2,3-dihydro-indole-1-sulfonic acid (4-chloro-phenyl)-amide | 448 (1 Cl) | Allyl-[5-(2,3-dihydro-1H-indol-5-yl)-pentyl]-methyl-amine | 4-Chlorophenyl-sulfamoylchloride |
| 14.13 | 5-[5-(Allyl-methyl-amino)-pentyl]-2,3-dihydro-indole-1-sulfonic acid (2,4-difluoro-phenyl)-amide | 450 | Allyl-[5-(2,3-dihydro-1H-indol-5-yl)-pentyl]-methyl-amine | 2,4-Difluorophenyl-sulfamoylchloride |
| 14.14 | 5-[5-(Allyl-methyl-amino)-pentyl]-2,3-dihydro-indole-1-sulfonic acid (4-fluoro-phenyl)-amide | 432 | Allyl-[5-(2,3-dihydro-1H-indol-5-yl)-pentyl]-methyl-amine | 4-Fluorophenyl-sulfonamylchloride |
| 14.15 | 6-[4-(Allyl-methyl-amino)-but-2-enyloxy]-3,4-dihydro-2H-quinoline-1-sulfonic acid (4-chloro-phenyl)-amide | 462 (1 Cl) | Allyl-methyl-[4-(1,2,3,4-tetrahydro-quinolin-6-yloxy)-but-2-enyl]-amine | 4-Chlorophenyl-sulfamoylchloride |
| 14.16 | 6-[4-(Allyl-methyl-amino)-but-2-enyloxy]-3,4-dihydro-2H-quinoline-1-sulfonic acid (4-fluoro-phenyl)-amide | 446 | Allyl-methyl-[4-(1,2,3,4-tetrahydro-quinolin-6-yloxy)-but-2-enyl]-amine | 4-Fluorophenyl-sulfamoylchloride |
| 14.17 | 6-[4-(Allyl-methyl-amino)-but-2-enyloxy]-3,4-dihydro-2H-quinoline-1-sulfonic acid (4-bromo-phenyl)-amide | 506 (1 Br) | Allyl-methyl-[4-(1,2,3,4-tetrahydro-quinolin-6-yloxy)-but-2-enyl]-amine | 4-Bromophenyl-sulfamoylchloride |
| 14.18 | 6-[4-(Allyl-methyl-amino)-but-2-enyloxy]-3,4-dihydro-2H-quinoline-1-sulfonic acid (p-tolyl)-amide | 442 | Allyl-methyl-[4-(1,2,3,4-tetrahydro-quinolin-6-yloxy)-but-2-enyl]-amine | p-tolyl-sulfamoylchloride |

-continued

| No. | Compound | MS MH+ | Amine | Sulfamoylchloride |
|---|---|---|---|---|
| 14.19 | 6-[4-(Allyl-methyl-amino)-but-2-enyloxy]-3,4-dihydro-2H-quinoline-1-sulfonic acid (3,4-difluoro-phenyl)-amide | 464 | Allyl-methyl-[4-(1,2,3,4-tetrahydro-quinolin-6-yloxy)-enyl-2-enyl]-amine | 3,4-Difluorophenyl-sulfamoylchloride |
| 14.20 | 6-[4-(Allyl-methyl-amino)-but-2-enyloxy]-3,4-dihydro-2H-quinoline-1-sulfonic acid (4-trifluoromethyl-phenyl)-amide | 496 | Allyl-methyl-[4-(1,2,3,4-tetrahydro-quinolin-6-yloxy)-enyl-2-enyl]-amine | 4-Trifluoromethyl-phenyl-sulfamoylchloride |
| 14.21 | 6-[4-(Allyl-methyl-amino)-but-2-enyloxy]-3,4-dihydro-2H-quinoline-1-sulfonic acid (3-fluoro-phenyl)-amide | 446 | Allyl-methyl-[4-(1,2,3,4-tetrahydro-quinolin-6-yloxy)-but-2-enyl]-amine | 3-Fluorophenyl-sulfamoylchloride |
| 14.22 | 6-[4-(Allyl-methyl-amino)-but-2-enyloxy]-3,4-dihydro-2H-quinoline-1-sulfonic acid (4-cyano-phenyl)-amide | 453 | Allyl-methyl-[4-(1,2,3,4-tetrahydro-quinolin-6-yloxy)-but-2-enyl]-amine | 4-Cyanophenyl-sulfamoylchloride |
| 14.23 | 6-[4-(Allyl-methyl-amino)-but-2-enyloxy]-3,4-dihydro-2H-quinoline-1-sulfonic acid (2,4-difluoro-phenyl)-amide | 464 | Allyl-methyl-[4-(1,2,3,4-tetrahydro-quinolin-6-yloxy)-but-2-enyl]-amine | 2,4-Difluorophenyl-sulfamoylchloride |
| 14.24 | 6-[4-(Allyl-methyl-amino)-but-2-enyloxy]-3,4-dihydro-2H-quinoline-1-sulfonic acid (4-methoxy-phenyl)-amide | 458 | Allyl-methyl-[4-(1,2,3,4-tetrahydro-quinolin-6-yloxy)-but-2-enyl]-amine | 4-Methoxyphenyl-sulfamoylchloride |
| 14.25 | 6-[4-(Allyl-methyl-amino)-but-2-enyloxy]-3,4-dihydro-2H-quinoline-1-sulfonic acid (2,5-difluoro-phenyl)-amide | 464 | Allyl-methyl-[4-(1,2,3,4-tetrahydro-quinolin-6-yloxy)-but-2-enyl]-amine | 2,5-Difluorophenyl-sulfamoylchloride |
| 14.26 | 6-[4-(Allyl-methyl-amino)-but-2-enyloxy]-3,4-dihydro-2H-quinoline-1-sulfonic acid (phenyl)-amide | 428 | Allyl-methyl-[4-(1,2,3,4-tetrahydro-quinolin-6-yloxy)-but-2-enyl]-amine | Phenyl-sulfamoylchloride |
| 14.27 | 6-[5-(Allyl-methyl-amino)-pentyloxy]-3,4-dihydro-2H-quinoline-1-sulfonic acid (4-chloro-phenyl)-amide | 478 (1 Cl) | Allyl-methyl-[5-(1,2,3,4-tetrahydro-quinolin-6-yloxy)-pentyl]-amine | 4-Chlorophenyl-sulfamoylchloride |
| 14.28 | 6-[5-(Allyl-methyl-amino)-pentyloxy]-3,4-dihydro-2H-quinoline-1-sulfonic acid (4-bromo-phenyl)-amide | 522 (1 Br) | Allyl-methyl-[5-(1,2,3,4-tetrahydro-quinolin-6-yloxy)-pentyl]-amine | 4-Bromophenyl-sulfamoylchloride |
| 14.29 | 6-[5-(Allyl-methyl-amino)-pentyloxy]-3,4-dihydro-2H-quinoline-1-sulfonic acid p-tolylamide acid | 458 | Allyl-methyl-[5-(1,2,3,4-tetrahydro-quinolin-6-yloxy)-pentyl]-amine | 4-Methylphenyl-sulfamoylchloride |
| 14.30 | 6-[5-(Allyl-methyl-amino)-pentyloxy]-3,4-dihydro-2H-quinoline-1-sulfonic acid (4-trifluoromethyl-phenyl)-amide | 512 | Allyl-methyl-[5-(1,2,3,4-tetrahydro-quinolin-6-yloxy)-pentyl]-amine | 4-Trifluoromethyl-phenyl-sulfamoylchloride |
| 14.31 | 6-[5-(Allyl-methyl-amino)-pentyloxy]-3,4-dihydro-2H-quinoline-1-sulfonic acid (4-cyano-phenyl)-amide | 469 | Allyl-methyl-[5-(1,2,3,4-tetrahydro-quinolin-6-yloxy)-pentyl]-amine | 4-Cyanophenyl-sulfamoylchloride |
| 14.32 | 6-[5-(Allyl-methyl-amino)-pentyloxy]-3,4-dihydro-2H-quinoline-1-sulfonic acid (4-methoxy-phenyl)-amide | 474 | Allyl-methyl-[5-(1,2,3,4-tetrahydro-quinolin-6-yloxy)-pentyl]-amine | 4-Methoxyphenyl-sulfamoylchloride |
| 14.33 | 6-[5-(Allyl-methyl-amino)-pentyloxy]-3,4-dihydro-2H-quinoline-1-sulfonic acid (4-fluoro-phenyl)-amide | 462 | Allyl-methyl-[5-(1,2,3,4-tetrahydro-quinolin-6-yloxy)-pentyl]-amine | 4-Fluorophenyl-sulfamoylchloride |
| 14.34 | 6-[5-(Allyl-methyl-amino)-pentyloxy]-3,4-dihydro-2H-quinoline-1-sulfonic acid (3,4-difluoro-phenyl)-amide | 480 | Allyl-methyl-[5-(l,2,3,4-tetrahydro-quinolin-6-yloxy)-pentyl]-amine | 3,4-Difluorophenyl-sulfamoylchloride |
| 14.35 | 6-[5-(Allyl-methyl-amino)-pentyloxy]-3,4-dihydro-2H- | 462 | Allyl-methyl-[5-(1,2,3,4-tetrahydro- | 3-Fluorophenyl-sulfamoylchloride |

-continued

| No. | Compound | MS MH+ | Amine | Sulfamoylchloride |
|---|---|---|---|---|
| | quinoline-1-sulfonic acid (3-fluoro-phenyl)-amide | | quinolin-6-yloxy)-pentyl]-amine | |
| 14.36 | 6-[5-(Allyl-methyl-amino)-pentyloxy]-3,4-dihydro-2H-quinoline-1-sulfonic acid (2,4-difluoro-phenyl)-amide | 480 | Allyl-methyl-[5-(1,2,3,4-tetrahydro-quinolin-6-yloxy)-pentyl]-amine | 2,4-Difluorophenyl-sulfamoylchloride |
| 14.37 | 6-[5-(Allyl-methyl-amino)-pentyloxy]-3,4-dihydro-2H-quinoline-1-sulfonic acid (2,5-difluoro-phenyl)-amide | 480 | Allyl-methyl-[5-(1,2,3,4-tetrahydro-quinolin-6-yloxy)-pentyl]-amine | 2,5-Difluorophenyl-sulfamoylchloride |
| 14.38 | 6-[6-(Allyl-methyl-amino)-hexyloxy]-3,4-dihydro-2H-quinoline-1-sulfonic acid (4-cyano-phenyl)-amide | 483 | Allyl-methyl-[6-(1,2,3,4-tetrahydro-quinolin-6-yloxy)-hexyl]-amine | 4-Cyanophenyl-sulfamoylchloride |
| 14.39 | 6-[6-(Allyl-methyl-amino)-hexyloxy]-3,4-dihydro-2H-quinoline-1-sulfonic acid (4-methoxy-phenyl)-amide | 488 | Allyl-methyl-[6-(1,2,3,4-tetrahydro-quinolin-6-yloxy)-hexyl]-amine | 4-Methoxyphenyl-sulfamoylchloride |
| 14.40 | 6-[6-(Allyl-methyl-amino)-hexyloxy]-3,4-dihydro-2H-quinoline-1-sulfonic acid (4-chloro-phenyl)-amide | 492 (1 Cl) | Allyl-methyl-[6-(1,2,3,4-tetrahydro-quinolin-6-yloxy)-hexyl]-amine | 4-Chlorophenyl-sulfamoylchloride |
| 14.41 | 6-[6-(Allyl-methyl-amino)-hexyloxy]-3,4-dihydro-2H-quinoline-1-sulfonic acid (2,5-difluoro-phenyl)-amide | 494 | Allyl-methyl-[6-(1,2,3,4-tetrahydro-quinolin-6-yloxy)-hexyl]-amine | 2,5-Difluorophenyl-sulfamoylchloride |
| 14.42 | 6-[6-(Allyl-methyl-amino)-hexyloxy]-3,4-dihydro-2H-quinoline-1-sulfonic acid (4-bromo-phenyl)-amide | 536 (1 Br) | Allyl-methyl-[6-(1,2,3,4-tetrahydro-quinolin-6-yloxy)-hexyl]-amine | 4-Bromophenyl-sulfamoylchloride |
| 14.43 | 6-[6-(Allyl-methyl-amino)-hexyloxy]-3,4-dihydro-2H-quinoline-1-sulfonic acid (2,4-difluoro-phenyl)-amide | 494 | Allyl-methyl-[6-(1,2,3,4-tetrahydro-quinolin-6-yloxy)-hexyl]-amine | 2,4-Difluorophenyl-sulfamoylchloride |
| 14.44 | 6-[6-(Allyl-methyl-amino)-hexyloxy]-3,4-dihydro-2H-quinoline-1-sulfonic acid p-tolylamide | 472 | Allyl-methyl-[6-(1,2,3,4-tetrahydro-quinolin-6-yloxy)-hexyl]-amine | p-Tolyl-sulfamoylchloride |
| 14.45 | 6-[6-(Allyl-methyl-amino)-hexyloxy]-3,4-dihydro-2H-quinoline-1-sulfonic acid butylamide | 438 | Allyl-methyl-[6-(1,2,3,4-tetrahydro-quinolin-6-yloxy)-hexyl]-amine | Butyl-sulfamoylchloride |
| 14.46 | 6-[6-(Allyl-methyl-amino)-hexyloxy]-3,4-dihydro-2H-quinoline-1-sulfonic acid (3-fluoro-phenyl)-amide | 476 | Allyl-methyl-[6-(1,2,3,4-tetrahydro-quinolin-6-yloxy)-hexyl]-amine | 3-Fluorophenyl-sulfamoylchloride |
| 14.47 | 6-[6-(Allyl-methyl-amino)-hexyloxy]-3,4-dihydro-2H-quinoline-1-sulfonic acid phenylamide | 458 | Allyl-methyl-[6-(1,2,3,4-tetrahydro-quinolin-6-yloxy)-hexyl]-amine | Phenyl-sulfamoylchloride |
| 14.48 | 6-[4-(Allyl-methyl-amino)-butoxy]-3,4-dihydro-2H-quinoline-1-sulfonic acid phenylamide | 430 | Allyl-methyl-[4-(1,2,3,4-tetrahydro-quinolin-6-yloxy)-butyl]-amine | Phenyl-sulfamoylchloride |
| 14.49 | 6-[4-(Allyl-methyl-amino)-butoxy]-3,4-dihydro-2H-quinoline-1-sulfonic acid (4-chloro-phenyl)-amide | 464 (1 Cl) | Allyl-methyl-[4-(1,2,3,4-tetrahydro-quinolin-6-yloxy)-butyl]-amine | 4-Chlorophenyl-sulfamoylchloride |
| 14.50 | 6-[4-(Allyl-methyl-amino)-butoxy]-3,4-dihydro-2H-quinoline-1-sulfonic acid (2,4-difluoro-phenyl)-amide | 466 | Allyl-methyl-[4-(1,2,3,4-tetrahydro-quinolin-6-yloxy)-butyl]-amine | 2,4-Difluorophenyl-sulfamoylchloride |
| 14.51 | 6-[4-(Allyl-methyl-amino)-butoxy]-3,4-dihydro-2H-quinoline-1-sulfonic acid (4-fluoro-phenyl)-amide | 448 | Allyl-methyl-[4-(1,2,3,4-tetrahydro-quinolin-6-yloxy)-butyl]-amine | 4-Fluorophenyl-sulfonamylchloride |

Example 15

Sulfamoyl chlorides were prepared according to the following procedure. 3 equivalents of the corresponding amine were dissolved in $CH_2Cl_2$ (1 ml/mmol) and placed in an ice bath. A solution of chlorosulfonic acid (1 eq.) in $CH_2Cl_2$ (0.5 ml/mmol) was added slowly (30 min). The reaction mixture was stirred at 0° C. for a further 30 min. Afterwards, the ice bath was removed and the stirring was continued for 1 h at room temperature. The precipitate was collected by filtration and dried under high vacuum. This salt was suspended in toluene (1 ml/mmol amine) and $PCl_5$ (1 eq) was added. The mixture was stirred at 75° C. for 2 h, cooled to room temperature and filtered. The solid residue was washed with toluene. The filtrate was evaporated and dried under high vacuum. The resulting crude sulfamoyl chloride was used in the next step without further purification. The following sulfamoyl chlorides were prepared from the corresponding amines: Phenylsulfamoyl chloride, 2,4-Difluoro-phenylsulfamoyl chloride, 2,5-Difluoro-phenylsulfamoyl chloride, 3,4-Difluoro-phenylsulfamoyl chloride, 3-Fluoro phenyl-sulfamoyl chloride, 4-Fluoro-phenylsulfamoyl chloride, 4-Chloro-phenylsulfamoyl chloride, 4-Bromo-phenylsulfamoyl chloride, 4-Methyl-phenylsulfamoyl chloride, 4-trifluoromethyl-phenylsulfamoyl chloride, 4-Cyano-phenylsulfamoyl chloride, 4-Methoxy-phenylsulfamoyl chloride, Butylsulfamoyl chloride.

Example 16

16.1

To 33.3 g (0.3 mol) 3-fluoroaniline in 160 ml $CH_2Cl_2$ were added 450 ml of a 0.7 M aqueous $NaHCO_3$-solution. The resulting mixture was treated dropwise with 34.6 ml (0.41 mol) methylchloroformate within a period of 20 min. After stirring overnight the layers were separated and the organic layer was washed with saturated aqueous NaCl and dried with $MgSO_4$. After evaporation of ca. 60% of the solvent, 600 ml of hexane were added, whereby (3-Fluoro-phenyl)-carbamic acid methyl ester precipitated as a colorless solid that was filtered off and dried i.v. (41 g (81%)).

The solid was dissolved in 600 ml acetonitrile and treated subsequently with 50 g (0.28 mmol) N-bromosuccinimide and 2.13 ml (0.024 mol) trifluormethane sulfonic acid. After stirring at room temperature during 12 hours, ca. 50% of the solvent were evaporated, the resulting mixture diluted with 1000 ml EtOAc, and washed subsequently with saturated aqueous $NaHCO_3$ and saturated aqueous NaCl. Drying of the combined organic layers with $MgSO_4$, evaporation of the solvent, and column chromatography of the residue on silica gel with hexane/EtOAc 8:1 and then 2:1 gave 39 g (64%) (4-Bromo-3-fluoro-phenyl)-carbamic acid methyl ester as a colorless solid. The solid was dissolved in 390 ml acetonitrile, treated subsequently with 39 g (0.172 mol) N-iodosuccinimide and 1.4 ml (0.016 mol) trifluormethane-sulfonic acid at 0° C. and left to stir at room temperature during 10 hours. Cooling the reaction mixture to 0° C. led to precipitation of (4-Bromo-5-fluoro-2-iodo-phenyl)-carbamic acid methyl ester as colorless crystals that were filtered off and dried (26.7 g, 44%). Dilution of the filtrate with 600 ml hexane followed by subsequent washing with saturated aqueous $NaHCO_3$ and 0.5M aqueous $NaS_2O_3$, drying of the organic layer with $MgSO_4$, evaporation of the solvent, and recrystallization of the residue in acetonitrile gave an additional 6.3 g (12%) of (4-Bromo-5-fluoro-2-iodo-phenyl)-carbamic acid methyl ester (total: 33 g, 56%), MS: 373 (M, 1Br).

16.2

A mixture of 70 mg (0.1 mmol) $Pd(PPh_3)_2Cl_2$ and 27 mg (0.142 mmol) CuI in triethylamine was refluxed under argon during 20 min, cooled to 0° C., treated with 7 g (0.019 mmol) (4-Bromo-5-fluoro-2-iodo-phenyl)-carbamic acid methyl ester, stirred 10 min at room temperature, treated with 2.95 (0.021 mmol) ethinyltrimethylsilane, and stirred 1 h at room temperature. 2M aqueous HCl and ice were added and the mixture extracted three times with EtOAc. The combined organic layers were washed subsequently with $H_2O$ and saturated aqueous NaCl, dried with $MgSO_4$ and the solvent was evaporated. The crude product obtained was dissolved in 50 ml tert-butanol, treated with 3.2 g (0.023 mol) KOH and the resulting mixture refluxed for 1.5 h. The solvent was evaporated and the residue distributed between icy water and $Et_2O$. The organic layer was washed with water and dried with $MgSO_4$. Evaporation of the solvent and column chromatography on silica gel with hexane/EtOAc 9:1 gave of 3.2 g (80%) 5-Bromo-6-fluoro-1H-indole, MS: 213 (M, 1Br).

16.3

To a solution of 2.1 g (9.81 mmol) 5-Bromo-6-fluoro-indole in 35 ml of DMF were added 1.54 g (13.76 mmol) KOtBu and 3.0 g (13.76 mmol) Di-tert.butylcarbonate, and the solution was stirred for 1 hr at room temperature and 30 min at 60° C. The mixture was poured into water, acidified with 2M aqueous HCl and extracted with $Et_2O$. Drying of the organic layers with $MgSO_4$, evaporation of the solvent, and chromatography on silica gel with hexane/EtOAc 49:1 gave 2.6 g (84%) 5-Bromo-6-fluoro-indole-1-carboxylic acid tert-butyl ester as a colorless liquid, MS: 313 (M, 1Br).

16.4

A mixture of 3.04 g (9.67 mmol) 5-Bromo-6-fluoro-indole-1-carboxylic acid tert-butyl ester, 670 mg (0.58 mmol) $Pd(PPh_3)_4$, and 111 mg (0.58 mmol) CuI in 25 ml of piperidine was heated to 60° C., treated with 1.61 ml (1.80 mmol) 4-pentyne-1-ol and stirred at 80° C. for 2 hrs. After cooling to room temperature the mixture was poured into water, acidified with 2M aqueous HCl and extracted with EtOAc. Drying of the combined organic layers with $MgSO_4$, evaporation of the solvent, and chromatography on silica gel with $CH_2Cl_2$ gave 2.6 g (85%) of 6-Fluoro-5-(5-hydroxy-pent-1-ynyl)-indole-1-carboxylic acid tert-butyl ester as a viscous orange oil, MS: 318 ($MH^+$).

16.5

A solution of 950 mg (0.3 mmol) 6-Fluoro-5-(5-hydroxy-pent-1-ynyl)-indole-1-carboxylic acid tert-butyl ester in 20 ml EtOH was treated with 2 ml of saturated aqeous NaOH and stirred during 2 hours at 60° C. 75% of the solvent were evaporated, the resulting mixture was poured into 5 ml of water, acidified with 2M aqueous HCl, and extracted with EtOAc. Drying of the combined organic layers with $MgSO_4$, evaporation of the solvent, and chromatography on silica gel with $CH_2Cl_2$ gave 550 mg (84%) of 5-(6-Fluoro-1H-indol-5-yl)-pent-4-yn-1-ol as a viscous light yellow oil, MS: 218 (M).

16.6

A solution of 109 mg (0.5 mmol) 5-(6-Fluoro-1H-indol-5-yl)-pent-4-yn-1-ol in 3 ml AcOH/TFA 2:1 was cooled to 0° C., treated with $NaCNBH_3$ and stirred for 1 hour at room temperature. The mixture was poured into icy water, made strongly alkaline by the addition of 2M NaOH, and extracted with EtOAc. Drying of the combined organic layers with $MgSO_4$, evaporation of the solvent, and chromatography on silica gel with $CH_2Cl_2$/MeOH 49:1 gave 80 mg (73%) of 5-(6-Fluoro-2,3-dihydro-1H-indol-5-yl)-pent-4-yn-1-ol as a colorless oil, MS: 220 ($MH^+$).

16.7

A solution of 99 mg (0.45 mmol) 5-(6-Fluoro-2,3-dihydro-1H-indol-5-yl)-pent-4-yn-1-ol and 0.155 ml (0.90 mmol) N-Ethyldiisopropylamine in 2 ml $CH_2Cl_2$ was treated with 0.125 ml (0.90 mmol) 4-chlorophenyl chloroformate and stirred at room temperature during 1 hour. The mixture was poured into water, extracted with EtOAc and the combined organic layers were dried with $MgSO_4$. Evaporation of the solvent, chromatography on silica gel with $CH_2Cl_2$/MeOH 49:1 gave 125 mg (74%) of 6-Fluoro-5-(5-hydroxy-pent-1-ynyl)-2,3-dihydro-indole-1-carboxylic acid 4-chloro-phenyl ester as a viscous light yellow oil, MS: 374 ($MH^+$, 1Cl).

16.8

In analogy to example 16.7, 5-(6-Fluoro-2,3-dihydro-1H-indol-5-yl)-pent-4-yn-1-ol and toluene-4-sulfonylchloride gave 5-[6-Fluoro-1-(toluene-4-sulfonyl)-2,3-dihydro-1H-indol-5-yl]-pent-4-yn-1-ol, MS: 374 ($MH^+$, 1Cl).

16.9

A solution of 120 mg (0.321 mmol) 6-Fluoro-5-(5-hydroxy-pent-1-ynyl)-2,3-dihydro-indole-1-carboxylic acid 4-chloro-phenyl ester and 0.164 ml (0.96 mmol) N-ethyldiisopropylamine in 2 ml $CH_2Cl_2$ was treated with 0.03 ml (0.385 mmol) of methanesulfonyl chloride and stirred at room temperature for 1 hour. The mixture was poured into $Et_2O$ and washed with 0.5 M HCl. Drying of the organic layer with $MgSO_4$, evaporation of the solvent, and chromatography on silica gel with $CH_2Cl_2$ gave 91 mg (61%) of 6-Fluoro-5-(5-methanesulfonyloxy-pent-1-ynyl)-2,3-dihydro-indole-1-carboxylic acid 4-chloro-phenyl ester as a colorless oil, MS: 452 ($MH^+$, 1Cl).

16.10

A solution of 30 mg (0.066 mmol) of 6-Fluoro-5-(5-methanesulfonyloxy-pent-1-ynyl)-2,3-dihydro-indole-1-carboxylic acid 4-chloro-phenyl ester and 0.1 ml (0.10 mmol) N-methylallylamine in 0.5 ml of DMF was stirred at 80° C. for 2 hours. The mixture was poured into 0.5 M aqueous NaOH and extracted with EtOAc. Drying of the combined organic layers with $MgSO_4$, evaporation of the solvent, and chromatography on silica gel with EtOAc/MeOH/$NEt_3$ 10:1:0.1 gave 19 mg (67%) of 5-[5-(Allyl-methyl-amino)-pent-1-ynyl]-6-fluoro-2,3-dihydro-indole-1-carboxylic acid 4-chloro-phenyl ester as a light brown oil, MS: 427 ($MH^+$, 1Cl).

16.11

In analogy to example 16.10, 6-Fluoro-5-(5-methanesulfonyloxy-pent-1-ynyl)-2,3-dihydro-indole-1-carboxylic acid 4-chloro-phenyl ester and 2-(methylamino) ethanol were converted to yield 6-Fluoro-5-{5-[(2-hydroxy-ethyl)-methyl-amino]-pent-1-ynyl}-2,3-dihydro-indole-1-carboxylic acid 4-chloro-phenyl ester as a colorless oil, MS: 430 (M, 1Cl).

16.12

In analogy to example 16.11, 6-Fluoro-5-(5-methanesulfonyloxy-pent-1-ynyl)-2,3-dihydro-indole-1-carboxylic acid 4-chloro-phenyl ester and 2(ethylamino) ethanol were converted to yield 5-{5-[Ethyl-(2-hydroxy-ethyl)-amino]-pent-1-ynyl}-6-fluoro-2,3-dihydro-indole-1-carboxylic acid 4-chloro-phenyl ester as a colorless oil, MS: 445 ($MH^+$, 1Cl).

16.13

A solution of 50 mg (0.141 mmol) of 5-[6-Fluoro-1-(toluene-4-sulfonyl)-2,3-dihydro-1H-indol-5-yl]-pent-4-yn-1-ol and 0.072 ml (0.42 mmol) diisopropyl ethylamine in 2 ml $CH_2Cl_2$ was treated at 0° C. with 0.033 ml (0.42 mmol) methanesulfonylchloride and stirred at room temperature for one hour. Addition of aqueous 0.1M HCl, extraction with $Et_2O$, drying of the organic layer with $MgSO_4$, and evaporation of the solvent gave 60 mg of Methanesulfonic acid 5-[6-fluoro-1-(toluene-4-sulfonyl)-2,3-dihydro-1H-indol-5-yl]-pent-4-ynyl ester as brown oil of which 12 mg were dissolved in 0.5 ml DMF, treated with 0.043 ml (0.053 mmol) 2-(methylamino)ethanol and stirred at 80° C. during 2 hours. Evaporation of the solvent and excess 2-(methylamino)ethanol and chromatography on silica gel with EtOAc/MeOH/$NEt_3$ 10:1:0.1 gave 10 mg (82%) of 2-({5-[6-Fluoro-1-(toluene-4-sulfonyl)-2,3-dihydro-1H-indol-5-yl]-pent-4-ynyl}-methyl-amino)-ethanol as a light yellow oil, MS: 431 ($MH^+$).

16.14

In analogy to example 16.13, 5-[6-Fluoro-1-(toluene-4-sulfonyl)-2,3-dihydro-1H-indol-5-yl]-pent-4-yn-1-ol and 2-(ethylamino)ethanol instead of 2-(methylamino)ethanol were converted to yield 2-(Ethyl-{5-[6-fluoro-1-(toluene-4-sulfonyl)-2,3-dihydro-1H-indol-5-yl]-pent-4-ynyl}-amino)-ethanol as a light yellow oil, MS: 445 ($MH^+$).

Example 17

17.1

Hydrogenolysis at atmospheric pressure of 5 mg (0.013 mmol) 5-[5-(Allyl-methyl-amino)-pent-1-ynyl]-6-fluoro-2,3-dihydro-indole-1-carboxylic acid 4-chloro-phenyl ester in 0.5 ml AcOH in the presence of 5 mg 10% Pd/C during 12 hrs, followed by filtration, evaporation of the AcOH, distribution of the residue between $Et_2O$ and 0.5 M NaOH, drying of the organic layer with $Na_2SO_4$, evaporation of the solvent and chromatograpy on silica gel with EtOAc/MeOH/$NEt_3$ 10:1:0.1 gave 3 mg (64%) of 6-Fluoro-5-[5-(methyl-propyl-amino)-pentyl]-2,3-dihydro-indole-1-carboxylic acid phenyl ester as a yellow oil, MS: 399 ($MH^+$)

17.2

In analogy to example 17.1, hydrogenolysis of 2-({5-[6-Fluoro-1-(toluene-4-sulfonyl)-2,3-dihydro-1H-indol-5-yl]-pent-4-ynyl}-methyl-amino)-ethanol yielded 2-({5-[6-Fluoro-1-(toluene-4-sulfonyl)-2,3-dihydro-1H-indol-5-yl]-pentyl}-methyl-amino)-ethanol. MS: 435 ($MH^+$).

Example A

Tablets containing the following ingredients can be manufactured in a conventional manner:

| Ingredients | Per tablet |
|---|---|
| Compound of formula I | 10.0–100.0 mg |
| Lactose | 125.0 mg |
| Maize starch | 75.0 mg |
| Talc | 4.0 mg |
| Magnesium stearate | 1.0 mg |

Example B

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

Example C

Injection solutions can have the following composition:

| | |
|---|---|
| Compound of formula I | 3.0 mg |
| Gelatine | 150.0 mg |
| Phenol | 4.7 mg |
| Water for injection solutions | ad 1.0 ml |

What is claimed is:

1. A compound selected from the group consisting of: compounds of formula (I)

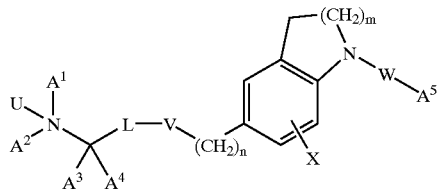 (I)

wherein
U is O or a lone pair,
V is a) O, S, $NR^1$, or $CH_2$, and L is lower-alkylene or lower-alkenylene,
b) —CH=CH— or —C≡C—, and L is lower-alkylene or a single bond,
W is CO, COO, $CONR^2$, CSO, $CSNR^2$, $SO_2$, or $SO_2NR^2$,
X is hydrogen or one or more optional halogen and/or lower-alkyl substituents,
m is 1,
n is 0 to 7,
$A^1$ is hydrogen, lower-alkenyl, or lower-alkyl optionally substituted by hydroxy, lower-alkoxy, or thio-lower-alkoxy,
$A^2$ is cycloalkyl, cycloalkyl-lower-alkyl, lower-alkenyl, lower-alkinyl, or lower-alkyl optionally substituted by hydroxy, lower-alkoxy or thio-lower-alkoxy,
$A^3$ and $A^4$ independently from each other are hydrogen or lower-alkyl, or
$A^1$ and $A^2$ or $A^1$ and $A^3$ are bonded to each other to form a ring and —$A^1$—$A^2$— or
—$A^1$—$A^3$— are lower-alkylene or lower-alkenylene, optionally substituted by $R^3$, in which one —$CH_2$— group of —$A^1$—$A^2$— or —$A^1$—$A^3$— can optionally be replaced by $NR^4$, S, or O,
$A^5$ is cycloalkyl, cycloalkyl-lower-alkyl, heterocycloalkyl-lower-alkyl, aryl, aryl-lower-alkyl, heteroaryl, heteroaryl-lower-alkyl, lower-alkyl optionally substituted with hydroxy or lower-alkoxy, alkenyl optionally substituted with hydroxy, or alkadienyl optionally substituted with hydroxy,
$R^3$ is hydroxy, lower-alkoxy, thio-lower-alkoxy, N($R^5$, $R^6$), or lower-alkyl optionally substituted by hydroxy,
$R^1$, $R^2$, $R^4$, $R^5$, and $R^6$ independently from each other are hydrogen or lower-alkyl;
pharmaceutically acceptable salts of compounds of formula (I); and
pharmaceutically acceptable esters of compounds of formula (I).

2. The compound according to claim 1, wherein U is a lone pair.

3. The compound according to claim 2, wherein V is O or $CH_2$, and L is lower-alkylene or lower-alkenylene.

4. The compound according to claim 2, wherein V is —C≡C— and L is lower-alkylene or a single bond.

5. The compound according to claim 3, wherein n is 0.

6. The compound according to claim 3, wherein $A^1$ is lower-alkyl.

7. The compound according to claim 6, wherein $A^1$ is methyl or ethyl.

8. The compound according to claim 3, wherein $A^2$ is lower-alkenyl, or lower-alkyl optionally substituted by hydroxy or lower-alkoxy.

9. The compound according to claim 8, wherein $A^2$ is 2-propenyl or 2-hydroxy-ethyl.

10. The compound according to claim 3, wherein $A^1$ and $A^2$ are bonded to each other to form a ring and —$A^1$—$A^2$— is lower-alkylene or lower-alkenylene, optionally substituted by $R^3$, in which one —$CH_2$— group of —$A^1$—$A^2$— can optionally be replaced by $NR^4$, S, or O, wherein $R^3$ and $R^4$ are as defined in claim 1.

11. The compound according to claim 3, wherein $A^3$ is hydrogen.

12. The compound according to claim 11, wherein $A^4$ is hydrogen.

13. The compound according to claim 3, wherein $A^5$ is cycloalkyl, cycloalkyl-lower-alkyl, heterocycloalkyl-lower-alkyl, aryl, aryl-lower-alkyl, heteroaryl, heteroaryl-lower-alkyl, or lower-alkyl optionally substituted with hydroxy or lower-alkoxy.

14. The compound according to claim 13, wherein $A^5$ is phenyl or benzyl, optionally substituted by 1 to 3 substituents independently selected from the group consisting of fluorine and chlorine, or wherein $A^5$ is lower-alkyl.

15. The compound according to claim 14, wherein $A^5$ is phenyl, 4-fluoro-phenyl, 4-chloro-phenyl, butyl, or pentyl.

16. The compound according to claim 3, wherein W is COO, $CONR^2$, CSO, or $CSNR^2$, and $R^2$ is hydrogen.

17. The compound according to claim 3, wherein X is hydrogen.

18. The compound according to claim 3, wherein X is fluorine.

19. A compound according to claim 2, selected from the group consisting of:

5-[5-(Allyl-methyl-amino)-pent-1-ynyl]-6-fluoro-2,3-dihydro-indole-1-carboxylic acid 4-chloro-phenyl ester, 5-{5-[Ethyl-(2-hydroxy-ethyl)-amino]-pent-1-ynyl}-6-fluoro-2,3-dihydro-indole-1-carboxylic acid 4-chloro-phenyl ester, 6-Fluoro-5-[5-(methyl-propyl-amino)-pentyl]-2,3-dihydro-indole-1-carboxylic acid phenyl ester, and pharmaceutically acceptable salts or pharmaceutically acceptable esters thereof.

20. A compound selected from the group consisting of: compounds of formula (VII)

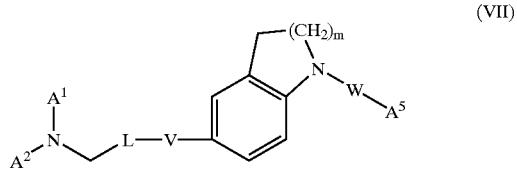 (VII)

wherein
V is O or $CH_2$;
L is lower-alkylene or lower-alkenylene;
W is COO, CONH, CSNH or CSO;
$A^1$ is hydrogen or lower-alkyl;
$A^2$ is lower alkyl or lower alkenyl;
m is 1; and
$A^5$ is lower alkyl, phenyl or lower alkyl phenyl, wherein the phenyl group is optionally substituted with halogen;
pharmaceutically acceptable salts of compounds of formula (VII); and
pharmaceutically acceptable esters of compound of formula (VII).

21. The compound according to claim 20, wherein V is CH$_2$.

22. The compound according to claim 21, wherein m is 1.

23. The compound according to claim 22, wherein W is COO.

24. The compound according to claim 23, wherein the compound of formula (VII) is 5-[5-(Allyl-methyl-amino)-pentyl]-2,3-dihydro-indole-1-carboxylic acid 4-chloro-phenyl ester.

25. The compound according to claim 24, which is 5-[5-(Allyl-methyl-amino)-pentyl]-2,3-dihydro-indole-1-carboxylic acid 4-chloro-phenyl ester.

26. The compound according to claim 22, wherein W is CONH.

27. The compound according to claim 26, wherein the compound of formula (VII) is 5-[5-(Allyl-methyl-amino)-pentyl]-2,3-dihydro-indole-1-carboxylic acid (4-fluoro-phenyl)-amide.

28. The compound according to claim 27, which is 5-[5-(Allyl-methyl-amino)-pentyl]-2,3-dihydro-indole-1-carboxylic acid (4-fluoro-phenyl)-amide.

29. The compound according to claim 22, wherein W is CSNH.

30. The compound according to claim 29, wherein the compound of formula (VII) is 5-[5-(Allyl-methyl-amino)-pentyl]-2,3-dihydro-indole-1-carbothioic acid (4-chloro-phenyl)-amide.

31. The compound according to claim 30, which is 5-[5-(Allyl-methyl-amino)-pentyl]-2,3-dihydro-indole-1-carbothioic acid (4-chloro-phenyl)-amide.

32. The compound according to claim 29, wherein the compound of formula (VII) is 5-[5-(Allyl-methyl-amino)-pentyl]-2,3-dihydro-indole-1-carbothioic acid 4-chloro-benzylamide.

33. The compound according to claim 32, which is 5-[5-(Allyl-methyl-amino)-pentyl]-2,3-dihydro-indole-1-carbothioic acid 4-chloro-benzylamide.

34. The compound according to claim 22, wherein W is CSO.

35. The compound according to claim 34, wherein the compound of formula (VII) is 5-[5-(Allyl-methyl-amino)-pentyl]-2,3-dihydro-indole-1-carbothioic acid O-(4-chloro-phenyl)ester.

36. The compound according to claim 35, which is 5-[5-(Allyl-methyl-amino)-pentyl]-2,3-dihydro-indole-1-carbothioic acid O-(4-chloro-phenyl)ester.

37. The compound according to claim 34, wherein the compound of formula (VII) is 5-[5-(Allyl-methyl-amino)-pentyl]-2,3-dihydro-indole-1-carbothioic acid O-(4-fluoro-phenyl)ester.

38. The compound according to claim 37, which is 5-[5-(Allyl-methyl-amino)-pentyl]-2,3-dihydro-indole-1-carbothioic acid O-(4-fluoro-phenyl)ester.

39. The compound according to claim 20, wherein V is O.

40. The compound according to claim 39, wherein m is 1.

41. The compound according to claim 40, wherein W is COO.

42. The compound according to claim 40, wherein W is CONH.

43. The compound according to claim 40, wherein W is CSNH.

44. The compound according to claim 43, wherein the compound of formula (VII) is 5-[4-(Allyl-methyl-amino)-butoxy]-2,3-dihydro-indole-1-carbothioic acid 4-fluoro-benzylamide.

45. The compound according to claim 44, which is 5-[4-(Allyl-methyl-amino)-butoxy]-2,3-dihydro-indole-1-carbothioic acid 4-fluoro-benzylamide.

46. The compound according to claim 43, wherein the compound of formula (VII) is 5-[4-(Allyl-methyl-amino)-butoxy]-2,3-dihydro-indole-1-carbothioic acid butylamide.

47. The compound according to claim 46, which is 5-[4-(Allyl-methyl-amino)-butoxy]-2,3-dihydro-indole-1-carbothioic acid butylamide.

48. The compound according to claim 43, wherein the compound of formula (VII) is 5-[4-(Allyl-methyl-amino)-butoxy]-2,3-dihydro-indole-1-carbothioic acid (2-methyl-butyl)-amide.

49. The compound according to claim 48, which is 5-[4-(Allyl-methyl-amino)-butoxy]-2,3-dihydro-indole-1-carbothioic acid (2-methyl-butyl)-amide.

50. The compound according to claim 40, wherein W is CSO.

51. The compound according to claim 50, wherein the compound of formula (VII) is 5-[4-(Allyl-methyl-amino)-butoxy]-2,3-dihydro-indole-1-carbothioic acid O-(4-chloro-phenyl)ester.

52. The compound according to claim 51, which is 5-[4-(Allyl-methyl-amino)-butoxy]-2,3-dihydro-indole-1-carbothioic acid O-(4-chloro-phenyl)ester.

53. A pharmaceutical composition comprising a compound according to claim 1 and at least one of a pharmaceutically acceptable carrier or pharmaceutically acceptable adjuvant.

* * * * *

UNITED STATES PATENT AND TRADEMARK OFFICE
CERTIFICATE OF CORRECTION

PATENT NO. : 6,706,751 B2
DATED : March 16, 2004
INVENTOR(S) : Johannes Aeibi et al.

It is certified that error appears in the above-identified patent and that said Letters Patent is hereby corrected as shown below:

Title page,
Item [74], Assignee, delete "Hoffman-La Roche Inc., Nutley, NJ (US)" and insert
-- Hoffmann-La Roche Inc., Nutley, NJ (US) --.

Signed and Sealed this

Fourteenth Day of December, 2004

JON W. DUDAS
*Director of the United States Patent and Trademark Office*